(12) United States Patent
Barron et al.

(10) Patent No.: US 8,445,632 B2
(45) Date of Patent: May 21, 2013

(54) SELECTIVE POLY-N-SUBSTITUTED GLYCINE ANTIBIOTICS

(75) Inventors: Annelise E. Barron, Palo Alto, CA (US); Ann M. Czyzewski, Grayslake, IL (US); Michelle T. Dohm, Palos Park, IL (US); Tyler M. Miller, Aurora, CO (US); Ronald N. Zuckermann, El Cerrito, CA (US); James A. Patch, Cornwall-on-Hudson, NY (US); Nathaniel P. Chongsiriwatana, Albuquerque, NM (US)

(73) Assignees: The Regents of the University of California, Oakland, CA (US); Northwestern University, Evanston, IL (US)

( * ) Notice: Subject to any disclaimer, the term of this patent is extended or adjusted under 35 U.S.C. 154(b) by 507 days.

(21) Appl. No.: 12/378,034

(22) Filed: Feb. 9, 2009

(65) Prior Publication Data

US 2010/0036088 A1 Feb. 11, 2010

Related U.S. Application Data

(60) Provisional application No. 61/065,189, filed on Feb. 8, 2008.

(51) Int. Cl.
*C07K 4/00* (2006.01)
*C07K 7/06* (2006.01)
*A61K 38/03* (2006.01)
*A61K 38/08* (2006.01)

(52) U.S. Cl.
USPC .............. 530/300; 514/2.4; 530/330

(58) Field of Classification Search
None
See application file for complete search history.

(56) References Cited

U.S. PATENT DOCUMENTS

| 6,562,785 B1 | 5/2003 | Shapiro | |
|---|---|---|---|
| 2002/0115612 A1* | 8/2002 | Zuckermann et al. | 514/12 |
| 2004/0161798 A1* | 8/2004 | Kodadek | 435/7.1 |
| 2006/0019912 A1 | 1/2006 | Burkoth | |
| 2006/0035944 A1 | 2/2006 | Muto et al. | |
| 2007/0087972 A1 | 4/2007 | Peretz et al. | |

FOREIGN PATENT DOCUMENTS

WO 94/06451 3/1994

OTHER PUBLICATIONS

Heine et al. Synthesis and screening of peptoid arrays on cellulose membranes. Tetrahedron. 2003, vol. 59, pp. 9919-9930.*
Kirshenbaum et al. Sequence-specific polypeptoids: A diverse family of heteropolymers with stable secondary structure. Proceedings of the National Academy of Science USA. Apr. 1998, vol. 95, pp. 4303-4308.*
Wu et al. Structural and Spectroscopic Studies of Peptoid Oligomers . . . Journal of the American Chemical Society. Oct. 11, 2003, vol. 125, No. 44, pp. 13525-13530.*
Patch, et al. Versatile Oligo(N-Substituted) Glycines: The Many Roles of Peptoids in Drug Discover. Pseudo Peptides in Drug Development edited by Peter E. Nielsen, Copyright 2004, Wiley-VCH Verlag GmbH & Co., Nov. 19, 2003, pp. 1-31, esp. p. 6, sec.1.3; p. 7, Fig. 13; p. 8, Fig 1.4; p. 14, Table 1.2.

(Continued)

Primary Examiner — Jeffrey E Russel
(74) Attorney, Agent, or Firm — Reinhart Boerner Van Deuren s.c.

(57) ABSTRACT

Antimicrobial peptoid compounds and related compositions as can be used against bacteria effectively and selectively.

18 Claims, 31 Drawing Sheets

OTHER PUBLICATIONS

Chongsiriwatana, et al. Peptoids that mimic the structure, function, and mechanism of helical antimicrobial peptides. PNAS, Feb. 26, 2008, vol. 105, No. 8, pp. 2794-2799, esp. p. 2795, Fig. 2, Table 1.

J. A. Patch et al "Versatile Oligo (N-Substituted) Glycines: The Many Roles of Peptoids in Drug Delivery" In: "Pseudo-Peptides in Drug Development", Jan. 28, 2005, Wiley-VCH Verlag GmbH & Co. KgaA, XP55006124, pp. 1-31.

James A. Patch et al "Helical Peptoid Mimics of Magainin-2 Amide", Journal of the Amerrican Chemical Society, vol. 125, No. 40, Oct. 1, 2003, pp. 12092-12093, XP55017017, ISSN: 0002-7863, DOI: 10.1021/ja037320d.

Byoung-Chul Lee et al "Folding a Nonbiological Polymer into a Compact Multihelical Structure", Journal of the American Chemical Society, vol. 127, No. 31, Aug. 1, 2005, pp. 10999-11009, XP55006138, ISSN: 0002-7863, DOI: 10.1021/ja0514904.

Fateh Singh Nandel et al "Conformational Study of Short Peptoid Models for Future Applications as Potent Antimicrobial Compounds", Macromolecular Theory and Simulations, vol. 16, No. 3, Mar. 23, 2007, pp. 295-303, XP55017019, ISSN: 1022-1344, DOI: 10.1002/mats.2006000080.

Shannon L. Seurync-Servoss et al "Effects of Including an N-Terminal Insertion Region and Arginine-Mimetic Side Chains in Helical Peptoid Analogues of Lung Surfactant Protein B +", Biochemistry, vol. 45, No. 39, Oct. 1, 2006, pp. 11809-11818, XP55017018, ISSN: 0006-2960, DOI: 10.1021/bi060617e.

Seurynck S L et al "Simple, Helical Peptoid Analogs of Lung Surfactant Protein B", Chemistry and Biology, Current Biology, London GB, vol. 12, No. 1, Jan. 1, 2005, pp. 77-88, XP004722466, ISSN: 1074-5521, DOI: 10.1016/J.Chembiol.2004.10.014.

\* cited by examiner

Figure 6
Fig. A
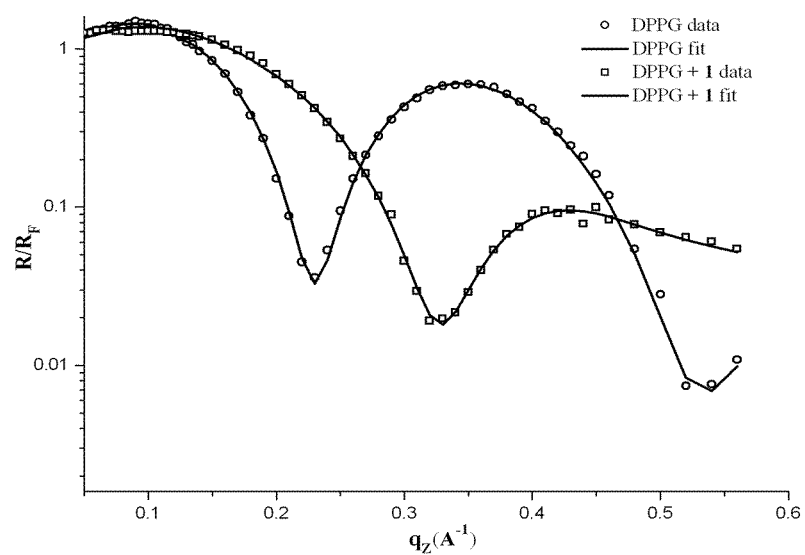
Fig. B
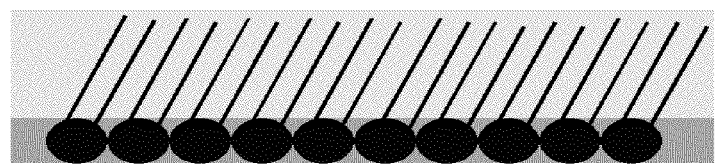
Fig. C
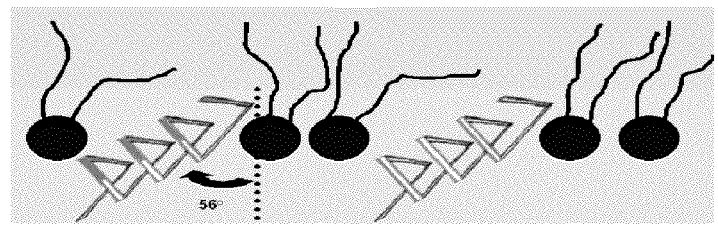

Figure 10A: 10mM Tris buffer
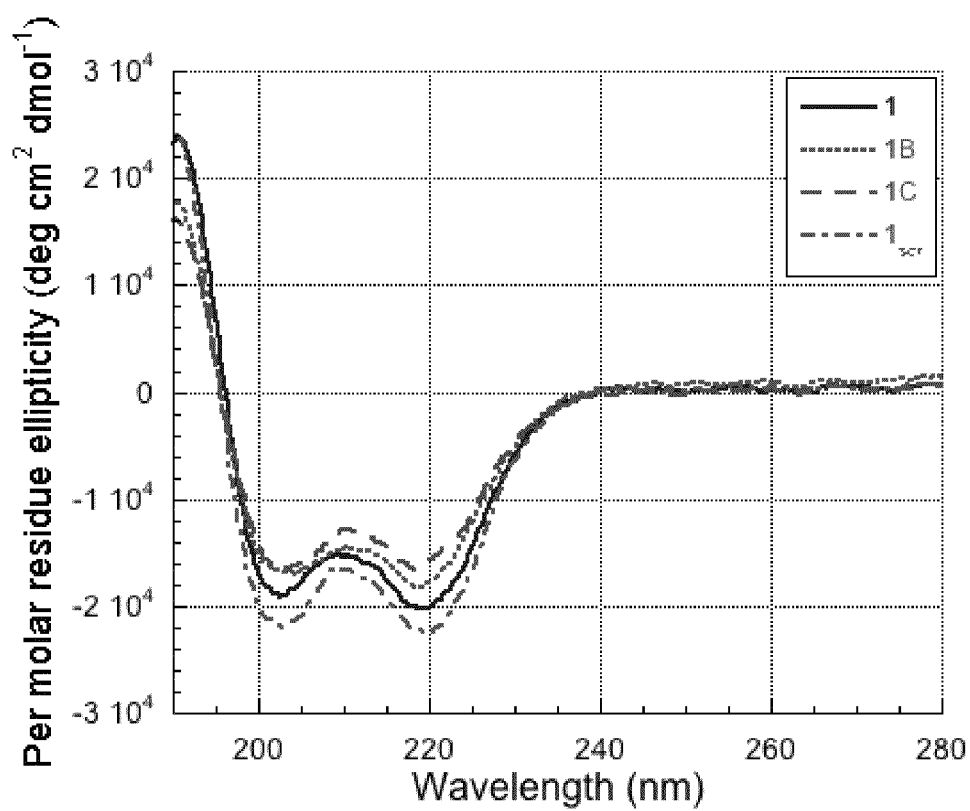

Figure 10B: 5mM POPC:CH (2:1) SUVs
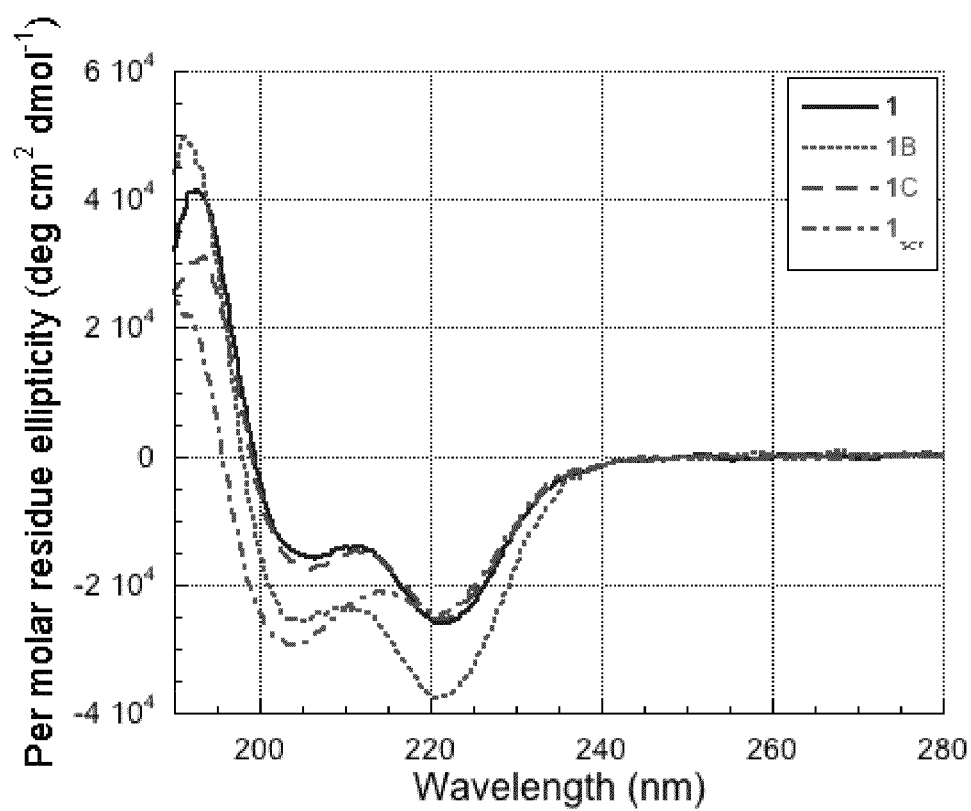

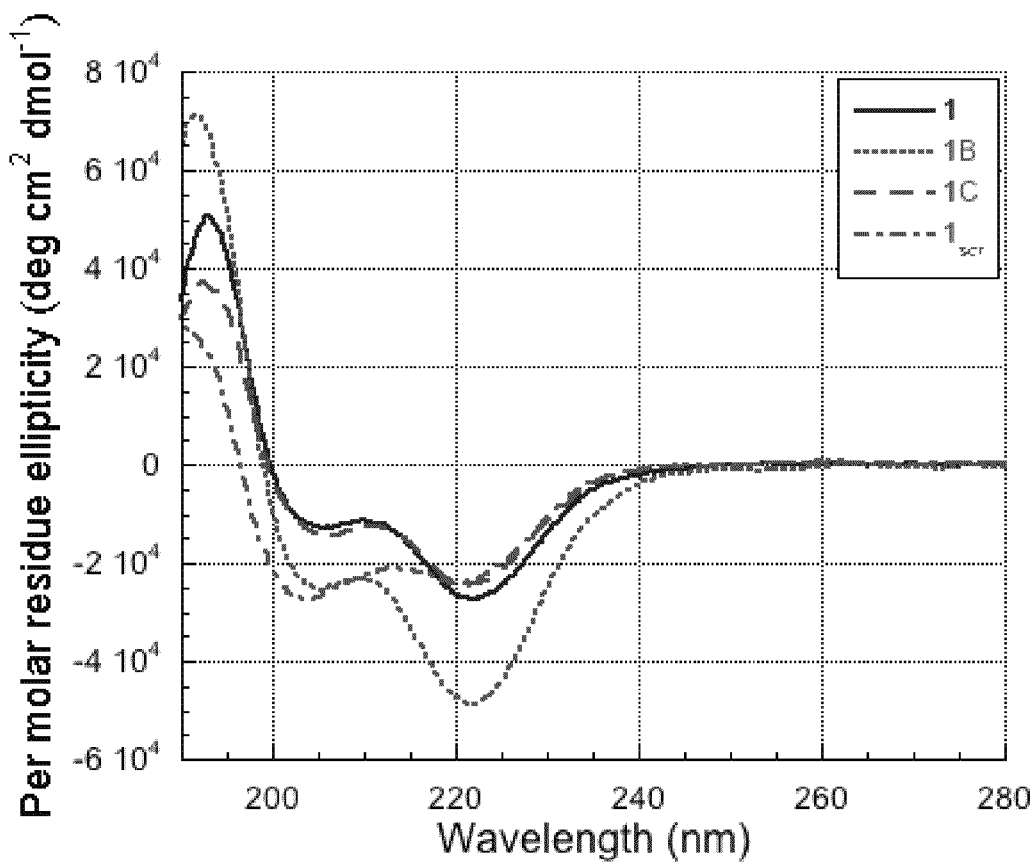
Figure 10C: 5mM POPE: POPG (3:7) SUVs

Figure 11A: 10mM Tris buffer
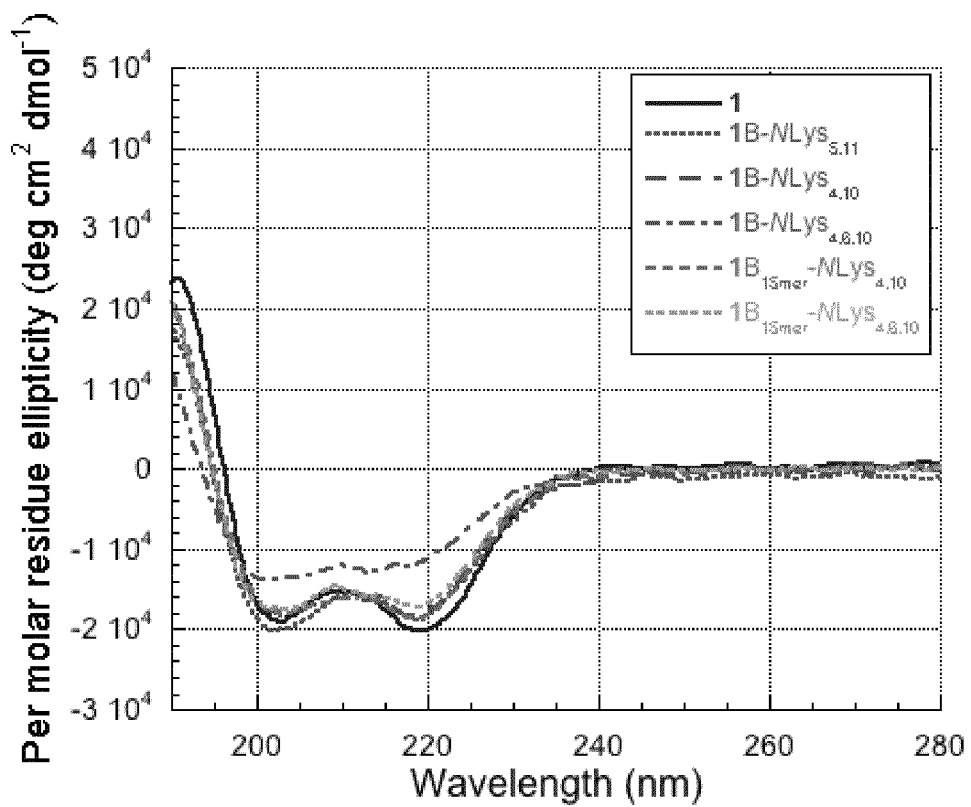

Figure 11B: 5mM POPC:CH
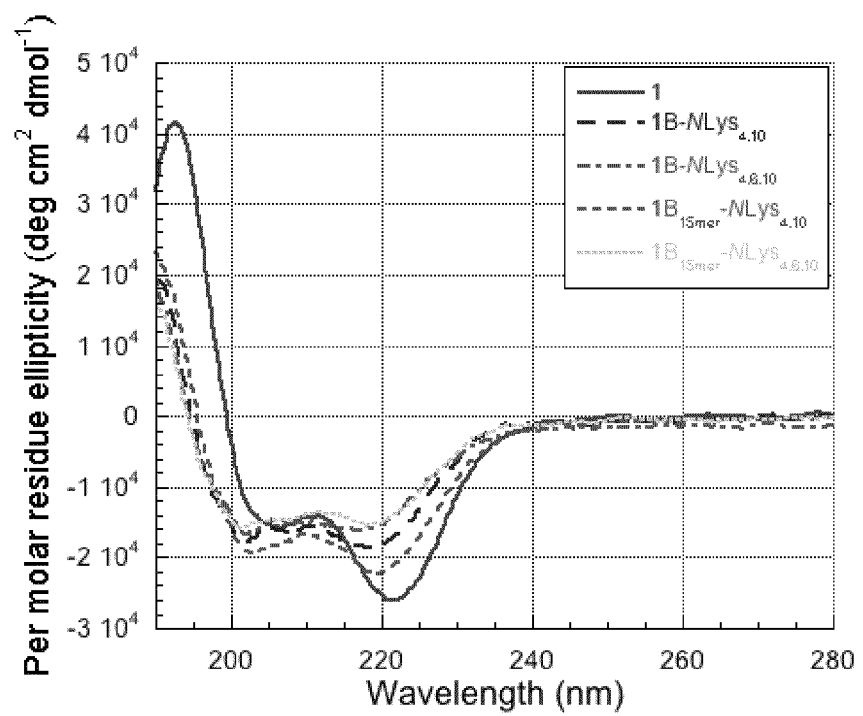

Figure 12A: 10mM Tris buffer
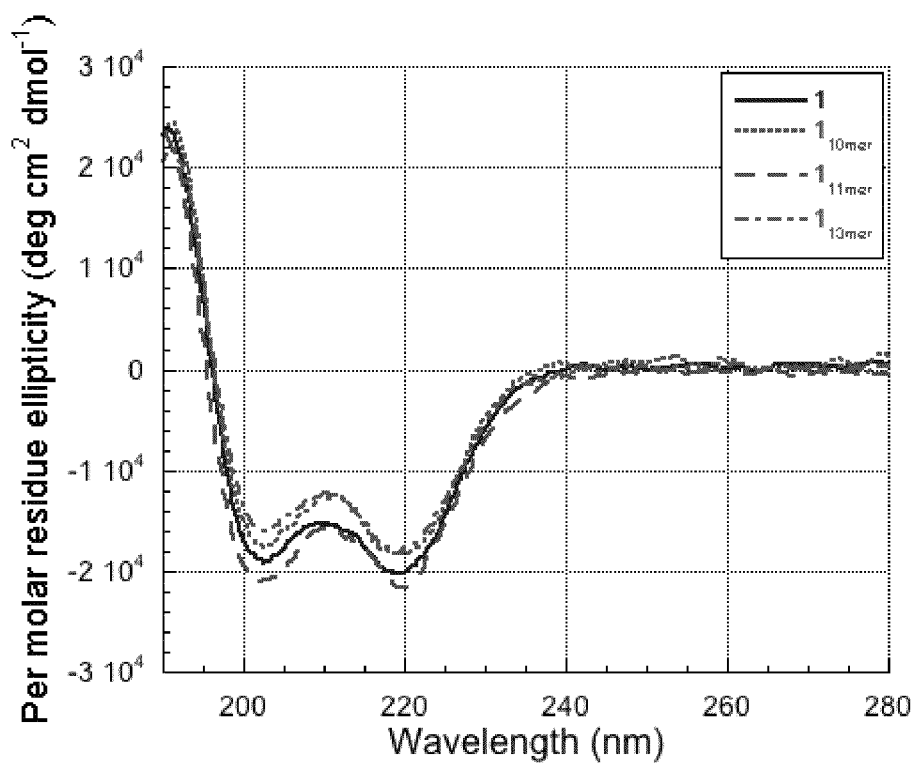

Figure 12B: 5mM POPC:CH
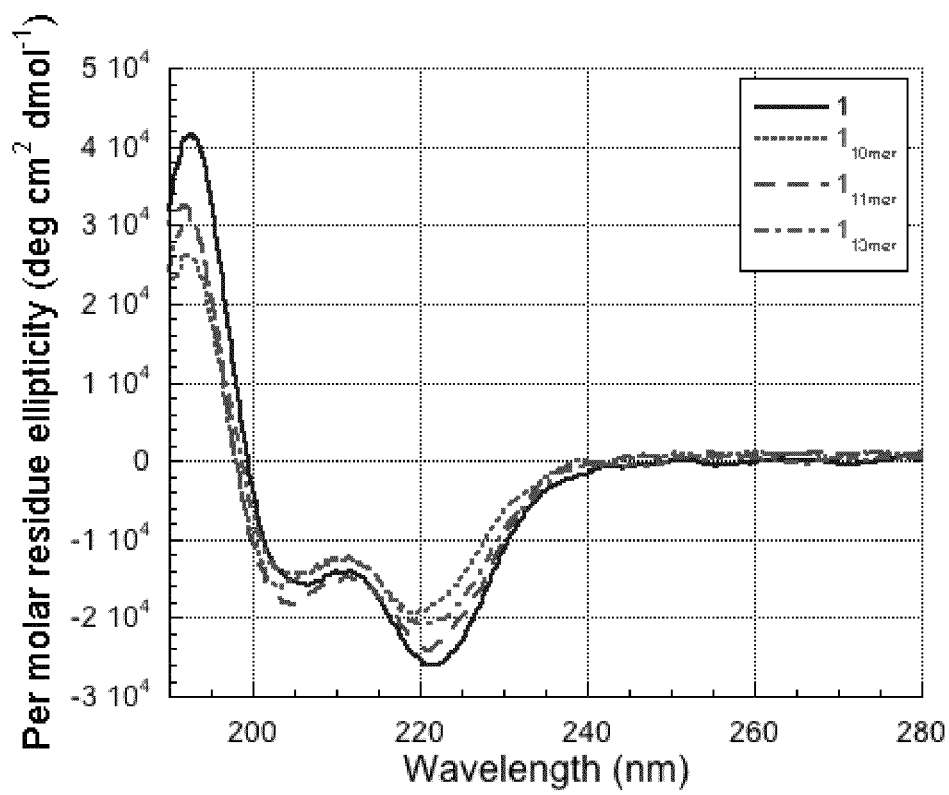

Figure 12C: 5mM POPE:POPG
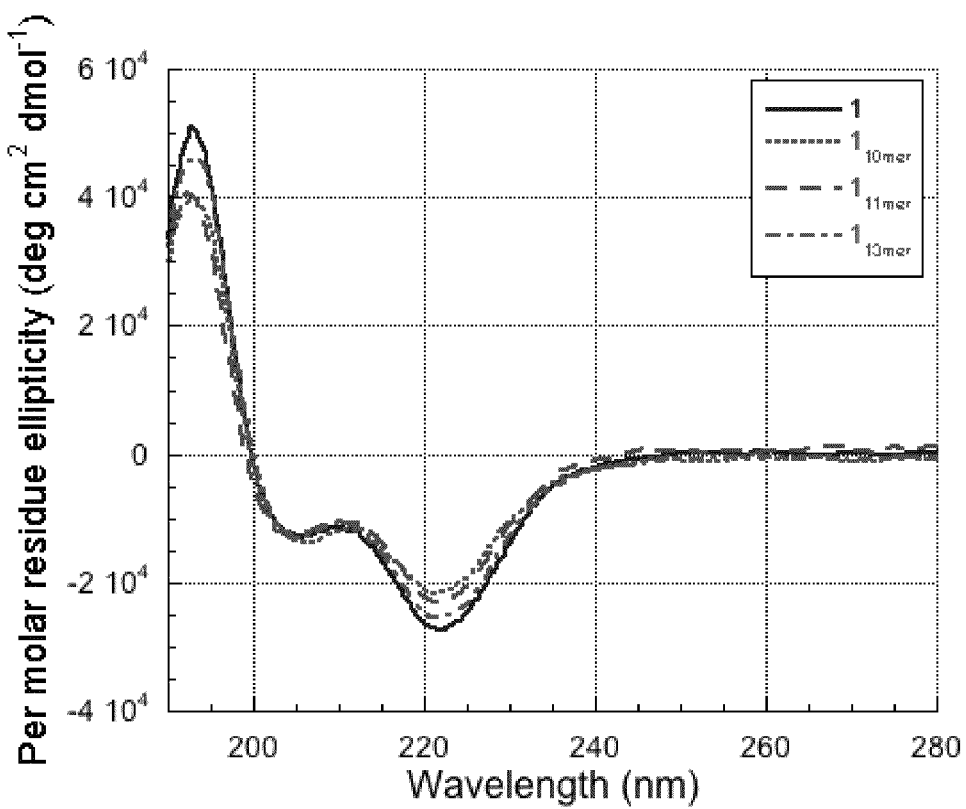

Figure 13A: 10mM Tris buffer
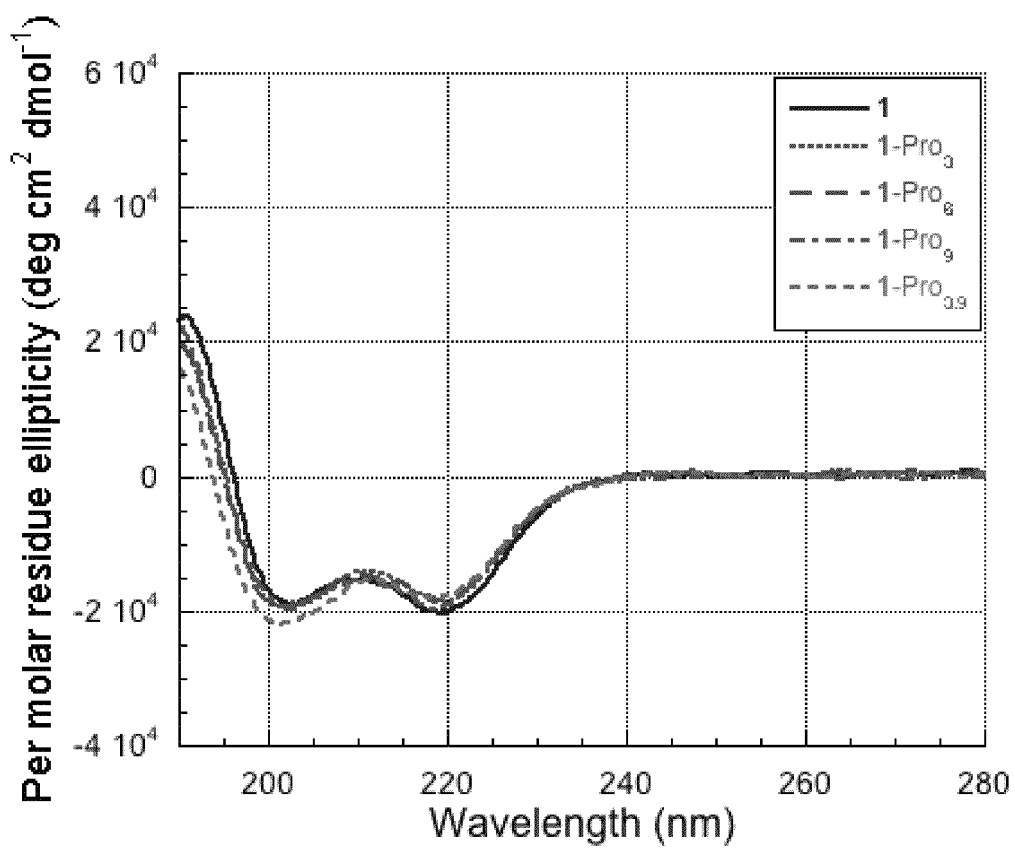

Figure 13B: 5mM POPE:CH SUVs
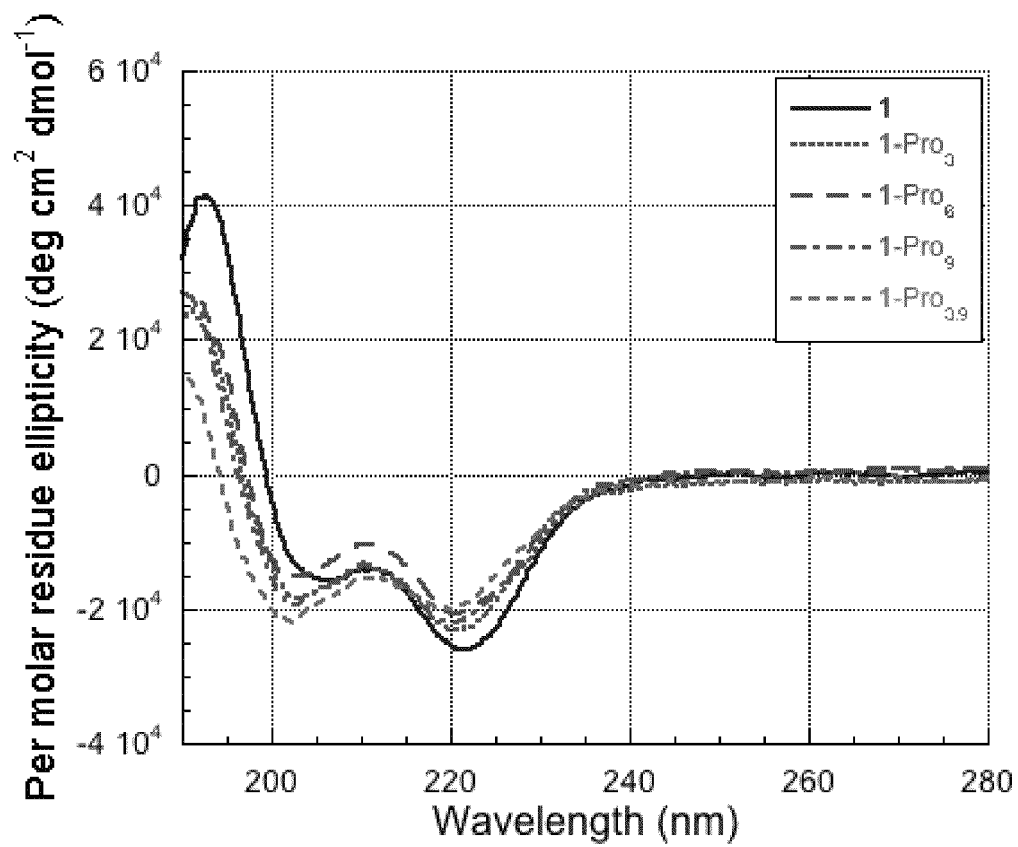

Figure 13C: 5mM POPE:POPG SUVs
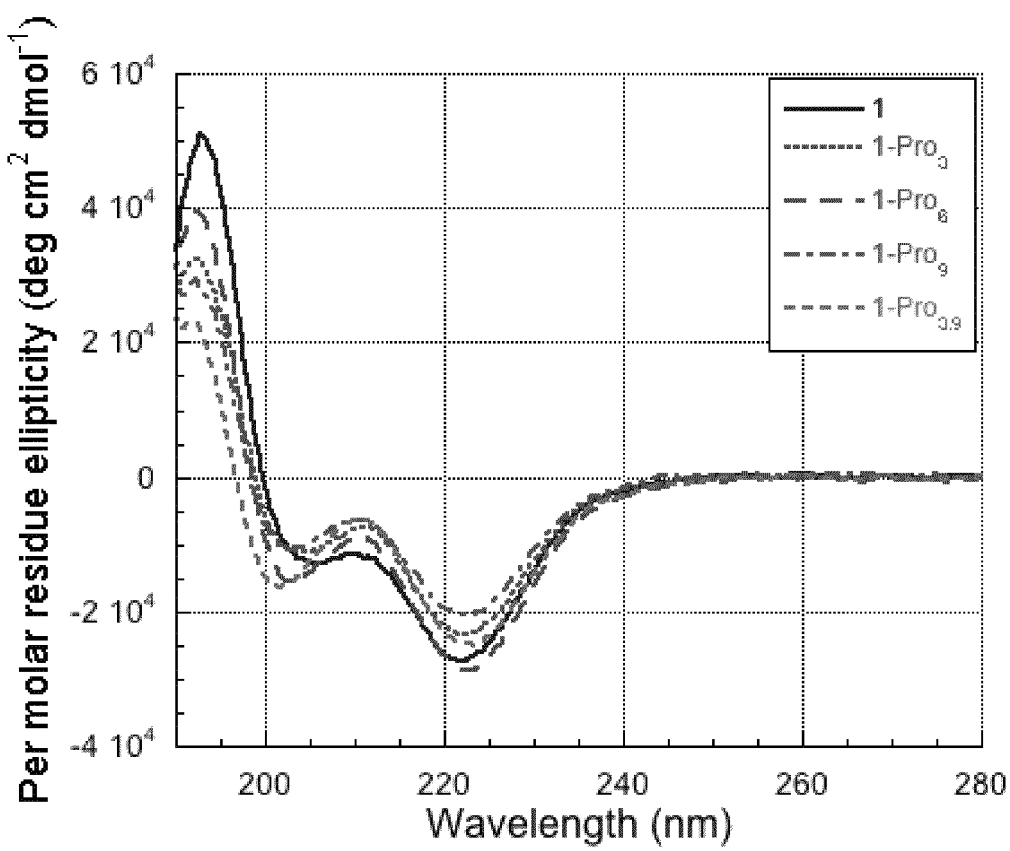

Figure 14A: 10mM Tris buffer
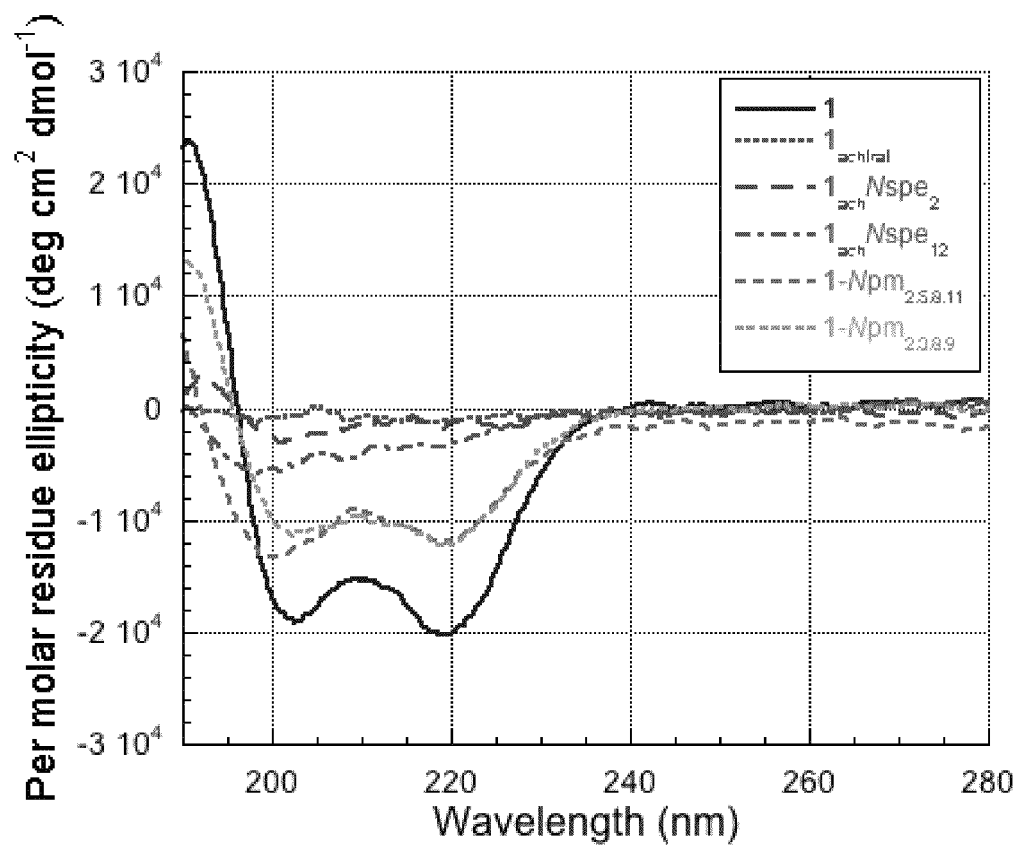

Figure 14B: 5mM POPE:CH
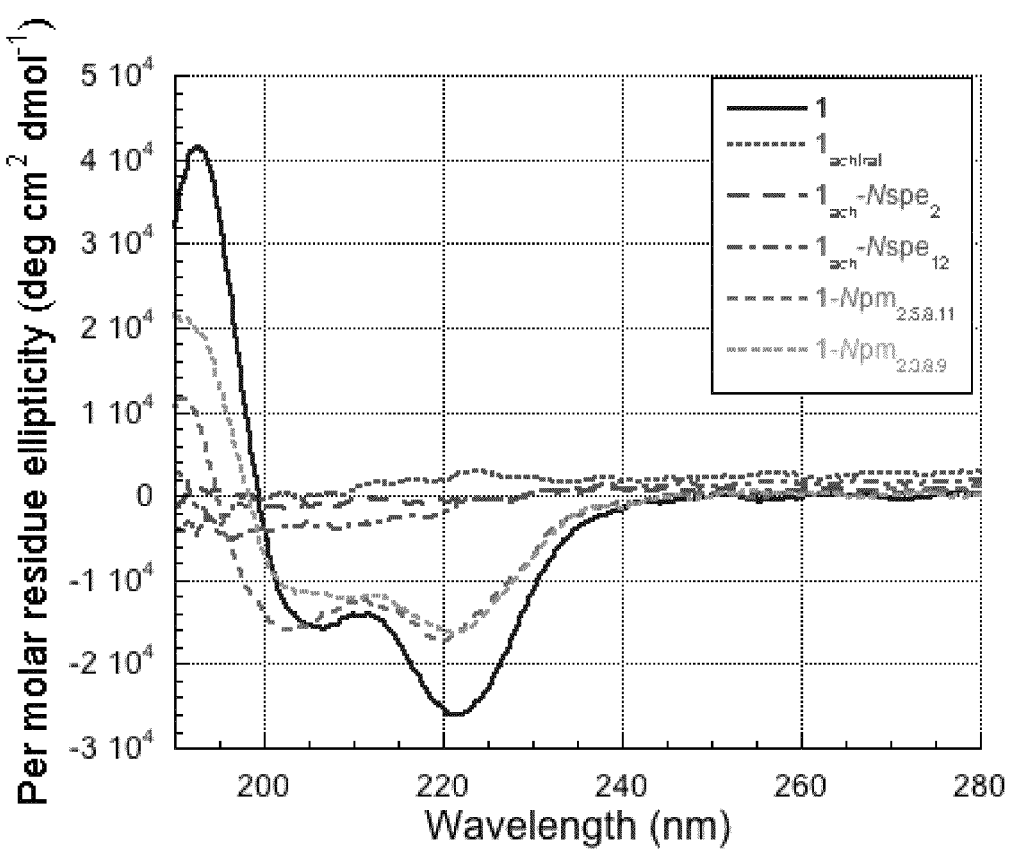

Figure 14C: 5mM POPE:POPG
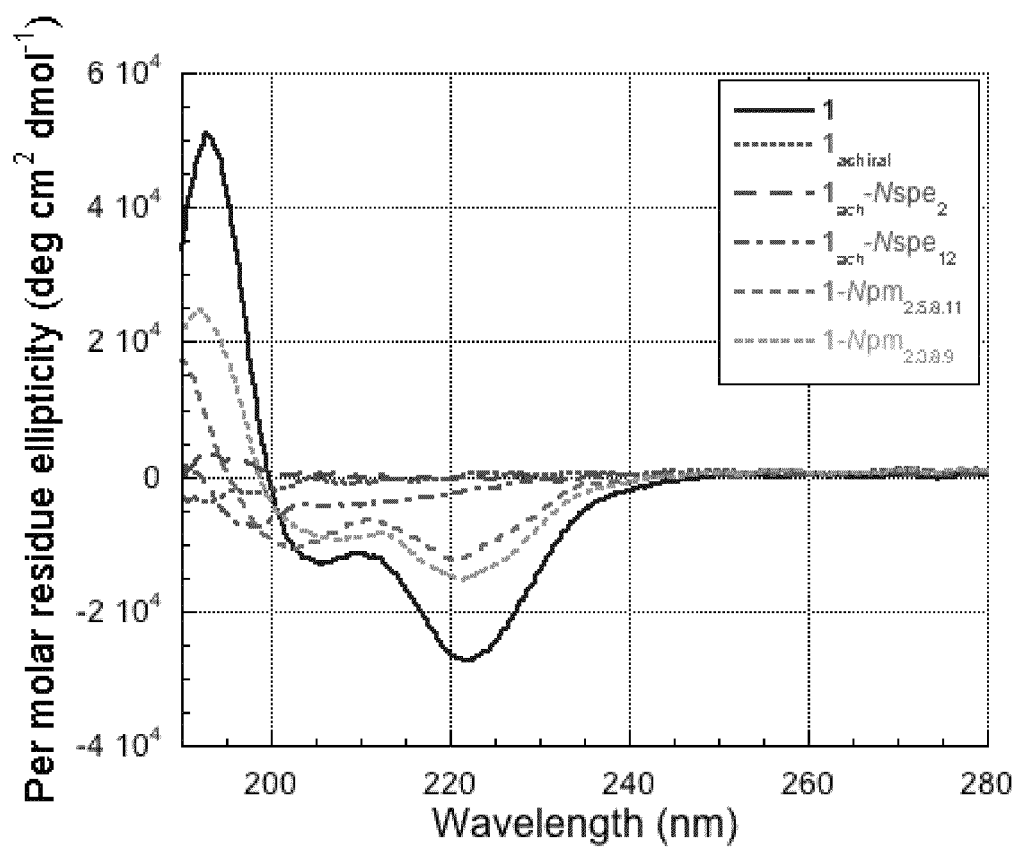

Figure 15A: 10mM Tris buffer
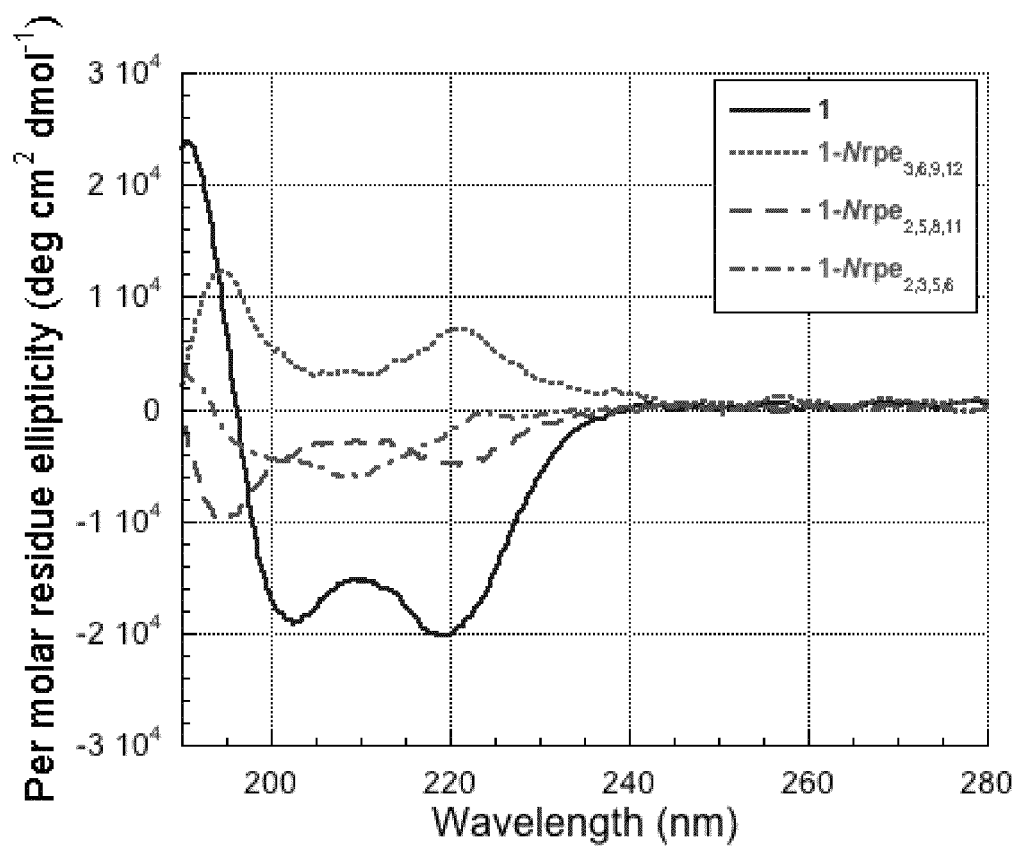

Figure 15B: 5mM POPE:CH
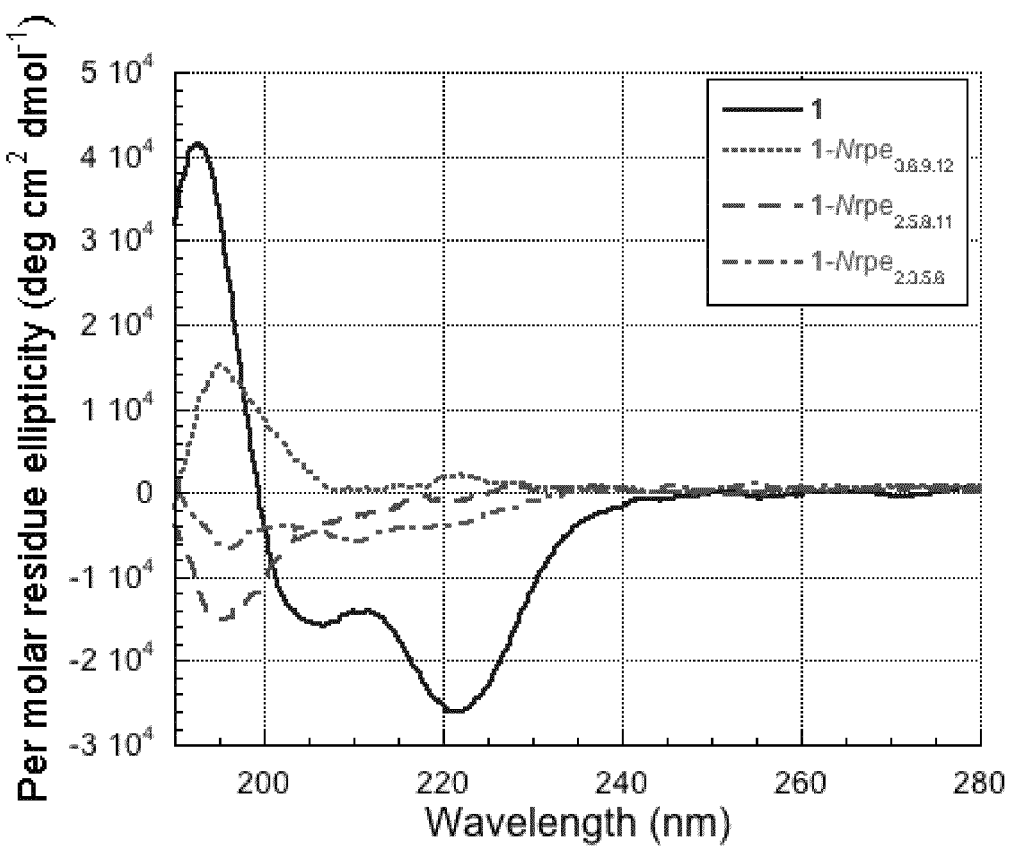

Figure 15C: 5mM POPE:POPG
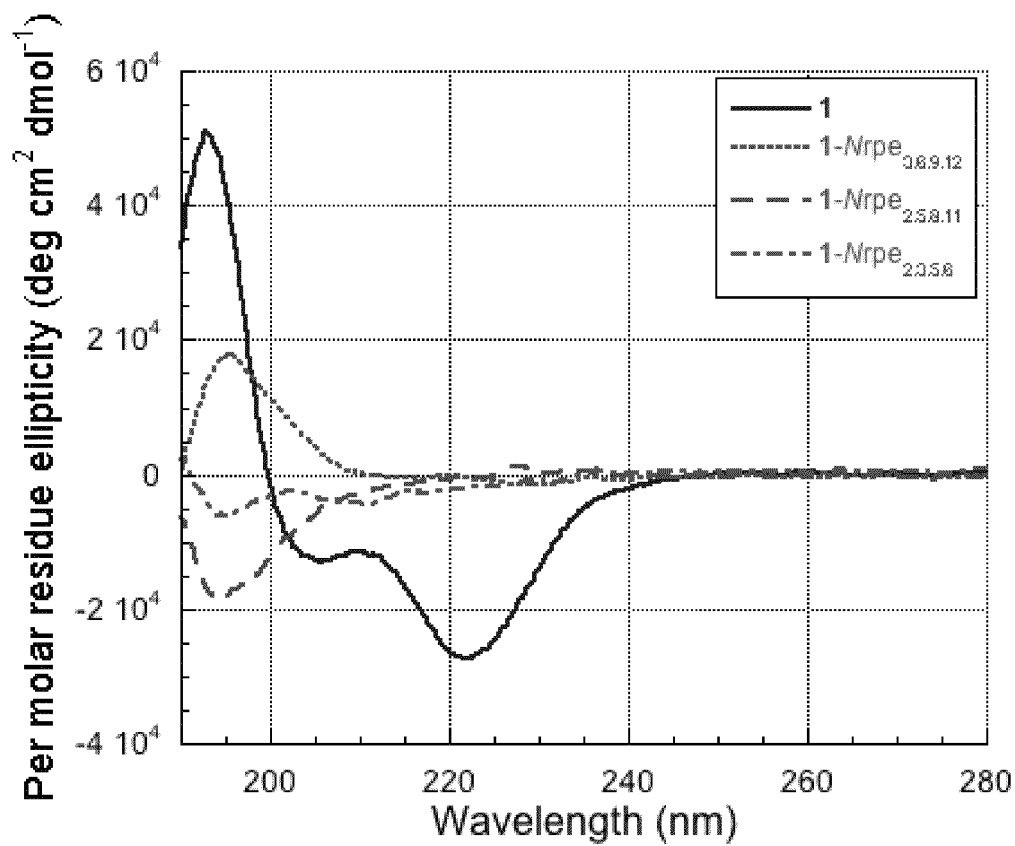

Figure 16A: 10mM Tris buffer
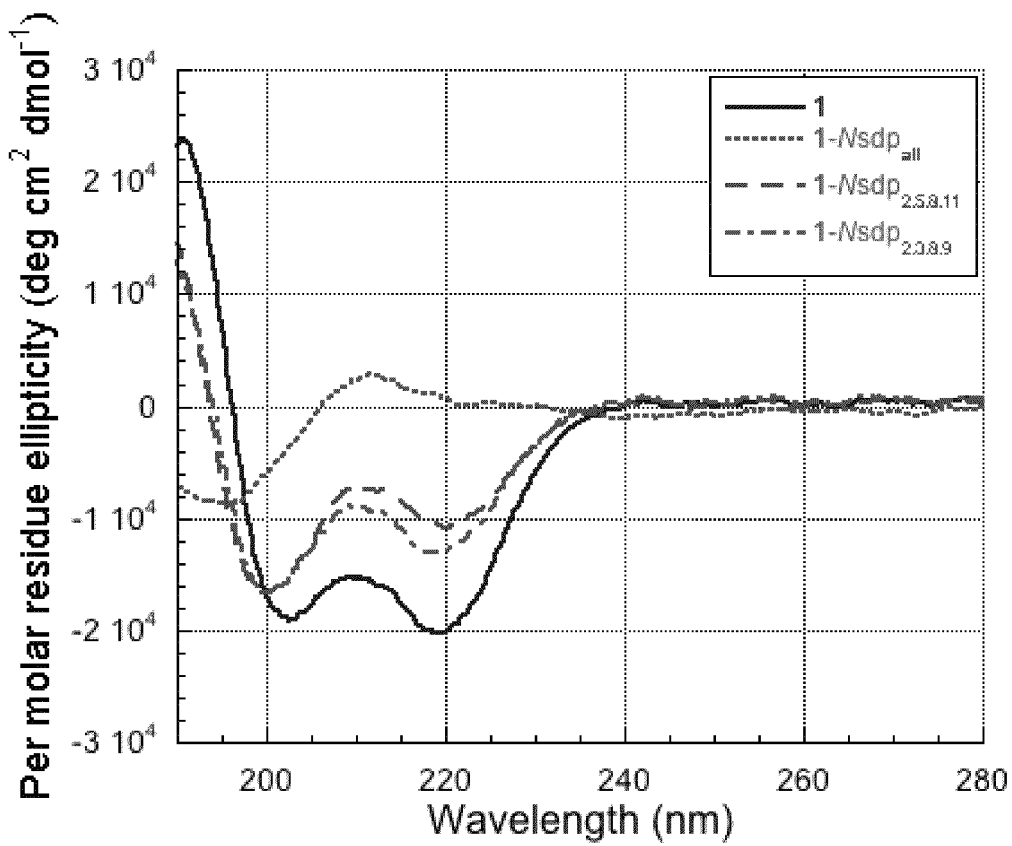

Figure 16B: 5mM POPE:CH
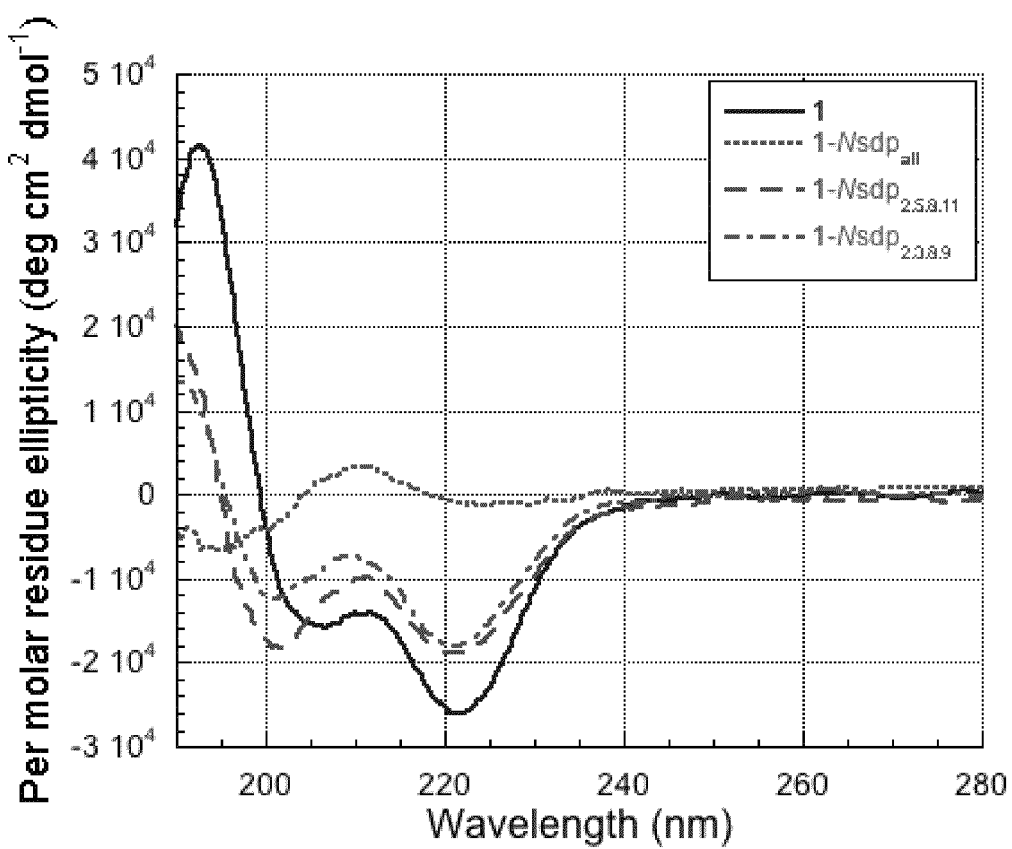

Figure 16C: 5mM POPE:POPG
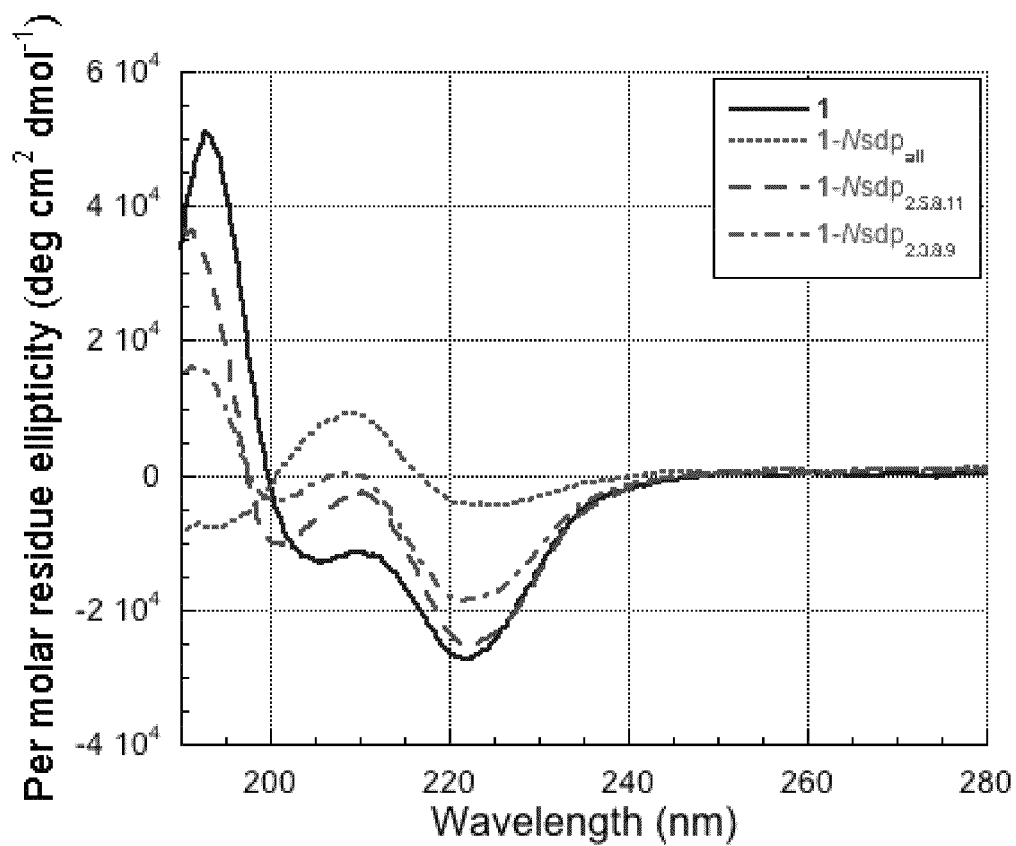

SELECTIVE POLY-N-SUBSTITUTED GLYCINE ANTIBIOTICS

This application claims priority benefit from application Ser. No. 61/065,189 filed Feb. 8, 2008, the entirety of which is incorporated herein by reference.

This invention was made with government support under Grant Nos. 1 R01HL67984 and AI007266 awarded by the National Institutes of Health and Contract No. DE-AC02-05CH$_{11231}$ awarded by the U.S. Department of Energy. The government has certain rights in the invention.

BACKGROUND OF THE INVENTION

Natural antimicrobial peptides (AMPs) defend a wide array of organisms against bacterial invaders and show potential as supplements for or replacements of conventional antibiotics, since few bacteria have evolved resistance to them. Many AMPs kill bacteria by permeabilization of the cytoplasmic membrane, causing depolarization, leakage, and death, whereas others target additional anionic bacterial constituents (e.g. DNA, RNA, or cell wall components). Bacterial resistance to AMPs is rare probably because they have evolved along with the resistance mechanisms designed to evade them; furthermore, the targets of many AMPs (e.g. bacterial plasma membranes, anionic intracellular macromolecules) are sufficiently general that changes to their sequence can be made that subvert resistance, yet have negligible impact on overall functionality.

Although AMPs have been actively studied for decades, they have yet to see widespread clinical use. This is in part due to the vulnerability of many peptide therapeutics to rapid in vivo degradation, which dramatically reduces their bioavailability. Non-natural mimics of AMPs can circumvent the proteolytic susceptibility of peptides while retaining their beneficial features. The short (<40 amino acids), simple structure of AMPs in the cationic, linear, α-helical class, which includes the well-known magainins, are especially amenable to mimicry. β-peptide mimics of these AMPs have been successfully created with antibacterial and non-hemolytic in vitro activity. Poly-N-substituted glycines (peptoids) comprise another class of peptidomimetics, and are isomers of peptides in that peptoid side chains are attached to the backbone amide nitrogen rather than to the α-carbon. More than any of the other peptidomimetic systems under study, including β-peptides, β-peptoids, oligoureas, and oligo (phenylene ethynylene)s, peptoids are particularly well-suited for AMP mimicry because they are easily synthesized on solid phase (using conventional peptide synthesis equipment) with access to diverse sequences at relatively low cost. By way of an elegant submonomer synthetic method, any chemical functionality available as a primary amine can be incorporated, whether it be an analog of a proteinogenic amino acid or a totally non-natural moiety; thus, peptoids are highly and finely tunable. Furthermore, they are protease-resistant, and can be designed to form amphipathic helices that resist thermal and chaotropic denaturation.

The poly-N-substituted glycine structure of peptoids precludes both backbone chirality and intrachain hydrogen bonding; nevertheless, peptoids can be driven to form stable helical secondary structures via periodic incorporation of bulky, α-chiral side chains. X-ray, NMR, and CD studies of peptoid oligomers have shown that incorporation of homochiral side chains can give rise to polyproline type-I-like helices with a periodicity of ~3 monomers per turn and a helical pitch of 6.0-6.7 Å. The three-fold periodicity of the peptoid helix facilitates the design of facially amphipathic structures similar to those formed by many AMPs; for example, the trimer repeat $(X-Y-Z)_n$ forms a peptoid helix with three faces, composed of X, Y, and Z residues, respectively.

Amphipathic secondary structures in which residues are segregated into hydrophobic and cationic regions are the hallmark of most AMPs. Regardless of their final target of killing, AMPs must interact with the bacterial cytoplasmic membrane, and amphipathicity is integral to such interactions. The cationic region facilitates electrostatically driven adsorption to anionic bacterial membranes and imparts some measure of selectivity, since mammalian cell membranes are largely zwitterionic. The hydrophobic region provides an additional driving force for incorporation of the AMP into the lipid bilayer. The precise nature of AMP-membrane interactions remains controversial and actively debated; a variety of mechanisms have been proposed, including the carpet, barrel-stave pore, toroidal pore, and aggregate models.

SUMMARY OF THE INVENTION

In light of the foregoing, it is an object of the present invention to provide new poly-N-substituted glycine compounds and methods for and/or therapies relating to their use as antibiotics, thereby improving upon the prior art and/or overcoming various deficiencies or shortcomings thereof. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide such compounds having minimum inhibitory concentrations in the low micromolar range against both Gram-positive and Gram-negative bacteria, with lower mammalian cytotoxicities and negligible hemolysis, at such concentrations, as compared to compounds of the prior art.

It can be another object of the present invention to provide such compounds, variable by residue sequence and/or N-substituent, so as to affect hydrophobicity and/or amphipathicity and/or to enhance selectivity.

It can be another object of the present invention alone or in conjunction with one or more of the preceding objectives, to provide a new class of N-alkylated peptoids, providing such potencies and selectivities at monomer numbers and peptoid lengths shorter than previously available.

Other objects, features, benefits and advantages of the present invention will be apparent from this summary and its descriptions of certain embodiments, and will be readily apparent to those skilled in the art having knowledge of various peptidomimetic compounds and their syntheses. Such objects, features, benefits and advantages will be apparent from the above as taken into conjunction with the accompanying examples, data, figures and all reasonable inferences to be drawn therefrom, alone or with consideration of the references incorporated herein.

In part, the present invention can be directed to a poly-N-substituted glycine antibiotic compound of a formula

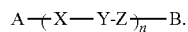

In such a compound, A can be selected from H and a terminal N-alkyl substituted glycine residue, where such an alkyl substituent can be selected from about $C_4$ to about $C_{20}$ linear, branched and cyclic alkyl moieties; n can be an integer selected from 1-3; B can be selected from $NH_2$, and one and two N-substituted glycine residues, such N-substituents as can be independently selected from α-amino acid side chain moieties and structural/functional analogs thereof; and X, Y and Z can also be independently selected from N-substituted glycine residues, such N-substituents as can be independently selected from α-amino acid side chain moieties and structural/functional analogs thereof and proline residues. As described elsewhere herein, such X-Y-Z periodicity can provide such a compound a certain amphipathicity. As would be understood by those skilled in the art made aware of this invention, such structural and/or functional analogy can be considered in the context of any such α-amino acid side chain, N-substituent and/or a sequence of such N-substituted glycine residues, such structure and/or function including but not limited to charge, chirality, hydrophobicity, amphipathicity, helical structure and facial organization. Such analogs include, without limitation, carbon homologs of such side chain—such homologs as would be understood in the art, including but not limited to plus or minus 1 or 2 or more methylene and/or methyl groups.

Regardless, in certain embodiments A can be H, and B can be selected from one or two N-substituted glycine residues, such a selection as can reduce the hydrophobicity of such a compound, as compared to compounds of 3-fold periodicity. In certain such embodiments, X can be an $N_{Lys}$ residue; n can be 2-3; and B can be two N-substituted glycine residues. Without limitation, such a compound can be of a formula

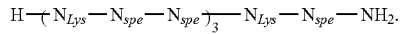

In various other embodiments, regardless of identity of A, X and B, at least one of Y and Z can be a proline residue. In certain such embodiments, X, Y and Z can be proline residues.

In certain other embodiments, A can be a terminal N-alkyl substituted glycine residue, with such an alkyl substituent as can be selected from about $C_6$ to about $C_{18}$ linear alkyl moieties. Regardless, B can be $NH_2$, and n can be selected from 1 and 2. In certain such embodiments, A can be a terminal N-alkyl substituted glycine residue, with an alkyl substituent selected from about $C_6$ to about $C_{18}$ linear alkyl moieties. Regardless, B can be an $N_{Lys}$ residue, and n can be 1.

In part, this invention can also be directed to a poly-N-substituted glycine antibiotic compound of a formula $$H-(N_{Lys}-Y-Z)_n-Y'-Z'-NH_2$$

wherein n can be selected from 2 and 3; and Y, Z, Y' and Z' can be independently selected from N-substituted glycine residues, where such substituents can be independently selected from α-amino acid side chain moieties and carbon homologs thereof. Such Y' and Z' residues can be selected to provide such compound reduced hydrophobicity as compared to a compound of 3-fold periodicity. In certain such embodiments, at least one of X and Y can be a proline residue. Regardless, n can be selected from 2 and 3, and Y' can be an $N_{Lys}$ residue. In certain such embodiments, one or both X and Y can be proline residues. Without limitation, such a compound with reduced hydrophobicity can be of a formula

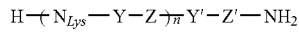

In part, this invention can also be directed to a poly-N-alkyl substituted glycine antibiotic compound of a formula $$H-N_R-(X-Y-Z)_n-B$$

wherein B can be selected from $NH_2$ and X'; X, Y, Z and X' can be independently selected from N-substituted glycine residues, where such substituents can be independently selected from α-amino acid side chain moieties and carbon homologs thereof; n can be an integer selected from 1 and 2; and R can be an N-alkyl substituent of such a glycine residue, as can be selected from about $C_4$ to about $C_{20}$ linear, branched and cyclic alkyl moieties. In certain embodiments, n can be 2, and B can be $NH_2$. In certain other embodiments, n can be 1, and B can be X'. Accordingly, one or both of X and X' can be $N_{Lys}$ residues. Regardless, an alkyl substituent can be selected from about $C_6$ to about $C_{18}$ linear, branched and cyclic alkyl moieties, and X and X' can be $N_{Lys}$ residues. Without limitation, such a compound can be of a formula

In part, the present invention can be directed to a poly-N-substituted glycine antibiotic compound comprising an N-terminus selected from H and an N-alkyl substituted glycine residue, where such an alkyl substituent can be selected from about $C_4$ to about $C_{20}$ linear, branched and cyclic alkyl moieties; a C-terminus selected from $NH_2$, one and two N-substituted glycine residues, such N-substituents as can be independently selected from α-amino acid side chain moieties and structural/functional analogs thereof; and 2 to about 15 monomeric residues between the N- and C-termini, each such residue as can be independently selected from proline residues and N-substituted glycine residues, said N-substituents independently selected from α-amino acid side chain moieties and structural/functional analogs thereof. As illustrated herein and as distinguished over the prior art, such monomers can be selected to provide such a compound a non-periodic sequence of monomers. As would be understood by those skilled in the art made aware of this invention, such structural and/or functional analogy can be considered in the context of any such α-amino acid side chain, N-substituent and/or a sequence of such N-substituted glycine residues, such structure and/or function including but not limited to charge, chirality, hydrophobicity, amphipathicity, helical structure and facial organization. Such analogs include, without limitation, carbon homologs of such side chain—such homologs as would be understood by those skilled in the art, including but not limited to plus or minus 1 or 2 or more methylene and/or methyl groups.

In certain embodiments, the N-terminus of such a compound can be H; and the C-terminus can be selected from said one and two N-substituted glycine residues. Regardless, such a compound can comprise 2 to about 5 (X-Y-Z) non-periodic trimers. In certain such embodiments, at least one of X, Y and Z in each of the trimers can be selected to interrupt 3-fold periodicity. Without limitation, at least one X in at least one said trimer can be an $N_{Lys}$ residue. In certain such embodiments, at least one of Y and Z in at least one such trimer can be a proline residue. In other embodiments, the monomeric residues can comprise at least two non-consecutive of the same or repeat trimers, with at least one such residue therebetween to interrupt periodicity. In certain such embodiments, at least one X in at least one such trimer can be an $N_{Lys}$ residue, and at least one of Y and Z in at least one said trimer can be a proline residue.

In various other non-limiting embodiments, the N-terminus of such a compound can be an N-alkyl substituted glycine residue, with an alkyl substituent selected from about $C_6$ to about $C_{18}$ linear alkyl moieties. Regardless, such a compound can comprise 2 to about 5 (X-Y-Z) non-periodic trimers. In certain such embodiments, at least one of X, Y and Z in each of the trimers can be selected to interrupt 3-fold periodicity. In certain other embodiments, the monomeric residues can comprise at least two non-consecutive of the same or repeat trimers, with at least one residue therebetween to interrupt peridicity. In certain such embodiments, at least one X in at least one said trimer can be an $N_{Lys}$ residue, and at least one of Y and Z in at least one said trimer can be a proline residue.

In part, the present invention can also be directed to one or more antimicrobial peptoid compositions comprising one or more of the poly-N-substituted glycine compounds of this invention. Such compounds as can optionally comprise one or more antimicrobial peptides and/or peptidomimetic compounds now or hereafter known in the art. Accordingly, this invention can be directed to a range of pharmaceutical compositions comprising one or more of the present polypeptoid/ ampetoid compounds, optionally with an antimicrobial component of the prior art, and a pharmaceutically-acceptable carrier. Such compositions can be prepared and/or formulated as would be understood by those skilled in the art made aware of this invention. Regardless, as illustrated below, any of the present polypeptoid/ampetoid compounds and/or related compositions can be used alone or in combination, whether administered together or sequentially, in conjunction with one or more bacteria or microbial treatment methodologies. Without limitation, such a method can comprise providing one or more such poly-N-substituted glycine compounds and/ or related compositions; and administering such compound(s)/composition(s) and/or contacting bacteria therewith. As would be understood by those skilled in the art, such administration can be in vitro or in vivo, using techniques of the sort described herein or straight-forward modifications thereof, such modifications as would also be known to those skilled in the art and made aware of this invention.

BRIEF DESCRIPTION OF THE DRAWINGS

FIGS. 6A-C. X-ray reflectivity data (A) and corresponding fit for DPPG monolayer before (circles; cartoon inset, top (B)) and after (squares; cartoon inset, bottom (C)) peptoid 1 was injected into the subphase beneath the monolayer.

FIGS. 10A-C: CD spectra of ampetoid register and sequence variants. Ampetoid concentrations were 60 μM. (A) CD in 10 mM Tris buffer (pH 7.4). (B) CD spectra in 10 mM Tris buffer with 5 mM erythrocyte-mimetic POPC:cholesterol (2:1) SUVs. (C) CD in 10 mM Tris buffer with 5 mM bacteria-mimetic POPE:PEPG (3:7) SUVs.

FIGS. 11A-B: CD spectra of net charge variants in (A) 10 mM Tris buffer and (B) same buffer with 5 mM POPC/ cholesterol 2:1 SUVs. Ampetoid concentration is 60 μM.

FIGS. 12A-C: CD spectra of length variants in (A) 10 mM Tris buffer and (B) same buffer with 5 mM POPC/cholesterol 2:1 SUVs and (C) same buffer with 5 mM POPE/POPG 3:7 SUVs. Ampetoid concentration is 60 μM.

FIGS. 13A-C: CD spectra of proline variants in (A) 10 mM Tris buffer and (B) same buffer with 5 mM POPC/cholesterol 2:1 SUVs and (C) same buffer with 5 mM POPE/POPG 3:7 SUVs. Ampetoid concentration is 60 μM.

FIGS. 14A-C: CD spectra of ampetoids containing achiral monomers in (A) 10 mM Tris buffer and (B) same buffer with 5 mM POPC/cholesterol 2:1 SUVs and (C) same buffer with 5 mM POPE/POPG 3:7 SUVs. Ampetoid concentration was 60 μM.

FIGS. 15A-C: CD spectra of ampetoids containing opposite chirality monomers in (A) 10 mM Tris buffer and (B) same buffer with 5 mM POPC/cholesterol 2:1 SUVs and (C) same buffer with 5 mM POPE/POPG 3:7 SUVs. Ampetoid concentration was 60 μM.

FIGS. 16A-C: CD spectra of ampetoids containing aliphatic monomers in (A) 10 mM Tris buffer and (B) same buffer with 5 mM POPC/cholesterol 2:1 SUVs and (C) same buffer with 5 mM POPE/POPG 3:7 SUVs. Ampetoid concentration was 60 μM.

DETAILED DESCRIPTION OF CERTAIN EMBODIMENTS

Figure 1:
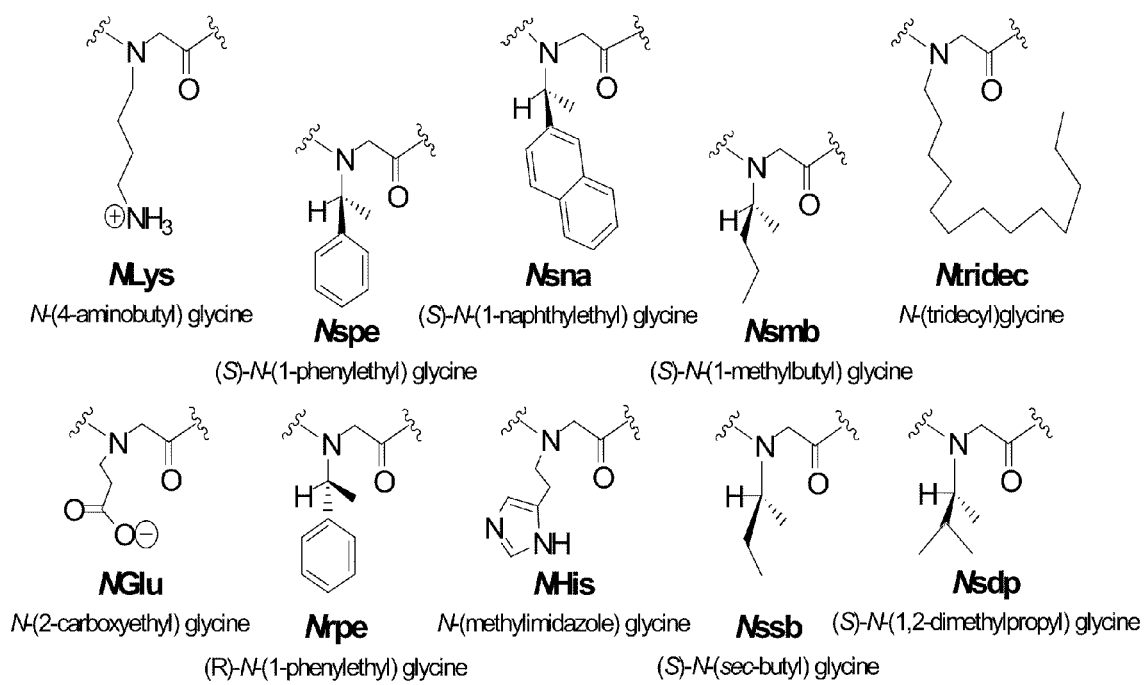
FIG. 1. Peptoid monomer side chain structures, with full and shorthand names.

As illustrated, the present invention provides a class of helical, cationic, amphipathic, sequence- and/or length-specific poly-N-substituted glycines (peptoids) with potent and very selective antibacterial activity. These molecules demonstrate broad-spectrum antimicrobial activity against a range of pathogens, and are able to effectively treat a bacterial infection in vivo. It has been demonstrated that these peptoids are both structurally and functionally analogous to antimicrobial peptides (AMPs), the natural molecules. Moreover, by modulating the sequence and side chain functionality, the activity and selectivity of antimicrobial peptoids can be tuned. Some compounds have minimum inhibitory concentrations (MICs) in the low micromolar range against Gram-positive and Gram-negative bacteria, with low mammalian cytotoxicity and negligible (<1%) hemolysis at their MICs. These activities are substantially improved over previous antibacterial peptides earlier reported, the best of which were much more hemolytic toward human red blood cells. This invention also provides a new class of alkylated antibacterial peptoids, which retain the antimicrobial potency and selectivity in analogs as short as 5 monomers in length.

With reference to examples 1-9 and FIGS. 1-8, below, peptoids were synthesized, as widely-known in the art, using the submonomer synthetic method described by Zuckermann et al., purified using reverse-phase high performance liquid chromatography (RP-HPLC), and characterized with electrospray ionization mass spectrometry (ESI-MS) and circular dichroism (CD) spectroscopy. (See, Zuckermann, R. N., Kerr, J. M., Kent, S. B. H., & Moos, W. H. (1992) *J. Am. Chem. Soc.*, 114, 10646-10647, the entirety of which is incorporated herein by reference.) CD spectrum of antimicrobial peptoids confirms that they adopt helical structures in both aqueous buffer and lipid vesicles, such that they possess a facially amphipathic organization of cationic and hydrophobic residues. Antibacterial activity was determined according to Clinical Laboratory Standards Institute (CLSI) protocols for broth microdilution, and hemolytic activity determined using similar microdilution methods. The effect of peptoids on cellular metabolic activity was determined using the colorimetric tetrazolium salt-based MTS [3-(4,5-dimethylthiazol-2-yl)-5-(3-carboxymethoxyphenyl)-2-(4-sulfophenyl)-2H-tetrazolium] assay also using serial microdilution. These data demonstrate broad-spectrum activity against a variety of clinically relevant pathogens, yet the most selective antimicrobial peptides do not harm human red blood cells or mammalian fibroblast cells at concentrations many times their antibacterial concentrations. Lastly, the ability of two peptoids to treat an infection in vivo using a murine peritoneal injection model was evaluated. These results show that peptoids can significantly reduce the bacterial counts in the mouse peritoneal cavity over a 24 hour exposure period without mouse fatality.

Structure-activity studies of antimicrobial peptoids suggest close analogy between their mechanisms of bacterial killing and those of AMPs. Numerous studies of AMPs have found that, in general, increases in hydrophobicity and amphipathicity and decreases in net charge can bias a peptide toward a less selective mechanism. The converse is true, in that adding cationic charge, and decreasing hydrophobicity or amphipathicity can lead to a more selective peptide. The structure-activity studies conducted show that peptoids respond similarly to changes in physicochemical properties. That is, selective peptoids become less selective when their sequences are altered to make them more hydrophobic, more amphipathic, or less cationic, and vice versa. Antimicrobial peptoids are thus functional analogs of AMPs.

Specular X-ray reflectivity was used to examine molecular-level interactions of antimicrobial peptoids with lipids. Just as selective AMPs spend the majority of their time oriented parallel to the plane of the membrane surface, antimicrobial peptoids are oriented in anionic DPPG monolayers with 56° between the surface normal and the long axis of the peptide—clearly not perpendicular to the membrane, which would be expected for a transmembrane pore-forming peptide—with clear interactions between the peptoid and the lipid headgroups. The similar lipid-bound orientations of AMPs and antimicrobial peptoids further suggests mechanistic analogy between the two classes of molecules.

The present invention, therefore, provides a novel class of antibiotics which offers a combination of several desirable properties, including but not limited to: 1. Efficacy in reducing bacterial counts in a mammalian system over a 24-hour exposure using an intraperitoneal injection mouse model. 2. low-micromolar antibacterial activity against a broad spectrum of clinically relevant pathogens; 3. selectivity that is tunable by molecular sequence characteristics, whereby mammalian cells are not harmed at the compounds' MICs; 4. functional analogy to natural antimicrobial peptides, which implies that, like AMPs, antimicrobial peptoids are not readily susceptible to the development of bacterial resistance.

The role of hydrophobicity is articulated by studies of antimicrobial lipopeptides, such as polymyxin B and trichogin. These AMPs are composed of a peptide chain with a fatty acid tail at the N-terminus. For example, the deacylated version of polymyxin B is much less bactericidal than the natural lipopeptide. Also, trichogin analogues with varying lengths of lipids showed greater activity with longer tails, and analogues with tails shorter than four carbon atoms were found to be inactive. Attachment of fatty tails to AMPs that are not normally acylated has also been attempted, and in some cases, alkylation of inactive cationic peptides was sufficient to endow the resulting lipopeptides with antibacterial or antifungal activity. Furthermore, studies by Shai et al. have found that when varying the length of an alkyl tail, a threshold of hydrophobicity is reached at which the peptide is no longer selective. That is, at a point, increasing tail length only increases hemolytic activity without improving antibacterial activity.

As illustrated herein, the in vitro activities of simple peptoid mimics of AMPs are strikingly similar to those of AMPs themselves. (See, e.g., Table 1.) Certain antimicrobial peptoids ("ampetoids") exhibit broad-spectrum antimicrobial activity, low hemolysis, minimal effects on mammalian cellular metabolism, and efficacy at treating an infection in vivo. Furthermore, conjugation of fatty tails to peptoids can lead to selective, non-natural analogs of AMPs as short as five monomers in length that are potent against both bacteria and fungi. Structure-activity relationships observed in a library of rationally designed ampetoids are wholly analogous to those which describe many AMPs. Using synchrotron radiation to probe the interactions between ampetoids and lipid layers, AMP-ampetoid analogy was found to extend to molecular-level interactions.

TABLE 1

Antibacterial and hemolytic activities of ampetoids and AMPs. Peptoids monomer abbreviations are explained in FIG. 2. For minimum inhibitory concentrations (MICs) and hemolytic doses (HDs) reported as "> x", x = 200 µg/mL - the highest concentration tested (except for pexiganan, which was tested up to 500 µg/mL).

| Variant class | Shorthand name | Sequence | HPLC elution solvent* |
|---|---|---|---|
| Basis | 1 | H-(Nlys-Nspe-Nspe)$_4$-NH$_2$ | 48% |
|  | 2 | H-(Nlys-Nssb-Nspe)$_4$-NH$_2$ | 39% |
| Chirality | 1$_{enantiomer}$ | H-(Nlys-Nrpe-Nrpe)$_4$-NH$_2$ | 48% |
| Length | 1$_{6mer}$ | H-(Nlys-Nspe-Nspe)$_2$-NH$_2$ | 41% |
|  | 1$_{9mer}$ | H-(Nlys-Nspe-Nspe)$_3$-NH$_2$ | 46% |
|  | 1$_{15mer}$ | H-(Nlys-Nspe-Nspe)$_5$-NH$_2$ | 51% |
| Hydrophobicity | 2-Nsap$_{2,5,8,11}$ | H-(Nlys-Nsap-Nspe)$_4$-NH$_2$ | 48% |
|  | 2-Nsna$_{6,12}$ | H-(Nlys-Nssb-Nspe-Nlys-Nssb-Nsna)$_2$-NH$_2$ | 47% |
|  | 1-Nsna$_{6,12}$ | H-(Nlys-Nspe-Nspe-Nlys-Nspe-Nsna)$_2$-NH$_2$ | 53% |
|  | 1-Nhis$_{6,12}$ | H-(Nlys-Nspe-Nspe-Nlys-Nspe-Nhis)$_2$-NH$_2$ | 37% |
|  | 1-Pro$_6$ | H-Nlys-Nspe-Nspe-Nlys-Nspe-L-Pro-(Nlys-Nspe-Nspe)$_2$-NH$_2$ | 40% |
| Charge | 1-Nglu$_{4,10}$ | H-(Nlys-Nspe-Nspe-Nglu-Nspe-Nspe)$_2$-NH$_2$ | 60%† |
|  | 1-Nglu$_{1,4,7,10}$ | H-(Nglu-Nspe-Nspe)$_4$-NH$_2$ | 54%† |
| Amphipathicity | 1$_{block}$ | H-(Nlys)$_4$-(Nspe)$_8$-NH$_2$ | 54% |
|  | 2$_{scrambled}$ | H-Nlys-Nssb-Nspe-Nssb-Nspe-Nlys-Nspe-Nlys-Nssb-Nssb-Nspe-Nlys-NH$_2$ | 42% |

TABLE 1-continued

Antibacterial and hemolytic activities of ampetoids and AMPs. Peptoids monomer abbreviations are explained in FIG. 2. For minimum inhibitory concentrations (MICs) and hemolytic doses (HDs) reported as "> x", x = 200 µg/mL - the highest concentration tested (except for pexiganan, which was tested up to 500 µg/mL).

| AMPs | | | |
|---|---|---|---|
| pexiganan[1] | GIGKFLKKAKKFGKAFVKIL KK (SEQ ID NO: 1)-NH$_2$ | | 38% |
| melittin[5] | GIGAVLKVLTTGLPALISWIK RKRQQ (SEQ ID NO: 2)-NH$_2$ | | 54% |

| E. coli MIC (µM) | B. subtilis MIC (µM) | HD$_{10}$/HD$_{50}$ (µM) | Selectivity ratio (SR)[‡] |
|---|---|---|---|
| 3.5 | 0.88 | 21/100 | 6.0 |
| 31 | 3.9 | >120/>120 | >3.9 |
| 3.5 | 0.88 | 16/86 | 4.6 |
| 27 | 27 | >220/>220 | >8.1 |
| 9.1 | 1.2 | >150/>150 | >16 |
| 5.5 | 1.4 | 3/19 | 0.55 |
| 7.4 | 0.95 | >120/>120 | >16 |
| 7.2 | 0.93 | 55/>120 | 7.6 |
| 3.3 | 1.6 | 4/22 | 1.2 |
| 3.5 | 6.9 | >110/>110 | >31 |
| 3.1 | 1.6 | 63/>110 | 20 |
| >110 | 6.9 | 19/40 | <0.17 |
| >219 | >219 | >110/>110 | N/A |
| 6.9 | 1.7 | 18/73 | 2.6 |
| 31 | 15 | >120/>120 | >3.9 |
| 3.1 | 1.6 | 73/>200 | 24 |
| 1.6 | 0.78 | 2/6 | 1.3 |

*Percent acetonitrile in water, 0.1% (v/v) trifluoroacetic acid (TFA) at HPLC elution.
[†]With 10 mM ammonium acetate and no TFA, pH 7.0.
[‡]Selectivity ratio, SR = (HD$_{10}$)/(E. coli MIC).
[§]For concentrations reported as "> x", x = 200 µg/mL-the highest concentration tested (except for pexiganan, which was tested up to 500 µg/mL).

Initial Antibacterial Activity and Selectivity Screening

An initial set of 15 ampetoid analogs was synthesized to determine whether peptoids are affected by structural and sequence modifications in a manner consistent with AMP activities. The designs for ampetoids in this library were derived from two antibacterial and selective amphipathic dodecamers, 1 and 2. Peptoid 1 [H-(Nlys-Nspe-Nspe)$_4$-NH$_2$] is composed of ⅔ Nspe, the peptoid analog of phenylalanine, and ⅓ Nlys, the peptoid analog of lysine (see FIG. 1 for the structures of representative peptoid monomers and corresponding N-substituents). Peptoid 2 [H-(Nlys-Nssb-Nspe)$_4$-NH$_2$] contains ⅓ isoleucine-like Nssb monomers in place of Nspe. The variant sequences were designed to effect changes in chirality, length, hydrophobicity, charge, and amphipathicity. All of these compounds were tested for antibacterial activity against representative BSL1 Gram-negative (E. coli JM109) and Gram-positive (B. subtilis BR151) bacterial strains. As an initial measure of selectivity, the lytic activity of the peptoids was determined against human erythrocytes. Table 1 summarizes the sequences synthesized, the solvent composition at RP-HPLC elution as a relative measure of molecular hydrophobicity, and antibacterial and hemolytic activities. Ten of the 15 peptoids exhibit low-micromolar MICs against both E. coli and B. subtilis, demonstrating that non-natural peptoid oligomers can be as active as AMPs (MICs for pexiganan—a selective AMP analog of magainin-2—and the bee-venom AMP melittin are shown in Table 1).

A selectivity ratio (SR) for each compound was defined, also shown in Table 1, as the quotient of the 10% hemolytic dose (HD$_{10}$) and the E. coli MIC. Thus, the SR is an estimate of an ampetoid's tendency to kill bacteria rather than mammalian cells. Ampetoid 1 has an SR of 6.0, similar to that of pexiganan (SR=5.8). As expected, melittin (well known to be cytotoxic) has a low SR of 0.16. Most AMPs have antibacterial activities in the low-micromolar range; since peptoid 1 has MICs in that range, the ampetoid library was primarily expected to yield variants with increased selectivity. Indeed, six of 13 variants are more selective than 1 and pexiganan (i.e. SRs>6).

Figure 2:
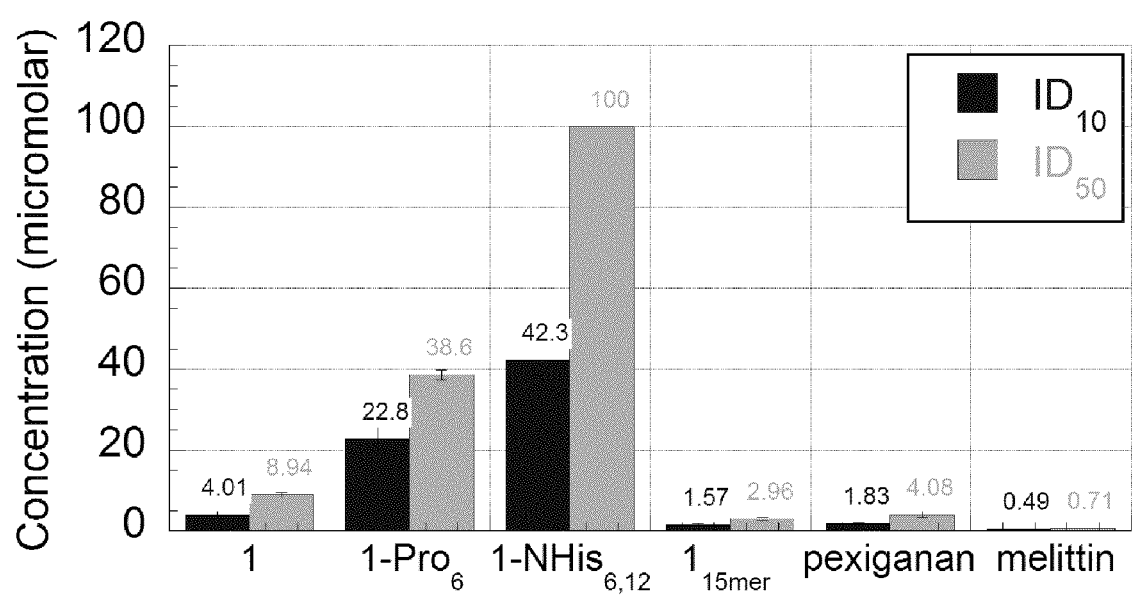
FIG. 2. Cytotoxicity data for selected peptoids and comparator peptides against A549 lung epithelial cells.
Figure 3:
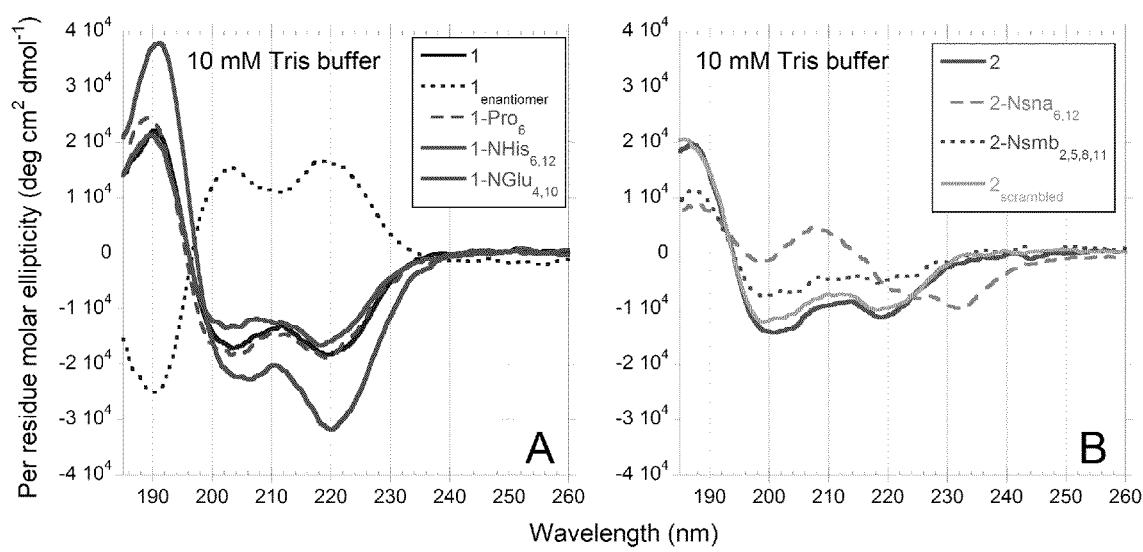
FIGS. 3A-B. CD spectra of (A) variants of 1 and (B) variants of 2 in 10 mM Tris buffer, pH 7.4.

The biocompatibility of selected oligomers with A549 lung epithelial cells was evaluated using the MTS [3-(4,5-dimethylthiazol-2-yl)-5-(3-carboxymethoxyphenyl)-2-(4-sulfophenyl)-2H-tetrazolium] assay. FIG. 2 shows that the 10% metabolic inhibitory dose (ID$_{10}$) and 50% inhibitory dose (ID$_{50}$) of these selected peptoids compare very favorably to that of pexiganan and melittin; ampetoids 1-Pro$_6$ and 1-Nhis$_{6,12}$, with MICs<7 µM, have ID$_{10}$'s that are 10 and 20 times that of pexiganan. Interestingly, the relatively non-selective peptoid 1$_{15mer}$ exhibits cytotoxicity no worse than pexiganan.

Structure-activity relationships derived from a library of ampetoids are discussed below according to the primary physicochemical parameter that was altered. As in previous studies, circular dichroism (CD) spectroscopy was used to compare the helicities of the ampetoids by monitoring the intensity of spectral extrema, particularly at 190 and 220 nm. CD was performed in 10 mM aqueous Tris buffer, pH 7.4, alone and in the presence of two types of small unilamellar vesicles (SUVs) composed of model binary lipid mixtures: (1) anionic E. coli membrane-mimetic SUVs [POPE/POPG (7:3 mole ratio)], and (2) zwitterionic erythrocyte membrane-mimetic SUVs [POPC/cholesterol (CH) (1:1 mole ratio)].

With regard to chirality, using enantiomeric side chains (Nrpe in place of Nspe; FIG. 1), a left-handed helical analog of peptoid 1 was created, called 1$_{enantiomer}$, as evidenced by its mirror-image CD spectrum in comparison to that of 1 (FIG. 3A). The activities and selectivities of 1 and 1$_{enantiomer}$ are congruent (Table 1).

With regard to length, variants of 1 were created, ranging from 6 to 15 monomers, all with the same three-fold sequence repeat and 1:3 charge-to-length ratio. The shortened variants of 1, 1$_{6mer}$ and 1$_{9mer}$ (approx. 12 Å and 18 Å in length, respectively), are both active antimicrobials and are more selective than 1 (Table 1). In contrast, the lengthened variant of 1, 1$_{15mer}$ (approx. 30 Å in length), is substantially more hemolytic (SR=0.55) and cytotoxic (FIG. 2) than 1, and slightly less antibacterial. The helicities of these compounds in buffer are congruent (data not shown).

Hydrophobicity was modulated independently of length by replacing hydrophobic Ile-like Nssb and Phe-like Nspe monomers in 1 and 2 with bulkier and more hydrophobic Nsmb and Nsna, respectively (FIG. 1). The heightened molecular hydrophobicity of 2-Nsmb$_{2,5,8,11}$ and 2-Nsna$_{6,12}$ led to increases in both antibacterial and hemolytic activities (Table 1). 1-Nsna$_{6,12}$, however, shows no enhancement of antibacterial activity relative to 1, but is much more hemolytic (SR=1.2).

Two variants of 1 with reduced hydrophobicity were also created. Two evenly spaced hydrophobic Nspe residues in 1 were replaced by Nhis, an achiral peptoid monomer analog of histidine (FIG. 1) that is polar yet predominantly uncharged at physiological pH, yielding 1-Nhis$_{6,12}$. This oligomer exhibits substantially decreased hemolysis (SR>31; Table 1) and decreased cytotoxicity (FIG. 2), with only a slight reduction in antibacterial activity against B. subtilis compared to 1. A second reduced-hydrophobicity variant, 1-Pro$_6$, was created by replacing the Nspe at position 6 with 1-proline. Although proline is well known to destabilize peptide α-helices, 1-Pro$_6$ and 1 are similarly helical in buffer (FIG. 3A) since 1-proline is well-accommodated in right-handed type-1-polyproline-like peptoid helices. 1-Pro$_6$ (SR=8.9) exhibits less hemolysis and less cytotoxicity than 1, with similar antibacterial activity (Table 1, FIG. 2).

With respect to charge, the majority of AMPs are cationic, and replacement of their basic residues with uncharged or anionic moieties typically leads to a loss of antibacterial activity. To investigate this phenomenon in ampetoids, Nlys monomers in 1 were substituted with glutamate-like Nglu (FIG. 1) to create 1-Nglu$_{4,10}$ and 1-Nglu$_{1,4,7,10}$. Zwitterionic 1-Nglu$_{4,10}$ has significantly reduced activity against *B. subtilis* compared to 1 and is inactive against *E. coli* (Table 1), likely due to the absence of favorable electrostatic interactions with anionic bacterial membranes; however, it is quite hemolytic (SR<0.17). The fully anionic variant, 1-Nglu$_{1,4,7,10}$ is devoid of both antibacterial and hemolytic activity.

To study amphipathicity, a terminally, rather than facially, amphipathic isomer of 1 with block-like architecture ($1_{block}$) was created, as well as a scrambled sequence of 2 designed to preclude global amphipathicity ($2_{scrambled}$) (Table 1). The terminal segregation of cationic and hydrophobic residues in the $1_{block}$ sequence ensures a strongly amphipathic structure independent of the facial organization of residues along a helix. $1_{block}$ is slightly less antibacterial and more hemolytic than 1 (SR=2.6), although it has the same monomer composition. The CD spectra of $2_{scrambled}$ in buffer and lipid environments (FIGS. 3B, 4B, 5B) are nearly congruent to those of 2, suggesting $2_{scrambled}$ forms a structured helix which, due to its scrambled sequence, has low global amphipathicity relative to 2. Peptoid $2_{scrambled}$ exhibits antibacterial activity, but no hemolysis up to 120 μM.

systematically varying both the alkyl tail length and the length of the peptoid chain. In general, the length of the peptoid chain was decreased in increments 3 monomers (one full helical turn) from the original sequence of 1. However, based on the report of active ultrashort AMPs containing two positive charges, an additional Nlys monomer was retained at the shortest length. Alkyl tails were incorporated via the sub-monomer peptoid synthetic protocol (using the appropriate alkylamine for the substitution step) as the side chain of the N-terminal peptoid residue. All peptoids were amidated at the C-terminus. Table 2 lists the shorthand names and sequences of the alkylated peptoids investigated, as well as the activities of these alkylated variants. Interestingly, it should be noted that C13-1$_{4mer}$—a compound roughly half the molecular weight of 1—exhibited antibacterial activity comparable to 1 and was in fact found to be more selective against erythrocytes.

Additionally, in order to characterize possible antifungal activity, a library of alkylated compounds was tested against *C. albicans*, a representative fungal strain. In several instances, compounds such as C10-1$_{6mer}$ and C13-1$_{4mer}$ were found to have potent and selective antifungal activity.

Whereas the preceding generation of molecules was designed to elucidate structure function relationships of specific molecular parameters (chirality, length, hydrophobicity, etc.), another generation compounds were designed explicitly to explore effects on selectivity. Antimicrobial activity of these compounds was tested against bacterial strains *E. coli* (ATTC 35218) and *B. subtilis* (ATTC 6633) in cation-adjusted MHB using the microdilution protocols previously described. The sequences, antimicrobial activities, hemolytic activities, and metabolic inhibitory concentrations against NIH 3T3 mouse fibroblast cells are summarized in Table 3 and the rationale of their design is described below.

TABLE 2

Antibacterial, antifungal, and hemolytic activities of alkylated variants of peptoid 1. See FIG. 1 for a guide to monomer structures.

| PEPTOID | SEQUENCE | HPLC ELUTION† | E. coli MIC (μM) | B. subtilis MIC (μM) | C. albicans MIC (μM) | HD$_{10}$/HD$_{50}$ (μM) |
|---|---|---|---|---|---|---|
| 1 | H-(Nlys-Nspe-Nspe)$_4$-NH$_2$ | 48% | 6.3 | 1.6 | 6.3 | 18/72 |
| C5-1 | H-Npent-(Nlys-Nspe-Nspe)$_4$-NH$_2$ | 51% | 6.3 | 1.6 | 6.3 | 10/40 |
| C10-1 | H-Ndec-(Nlys-Nspe-Nspe)$_4$-NH$_2$ | 58% | 12.5 | 1.6 | 1.6 | 8/27 |
| 1$_{9mer}$ | H-(Nlys-Nspe-Nspe)$_3$-NH$_2$ | 46% | 25 | 1.6 | 15.6 | 150/>200 |
| C5-1$_{9mer}$ | H-Npent-(Nlys-Nspe-Nspe)$_3$-NH$_2$ | 48% | 16.3 | 1.0 | 12.5 | 65/>200 |
| C10-1$_{9mer}$ | H-Ndec-(Nlys-Nspe-Nspe)$_3$-NH$_2$ | 59% | 6.3 | 3.1 | 3.1 | 12/40 |
| 1$_{6mer}$ | H-(Nlys-Nspe-Nspe)$_2$-NH$_2$ | 47% | 27* | 27* | >100 | >220/>220 |
| C5-1$_{6mer}$ | H-Npent-(Nlys-Nspe-Nspe)$_2$-NH$_2$ | 49% | >200 | 3.1 | 100 | >200/>200 |
| C10-1$_{6mer}$ | H-Ndec-(Nlys-Nspe-Nspe)$_2$-NH$_2$ | 59% | 6.3 | 1.6 | 6.25 | 30/80 |
| C10-1$_{4mer}$ | H-Ndec-Nlys-Nspe-Nspe-Nlys-NH$_2$ | 50% | >100 | 6.3 | 100 | >200/>200 |
| C13-1$_{4mer}$ | H-Ntridec-Nlys-Nspe-Nspe-Nlys-NH$_2$ | 57% | 12.5 | 1.6 | 12.5 | 70/200 |
| Pexiganan | GIGKFLKKAKKFGKAFVKILKK (SEQ ID NO: 1)-NH$_2$ | 38% | 12.5 | 1.6 | 50 | 70/>200 |

*All assays were performed in cation-adjusted broth except where denoted by an asterisk.
†HPLC elution is given as a measure of hydrophobicity and defined as percent acetonitrile in H$_2$O (C18 column, conducted in the presence of 0.1% TFA, pH 1).

In order to test the effects of alkylation on antimicrobial peptoids, a series of alkylated variants of 1 was synthesized,

TABLE 3

Sequences and activities of second-generation peptoids designed to explore selectivity.

| Variant class | Shorthand name | Sequence |
|---|---|---|
| Basis | 1 | H-(Nlys-Nspe-Nspe)$_4$-NH$_2$ |
| Register variants | 1B | H-(Nspe-Nlys-Nspe)$_4$-NH$_2$ |
|  | 1C | H-(Nspe-Nspe-Nlys)$_4$-NH$_2$ |
| Proline variants | 1-Pro$_3$ | H-(Nlys-Nspe-L-Pro)-(Nlys-Nspe-Nspe)$_3$-NH$_2$ |
|  | 1-Pro$_6$ | H-Nlys-Nspe-Nspe-Nlys-Nspe-L-Pro-(Nlys-Nspe-Nspe)$_2$-NH$_2$ |
|  | 1-Pro$_9$ | H-(Nlys-Nspe-Nspe)$_2$-Nlys-Nspe-L-Pro-Nlys-Nspe-Nspe-NH$_2$ |
|  | 1-Pro$_{3,9}$ | H-Nlys-Nspe-L-Pro-Nlys-Nspe-Nspe-Nlys-Nspe-L-Pro-Nlys-Nspe-Nspe-NH$_2$ |
| Nhis variants | 1-Nhis$_6$ | H-Nlys-Nspe-Nspe-Nlys-Nspe-Nhis-(Nlys-Nspe-Nspe)$_2$-NH$_2$ |
|  | 1-Nhis$_{6,12}$ | H-(Nlys-Nspe-Nspe-Nlys-Nspe-Nhis)$_2$-NH$_2$ |
|  | 1-Nhis$_{3,6,9,12}$ | H-(Nlys-Nspe-Nhis)$_3$-NH$_2$ |
| Achiral variants | 1$_{achiral}$ | H-(Nlys-Npm-Npm)$_4$-NH$_2$ |
|  | 1$_{achiral}$-Nspe$_{12}$ | H-(Nlys-Npm-Npm)$_3$-Nlys-Npm-Nspe-NH$_2$ |
|  | 1-Npm$_{2,5,8,11}$ | H-(Nlys-Npm-Nspe)$_4$-NH$_2$ |
|  | 1-Npm$_{2,3,8,9}$ | H-(Nlys-Npm-Npm-Nlys-Nspe-Nspe)$_2$-NH$_2$ |

TABLE 3-continued

Sequences and activities of second-generation peptoids designed to explore selectivity.

| Nsdp variants | 1-Nsdp$_{all}$ | H-(Nlys-*N*smb-*N*smb)$_4$-NH$_2$ |
|---|---|---|
| | 1-Nsdp$_{2,5,8,11}$ | H-(Nlys-*N*smb-Nspe)$_4$-NH$_2$ |
| Charge distribution variants | 1-Nlys$_{5,11}$ | H-(Nlys-Nspe-Nspe-Nlys-*N*lys-Nspe)$_2$-NH$_2$ |
| | 1B$_{12mer}$-Nlys$_{4,10}$ | H-(Nspe-Nlys-Nspe-*N*lys-Nlys-Nspe)$_2$-NH$_2$ |
| | 1B$_{15mer}$-Nlys$_{4,10}$ | H-(Nspe-Nlys-Nspe-Nlys-*N*lys-Nspe)$_2$-Nspe-Nlys-Nspe-NH$_2$ |
| | 1B$_{12mer}$-Nlys$_{4,6,10}$ | H-Nspe-Nlys-Nspe-*N*lys-Nlys-*N*lys-Nspe-Nlys-Nspe-*N*lys-Nlys-Nspe-NH$_2$ |
| | 1B$_{15mer}$-Nlys$_{4,6,10}$ | H-Nspe-Nlys-Nspe-*N*lys-Nlys-*N*lys-Nspe-Nlys-Nspe-*N*lys-Nlys-Nspe-Nspe-*N*lys-Nspe-NH$_2$ |
| AMP comparator | pexiganan | GIGKFLKKAKKFGKAFVKILKK (SEQ ID NO: 1)-NH$_2$ |

| E. coli MIC (µM) | B. subtilis MIC (µM) | HD$_{10}$/HD$_{50}$ (µM) | ID$_{10}$/ID$_{50}$‡ |
|---|---|---|---|
| 6.3 | 1.6 | 21/100 | 5.1/1.4 |
| 6.3 | 1.6 | 40/>100 | 4.9/2.5 |
| 6.3 | 1.6 | 25/>100 | 5.6/2.3 |
| 12.5 | 1.6 | 74/>200 | 4.8/12 |
| 12.5 | 1.6 | 83/>200 | 8.2/18 |
| 12.5 | 1.6 | 165/>200 | 9.8/24 |
| 50 | 1.6 | >200/>200 | 31/71 |
| 25 | 1.6 | 170/>200 | — |
| >50 | 1.6 | >110/>110 | >100/>100 |
| >100 | 100 | >200/>200 | 72/>100 |
| — | — | >100/>100 | 5.1/16 |
| 25 | 1.6 | 164/>200 | — |
| 6.3 | 1.6 | 87/>200 | 3.5/6.8 |
| 6.3 | 1.6 | 68/>200 | — |
| 50 | 0.78 | >200/>200 | 6.6/64 |
| 12.5 | 0.78 | 111/>200 | 10/20 |
| 50 | 1.6 | >100/>100 | 23/85 |
| 50 | 0.78 | >200/>200 | — |
| 50 | 0.78 | >200/>200 | — |
| >100 | 1.6 | >200/>200 | — |
| >100 | 0.78 | >200/>200 | — |
| 12.5 | 1.6 | 70/>200 | 1.9/9 |

Without limitation, two molecules in Table 1 found to be extraordinary selective (1-Pro$_6$ and 1-Nhis$_{6,12}$) were used to derive several new sequences. Since 1-Pro$_6$ was found to be highly antimicrobial but less hemolytic than 1, two isomerically related compounds (1-Pro$_3$, 1-Pro$_9$) were created to explore the effect of proline residue position on activity and selectivity. One variant with prolines in both the third and ninth position (1-Pro$_{3,9}$) was also designed to evaluate the effect of increasing the number of proline residues on the activity profile. A second pair of molecules (1-Nhis$_6$ and 1-Nhis$_{3,6,9,12}$) was created to explore the effect of modulating the number of Nhis residues within the sequence.

The effects of hydrophobicity on activity and selectivity was further explored with an additional set of molecules described in Table 3. Several sequences were designed with replacement of selected Nspe residues by achiral Npm residues (see FIG. 1). Two sequences contained four Npm residues either aligned on one face (1-Npm$_{2,5,8,11}$) or distributed on two faces (1-Npm$_{2,3,8,9}$) of the peptoid. Additionally, the molecule (1$_{achiral}$-Nspe$_{12}$) with all Nspe replaced with Npm except for the 12$^{th}$ position was designed to be less hydrophobic, yet still somewhat helical; it has been shown that inclusion of a chiral residue at the C-terminus promotes helicity. Lastly, an all achiral version of 1, 1$_{achiral}$, contains all Nspe residues substituted with Npm.

The hydrophobic side chain Nsdp, which is isomerically related to Nsmb (FIG. 1), was incorporated into two additional sequences aimed at further investigating the use of aliphatic side chains. 1-Nsdp$_{all}$ has all Nspe monomers replace with Nsdp, and 1-Nsdp$_{2,5,8,11}$ displays four Nsdp monomers on one face.

A final family of sequences was designed to evaluate the effect of sequence register, charge distribution, and length on activity and selectivity. Compounds 1B and 1C are isomers of 1 in which the sequence register was changed to preclude the presence of terminal charges (Nspe-Nlys-Nspe) or exhibit a C-terminal charge (Nspe-Nspe-Nlys), respectively. Several compounds were also created with increased number of charges (i.e. decreased hydrophobicity) distributed over multiple faces of the molecule. Compound 1-Nlys$_{5,11}$ exhibits the sequence of 1 with the two Nspe monomers at positions 5 and 11 replaced with Nlys resulting in two additional charges. Other variants include a 1B register sequence analogously substituted with Nlys and positions 4 and 10 as both a 12mer (1B$_{12mer}$-Nlys$_{4,10}$) and a 15mer (1B$_{15mer}$-Nlys$_{4,10}$). Similarly, molecules with additional Nlys monomers distributed on three faces (1B$_{12mer}$-Nlys$_{4,6,10}$ and 1B$_{15mer}$-Nlys$_{4,6,10}$) were also created.

X-Ray Reflectivity Studies of Ampetoid Orientation in Lipid Layers

Liquid (aqueous buffer) surface specular X-ray reflectivity (XR) studies were conducted using synchrotron radiation to investigate the membrane orientation and depth of penetration of ampetoid 1 in a model lipid layer which mimics the outer leaflet of the cell membrane (FIG. 6). X-rays reflected off of the monolayer yield an electron density profile perpendicular to the interface, allowing determination of the layer thickness and the presence and orientation of added molecules. The experimental data are represented as a stack of slabs, each with a uniform thickness, electron density, and interface roughness.

XR data for a pure DPPG (anionic) film (FIG. 6—circles) fit well with a two-slab model, yielding a hydrocarbon tail density ($\rho_t/\rho_s$) of 0.99 and a hydrocarbon tail slab thickness (L$_1$) of 17.9 Å, as well as a headgroup electron density ($\rho_h/\rho_s$) of 1.54 and headgroup slab thickness (L$_2$) of 5.7 Å. These data are in good agreement with previous DPPG monolayer X-ray work. The XR profile changed dramatically after peptoid 1 was introduced (FIG. 6—squares), and fit a four-slab model. According to this fit, the first slab ($\rho_t/\rho_s$=0.96, L$_1$=12.1 Å) corresponds to the lipid tails without 1, the second slab ($\rho_{t+p}/\rho_s$=1.05, L$_2$=2.8 Å) to the tails region with partial insertion of 1, the third slab ($\rho_{h+p}/\rho_s$=1.33, L$_2$. 7.0 Å) to the lipid headgroup region with 1 fully inserted, and the fourth slab ($\rho_p/\rho_s$=1.16, L$_2$. 3.6 Å) to 1 alone, protruding beyond the DPPG headgroups. This electron density profile is consistent with insertion of 1 through the lipid headgroups and partially into the lipid tail region. Furthermore, assuming that 1 retains its helical structure in model lipid monolayers, the data suggest that 1 inserts at an angle of approximately 56° between the interface normal and the long helical axis of the peptoid.

TABLE 4

Broad-spectrum antibacterial activity of pexiganan and selected ampetoids against BSL2 and BSL3 pathogenic bacteria.

| | | MICs (μM) | | | | | | | |
|---|---|---|---|---|---|---|---|---|---|
| Strain | Gram | pexiganan | 1 | 1-Pro$_6$ | 1-Pro$_9$ | 1$_{achiral}$ | 1$_{achiral}$-Nspe$_{2,5,8,11}$ | 1-Nsmb$_{2,5,8,11}$ | Ntridec-1$_{4mer}$ |
| *Proteus vulgaris* ATCC 49132 | − | 12.9 | 17.6 | 18.2 | 36.5 | 18.7 | 36.3 | 19.0 | 38.3 |
| *Pseudomonas aeruginosa* ATCC 27853 | − | 1.6 | 4.4 | 18.2 | 18.2 | 9.4 | 36.3 | 9.5 | 9.6 |
| *Proteus mirabilis* ATCC 35659 | − | >51.7 | >70.4 | >72.9 | >72.9 | >75 | >72.6 | >76.0 | 153.3 |
| *Klebsiella pneumoniae* ATCC 33495 | − | 3.2 | 8.8 | 9.1 | 9.1 | 4.7 | 9.1 | 4.8 | 9.6 |
| *Enterobacter aerogenes* ATCC 35029 | − | 12.9 | 8.8 | 72.9 | 36.5 | 75.0 | 36.3 | 19.0 | >153.3 |
| *Escherichia coli* ATCC 25922 | − | 3.2 | 2.2 | 9.1 | 4.6 | 9.4 | 4.5 | 4.8 | 9.6 |
| *Serratia marcescens* ATCC 13880 | − | >51.7 | 70.4 | >72.9 | >72.9 | >75 | >72.6 | >76.0 | 153.3 |
| *Staphylococcus aureus* ATCC 29213 | + | 12.9 | 2.2 | 4.6 | 9.1 | 4.7 | 4.5 | 4.8 | 4.8 |
| *Staphylococcus aureus* VAN1* | + | 6.5 | 2.2 | 4.6 | 4.6 | 4.7 | 4.5 | 4.8 | 4.8 |
| *Staphylococcus aureus* VAN2* | + | 3.2 | 2.2 | 4.6 | 4.6 | 4.7 | 4.5 | 4.8 | 4.8 |
| *Staphylococcus aureus* NRS100 (COL) | + | 6.5 | 2.2 | 4.6 | 4.6 | 4.7 | 4.5 | 4.8 | 4.8 |
| *Staphylococcus aureus* NRS119 | + | 25.8 | 2.2 | 9.1 | 9.1 | 9.4 | 9.1 | 9.5 | 4.8 |
| *Staphylococcus aureus* NRS120 | + | 25.8 | 4.4 | 9.1 | 9.1 | 9.4 | 9.1 | 9.5 | 4.8 |
| *Enterococcus faecalis* ATCC 29212 | + | 12.9 | 2.2 | 4.6 | 4.6 | 9.4 | 4.5 | 4.8 | 9.6 |
| *Enterococcus faecalis* 99* | + | 51.7 | 4.4 | 36.5 | 36.5 | 37.5 | 36.3 | 38.0 | 19.2 |
| *Enterococcus faecium* 106* | + | 1.6 | 2.2 | 2.3 | 2.3 | 2.3 | 2.3 | 2.4 | 4.8 |

*vancomycin resistant

XR data for a pure DPPG (anionic) film (FIG. 6A—circles; cartoon inset, top (B)) fit well with a two-slab model, yielding a hydrocarbon tail density ($\rho_t/\rho_s$) of 0.99 and a hydrocarbon tail slab thickness ($L_1$) of 17.9 Å, as well as a headgroup electron density ($\rho_H/\rho_s$) of 1.54 and headgroup slab thickness ($L_2$) of 5.7 Å. These data are in good agreement with previous DPPG monolayer X-ray work. The XR profile changed dramatically after peptoid 1 was introduced (FIG. 6B—squares; cartoon inset, bottom (C)), and fit a four-slab model. According to this fit, the first slab ($\rho_t/\rho_s$=0.96, $L_1$=12.1 Å) corresponds to the lipid tails without 1, the second slab ($\rho_{t+p}/\rho_s$=1.05, $L_2$=2.8 Å) to the tails region with partial insertion of 1, the third slab ($\rho_{h+p}/\rho_s$=1.33, $L_2$=7.0 Å) to the lipid headgroup region with 1 fully inserted, and the fourth slab ($\rho_p/\rho_s$=1.16, $L_2$=3.6 Å) to 1 alone, protruding beyond the DPPG headgroups. This electron density profile is consistent with insertion of 1 through the lipid headgroups and partially into the lipid tail region. Furthermore, assuming that 1 retains its helical structure in model lipid monolayers, the data suggest that 1 inserts at an angle of approximately 56° between the interface normal and the long helical axis of the peptoid.

Figure 7:
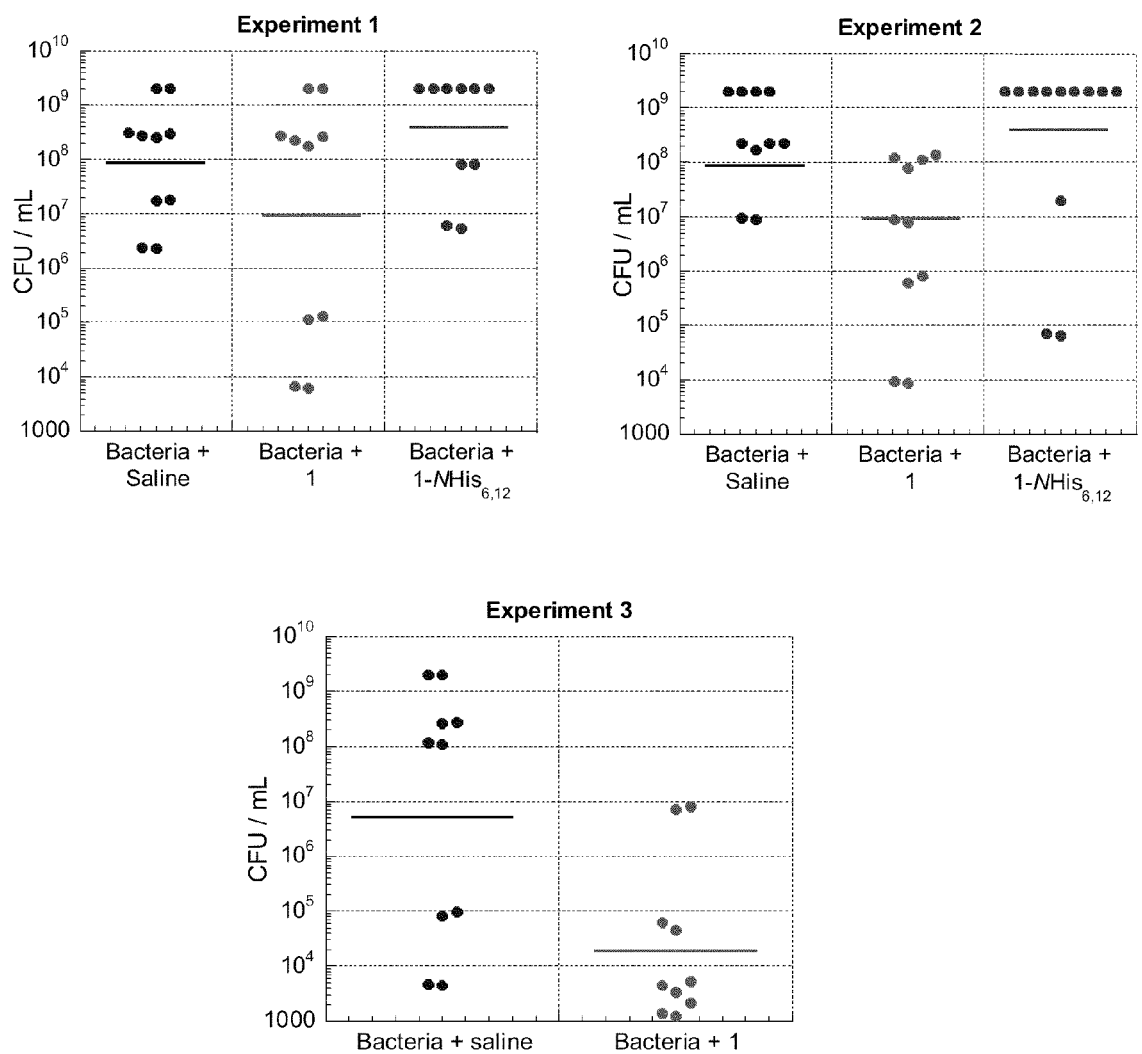
FIG. 7. In vivo efficacy of ampetoids in a mouse peritoneal injection model. Five or six mice were included in each study group for each experiment; the bacterial colony counts from each of two plates per mouse are shown in the dot plot. The horizontal line in each group represents the geometric mean of the population.

Using a murine peritoneal injection mouse model, the ability of peptoids to treat infection was evaluated in vivo. The results from three separate studies of peptoid 1 and two of peptoid 1-Nhis$_{6,12}$ against saline treated controls are shown in FIG. 7. The horizontal line represents the geometric mean of each population.

Previous work has shown that peptoids can be used to create compounds with antimicrobial activities similar to AMPs. In this study, the facile synthesis and high propensity for helix formation of peptoids was exploited to create and study a library of ampetoid variants that suggests functional and mechanistic analogy between ampetoids and AMPs and that demonstrates ampetoids' potential for development into clinically useful antibiotics.

The equivalent activities of 1 and 1$_{enantiomer}$ demonstrate that ampetoid mechanism is not dependent on overall handedness nor on stereospecific interactions with receptors or enzymes, an attribute which has also been observed for many AMPs. Evidence that ampetoids interact with and insert into membranes is provided by X-ray reflectivity studies (FIG. 6). Furthermore, the depth of insertion of peptoid 1—through the headgroups and partially into the lipid tails—demonstrates that 1 interacts simultaneously with hydrophobic and hydrophilic lipid moieties; thus, as with AMPs, the amphipathic structure of 1 is integral to its interactions with membranes. The orientation of 1 at an angle of ~56 to the interface normal suggests that 1 does not operate through a barrel-stave mechanism, since that would require a transmembrane configuration. Although it cannot be concluded that 1 exhibits identical mechanistic behavior to natural, α-helical antimicrobial peptides, these X-ray results demonstrate ampetoid-lipid interactions consistent with those seen for AMPs such as pexiganan and LL-37.

Ultimately, whether ampetoid activity also adheres to trends relating structure and function was determined in a manner analogous to AMPs, and physicochemical properties of selective ampetoids were found consistent with those of selective AMPs and non-selective peptides exhibit close similarities to cytotoxic peptides. Numerous structure-activity studies of a wide variety of AMPs have delineated the physicochemical characteristics that give rise to selective antibacterial activity or non-selective cytotoxicity. Regardless of structural class (i.e. α-helix, β-sheet, loop, or extended), non-selective AMPs typically (1) are very hydrophobic, such that their interactions with membranes are governed primarily by the hydrophobic effect, and (2) have a well-defined amphipathic structure. In contrast, the antibacterial activity of selective AMPs is dependent on (1) high net cationic charge (although excessive cationic charge can also lead to hemolytic activity) and (2) only moderate hydrophobicity. Perhaps counterintuitively, a well-defined amphipathic structure is not necessary for selective antimicrobial activity; destabilization of AMP secondary structure often leads to improvements in selectivity.

The ampetoids 1-Nglu$_{4,10}$, 1$_{15mer}$, 1-Nsna$_{6,12}$, and 1$_{block}$ are all less selective than peptoid 1 (SRs<6.0) (Table 1). Consistent with properties of non-selective AMPs, these compounds are all either more hydrophobic (according to RP-HPLC elution time) and/or less charged (1-Nglu$_{4,10}$) than 1. Furthermore, they are all as (or more) helical than 1 in erythrocyte-mimetic POPC/CH SUVs (FIG. 4), indicative of their well-defined membrane-bound amphipathic structures in that lipid environment.

In contrast, $1_{9mer}$, 1-Nhis$_{6,12}$, and 1-Pro$_6$ all have antibacterial activities comparable to 1, but enhanced selectivities (SRs>6.0). These peptoids are all more hydrophilic than 1, and all have a net charge of at least +3. Thus, ampetoids are selectively active provided they have a net positive charge and are sufficiently but not excessively hydrophobic, a phenomenon that is wholly consistent with observations of selective AMPs. Additionally, retention of antibacterial activity and enhancement of selectivity in the shortened $1_{9mer}$ is analogous to behavior observed in studies of truncated AMPs.

In general, the effect of length on ampetoid potency and selectivity can largely be attributed to differences in hydrophobicity (RP-HPLC retention time, Table 1), which increases proportionally with length. Since the 12mer 1 is more antibacterial than longer and shorter analogs, these results suggest the existence of an optimal hydrophobicity at which antibacterial activity is maximized; added hydrophobicity increases only hemolytic activity. This conclusion is also supported by the hydrophobicity variants, since moderately hydrophobic 2-Nsap$_{2,5,8,11}$ and 2-Nsna$_{6,12}$ are both more antibacterial and more hemolytic than 2, while the strongly hydrophobic 1-Nsna$_{6,12}$ (Table 1) shows enhancement of hemolytic but not antibacterial activity relative to 1. These results are in agreement with observations of AMPs and their variants.

Although they are more hemolytic than 2, peptoids 2-Nsna$_{6,12}$ and 2-Nsap$_{2,5,8,11}$ are still more selective (SRs of 7.6 and 16, respectively) than 1, and their physicochemical properties are consistent with this finding. They are highly charged (+4), moderately hydrophobic, and exhibit CD spectra consistent with low helicity (FIG. 3B, 4B, 5B). The CD spectrum of 2-Nsna$_{6,12}$ exhibits red-shifted extrema, suggesting a destabilized secondary structure. Thus, these variants of 2 all have poorly defined amphipathic structures.

Indeed, results on the whole suggest that, consistent with AMPs, a highly amphipathic structure is required for hemolytic activity, but not for antibacterial activity. CD spectra of ampetoids in POPE/POPG SUVs (FIG. 5) show that the extent of helicity in this bacteria-mimetic system is poorly correlated with antimicrobial activity. 1-Nsna$_{6,12}$, for example, is less helical than 1 (FIG. 5A), but the two compounds have similar antibacterial potencies (Table 1). In contrast, 2-Nsap$_{2,5,8,11}$ is similarly helical to 2 (FIG. 5B), yet 2-Nsmb$_{2,5,8,11}$ is much more antibacterial (Table 1).

Figure 4:
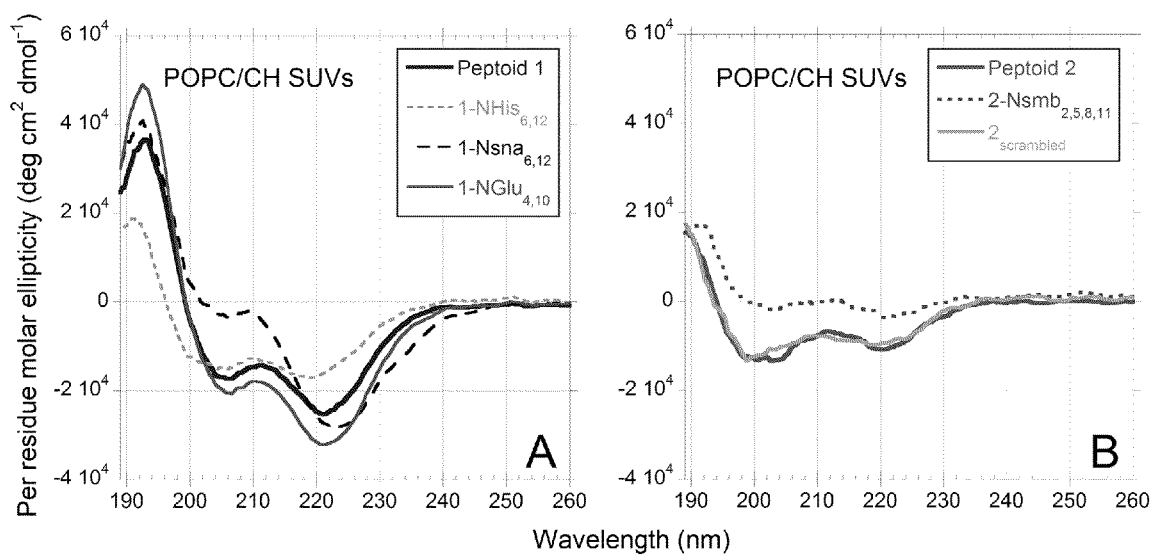
FIGS. 4A-B. CD spectra of (A) variants of 1 and (B) variants of 2 in 5 mM POPC/cholesterol (1:1) SUVs suspended in 10 mM Tris buffer, pH 7.4.
Figure 5:
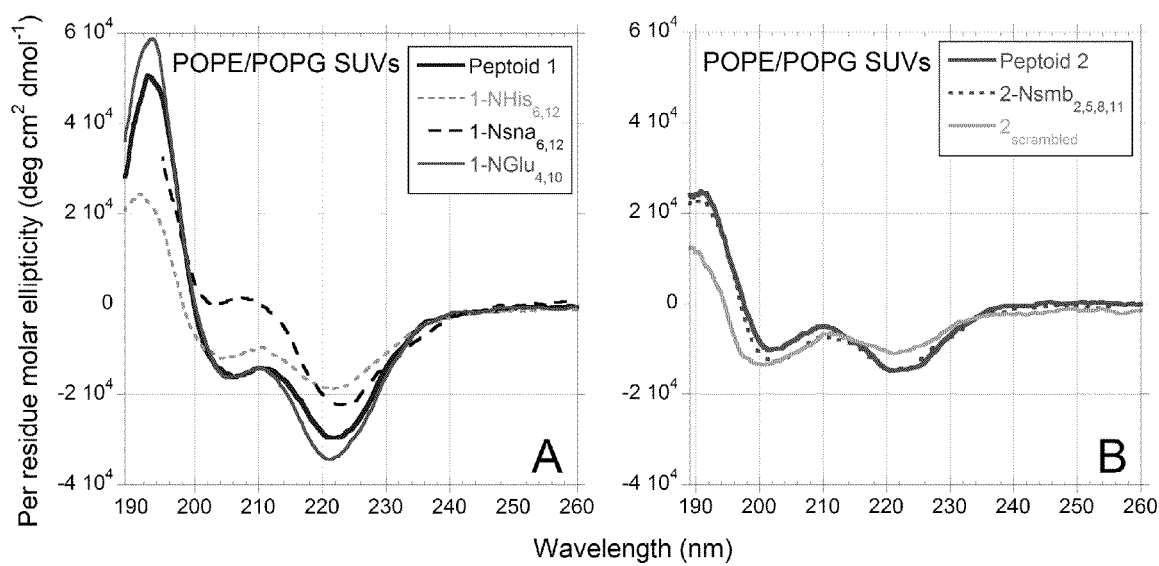
FIGS. 5A-B. CD spectra of (A) variants of 1 and (B) variants of 2 in 5 mM POPE/POPG (7:3) SUVs suspended in 10 mM aqueous Tris buffer, pH 7.4.

CD spectra in erythrocyte-mimetic POPC/CH SUVs (FIG. 4) do, however, reveal a correlation between hemolytic activity and helicity. 1-Nsna$_{6,12}$, and 1-Nglu$_{4,10}$ are the most hemolytic ampetoids (Table 1), and are the most helical in POPC/CH SUVs (FIG. 4A). $1_{15mer}$ is also very hemolytic and as helical as 1 in POPC/CH. Conversely, 1-Nhis$_{6,12}$, 2, 2-Nsmb$_{6,12}$, and $2_{scrambled}$ are less hemolytic (Table 1) and less helical (FIG. 4) than 1. Thus, for these cationic, facially amphipathic compounds, it appears that defined helical structure, which leads to clean segregation between cationic and hydrophobic groups, is important for hemolytic activity. Further insight is provided by $1_{block}$, which has a well-defined terminally amphipathic structure independent of its helicity; $1_{block}$ is hemolytic (SR=2.6). Together, these results suggest that helicity is important only as a means to organize an amphipathic structure, which facilitates oligomerization and a bias toward a non-selective mechanism. Based on this conclusion, a helical but poorly amphipathic compound such as $2_{scrambled}$ should be antimicrobial, but selective; indeed, $2_{scrambled}$ kills bacteria, but exhibits no hemolysis up to 120 μM.

Results also indicate that hydrophobicity is relevant to hemolytic activity, and comparison of 1-Pro$_6$ and 1 establishes this relationship more concretely. These ampetoids have similar sequences with the same net charge and yield nearly congruent CD spectra (FIG. 3A). This suggests that their helical content, and thus their resultant amphipathicity, are similar. However, the Nspe→Pro substitution yields a reduction in hydrophobicity, according to RP-HPLC elution time (Table 1). This single difference is reflected in the lower hemolytic and cytotoxic activities of 1-Pro$_6$ compared to 1, and reveals clearly the dependence of selectivity on hydrophobicity in a case where all other parameters are held constant.

The results in Table 3 provide further insight into how molecular structural features modulate peptoid activity and selectivity. While antimicrobial activity does not change with respect to proline position, cytotoxicity is decreased as the proline is moved closer to the C-terminus. It is possible that proline provides structural stability at the C-terminus that makes it less harmful to mammalian cells while not affecting its ability to kill bacteria. Increasing the number of Nhis residues decreased both the antimicrobial activity as well as the cytotoxicity. Interesting, 1-Nhis$_{6,12}$, the basis sequence for this family, was found to be far less active against *E. coli* ATCC 35218 than the strain originally tested (JM109).

The family of compounds containing varying amounts of achiral residues shows that while the positions of the achiral residues does not significantly affect antimicrobial activity, it may have an impact on selectivity (Table 3, 1-Npm$_{2,5,8,11}$ vs. 1-Npm$_{2,3,8,9}$). Interestingly, both of these compounds exhibit antimicrobial activity equal to that of compound 1, but exhibit superior selectivity. It also appears that antimicrobial activity is decreased with increasing achiral residues, an effect that could be due to the reduced hydrophobicity and decreased organizational structure of the helix. The sequence containing all Nsdp residues is relatively inactive, but that containing 4 Nsdp residues along one face (1-Nsdp$_{2,5,8,11}$) exhibits antimicrobial activity.

Several compounds were made to investigate how increasing the number of charges and distributing them on multiple faces effects activity. Two molecules were increased in length in order to add hydrophobicity to counteract the increased charges. Interestingly, no molecule in this family was shown to be active against *E. coli*, likely due to the decreased hydrophobicity, but all are very active against *B. subtilis*. At the same time, all of them are completely nontoxic to both erythrocytes and mammalian cells. It is possible that this family acts via a different mechanism of action than less highly charged molecules.

The results of the broad spectrum antimicrobial testing and in vivo efficacy study demonstrate the therapeutic potential of antimicrobial peptoids. Nearly all seven peptoids tested were more potent against the nine Gram positive strains (including four vancomycin-resistant) than pexiganan. Against Gram negative strains, compounds 1 and 1-Nsdp$_{2,5,8,11}$ showed activity comparable to that of pexiganan.

The in vivo results shown in FIG. 2 demonstrate that the bacterial counts from the peritoneal lavage were significantly reduced upon treatment with peptoid 1 (p<0.05). Additionally, no mice treated with peptoid 1 died prematurely.

Of the eleven mice treated with peptoid 1-Nhis$_{6,12}$ on the other hand, eight died prematurely during the exposure period. Of the 15 saline treated controls across all three experiments, only 4 died prematurely. Also, the average bacterial count was not reduced in comparison to saline treated controls.

In summary, the results suggest that antibacterial activity among AMPs and ampetoids alike is dependent on moderate hydrophobicity and net cationic charge, while hemolytic activity is associated primarily with high hydrophobicity and a strongly amphipathic structure, regardless of helical content. MTS assays demonstrate a similar trend between hemolytic activity and cytotoxicity against A549 eukaryotic mammalian cells. The relationships between structure and function in ampetoids are empirically analogous to those in AMPs. X-ray reflectivity studies, which show that ampetoid 1 is membrane-active and adopts a stable membrane-bound orientation, demonstrate molecular-level analogy between AMPs and ampetoids.

Results with alkylated variants demonstrate that alkyl chain attachment may be used to create very short peptoids that are as antimicrobially active and non-toxic as longer unalkylated helices. In particular, both Ndec-1$_{6mer}$ and Ntridec-1$_{4mer}$ were found to be comparable in activity and selectivity to 1. Given that the lengths of most AMPs range from ~12-100 amino acids, it is notable that such low molecular weight (<1 kDa) peptoids exhibit such potency and selectivity against both bacteria and fungi. N-terminal attachment of alkyl tails can be a useful motif for improving the potency and decreasing the molecular weight of ampetoids. Moreover, alkylation is an effective and tunable modification that exhibits a clear effect on peptoid function.

Peptoids have greater potential than peptides to be used as pharmaceuticals and in biomaterials due to their improved stability, bioavailability, and highly tunable side chain chemistry. Since peptides' potential for toxicity is a major obstacle limiting their clinical use, ampetoids' low cytotoxicity observed here relative to the AMP pexiganan further emphasizes their therapeutic potential. The results reported herein will aid in the rational design and optimization of ampetoids and other non-natural oligomers as antimicrobials in the future.

Figure 9:
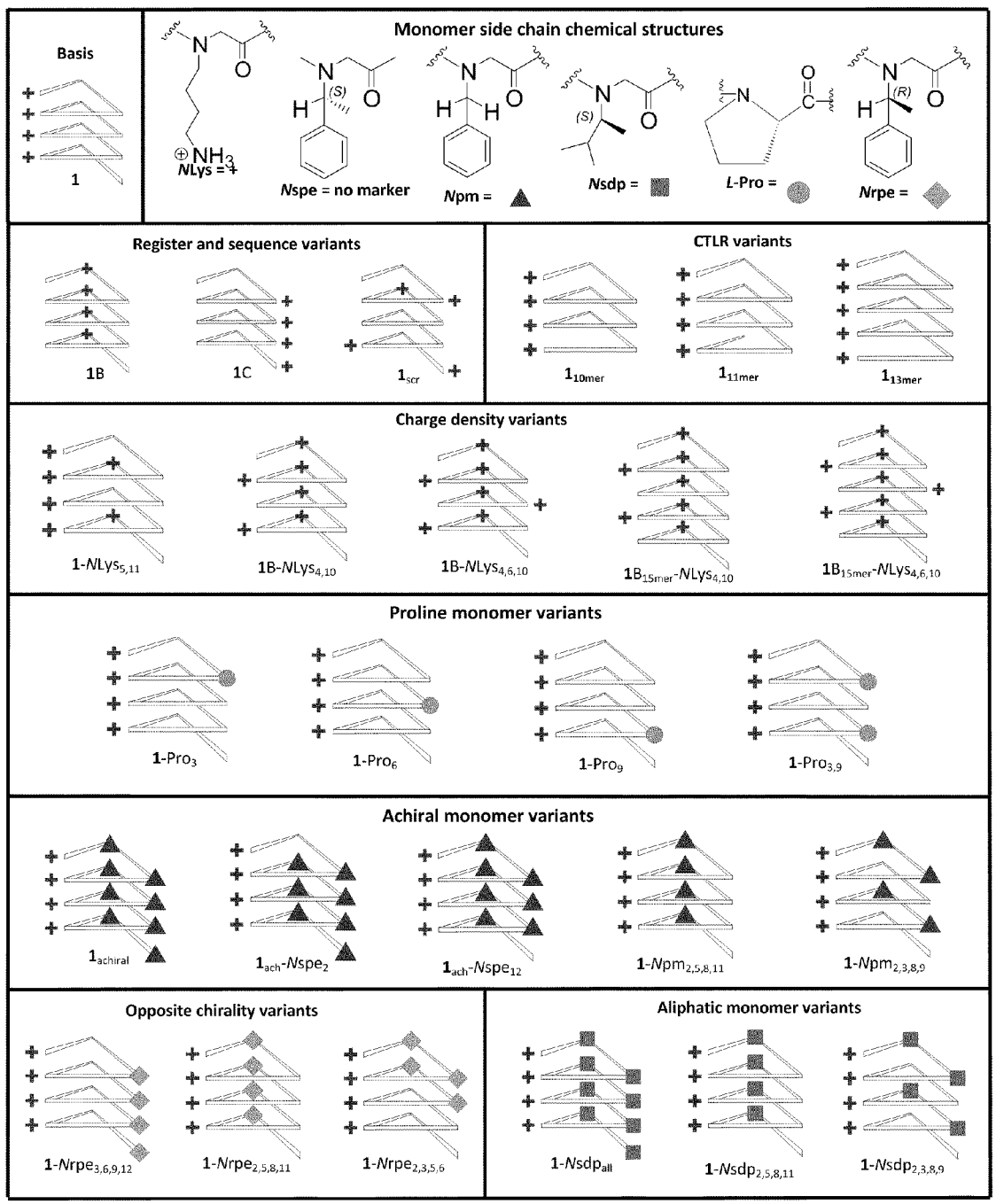
FIG. 9: Schematics of ameptoid variants and side chain structures. By convention, the N-terminus is on the left and the C-terminus is on the right. Note that the schematics shown here are for visualization purposes only and not intended to imply the actual folding behavior of each molecule. Points on the triangular helicies that have no marker are Nspe monomers.
Figure 17A:
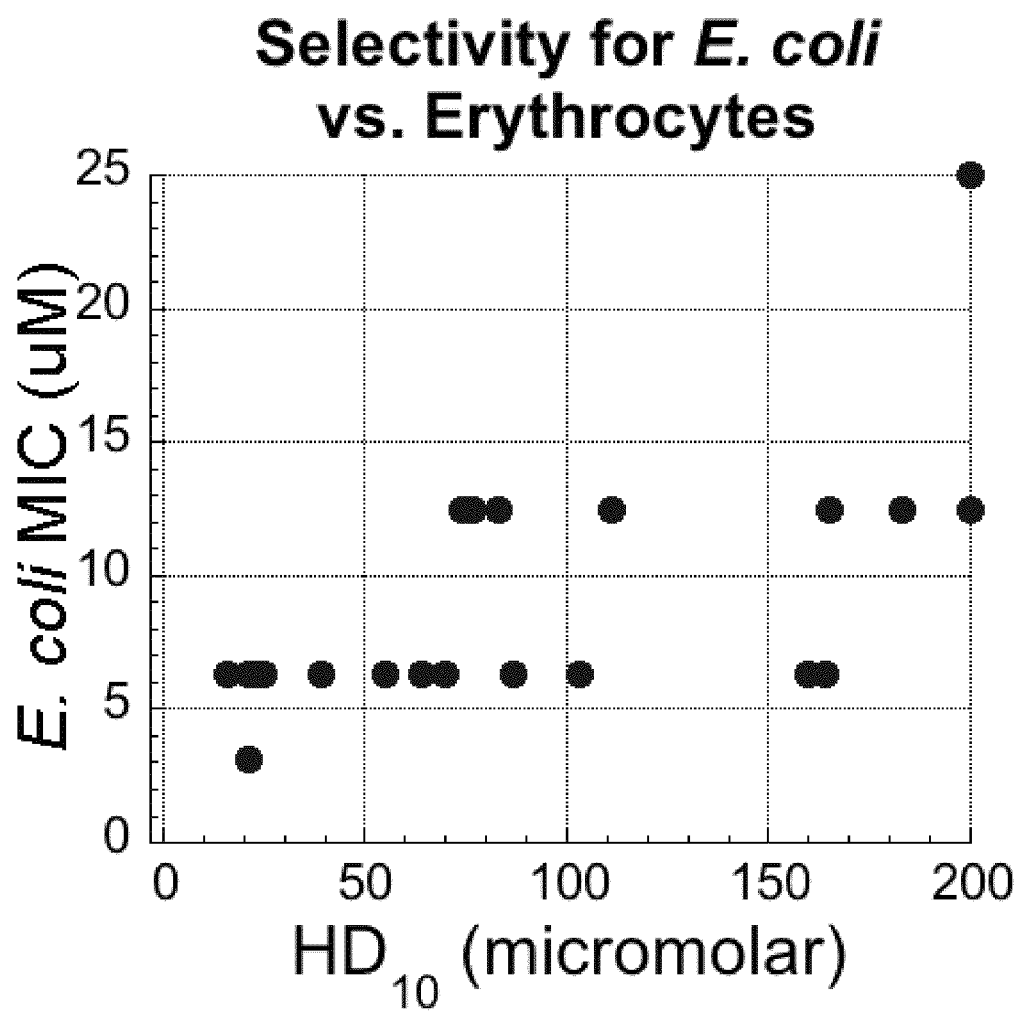
FIGS. 17A-B: Comparison of antimicrobial/hemolytic activity profiles for selected ampetoids. Those with the most favorable profiles appear at the lower right portion of each plot.
Figure 17B:
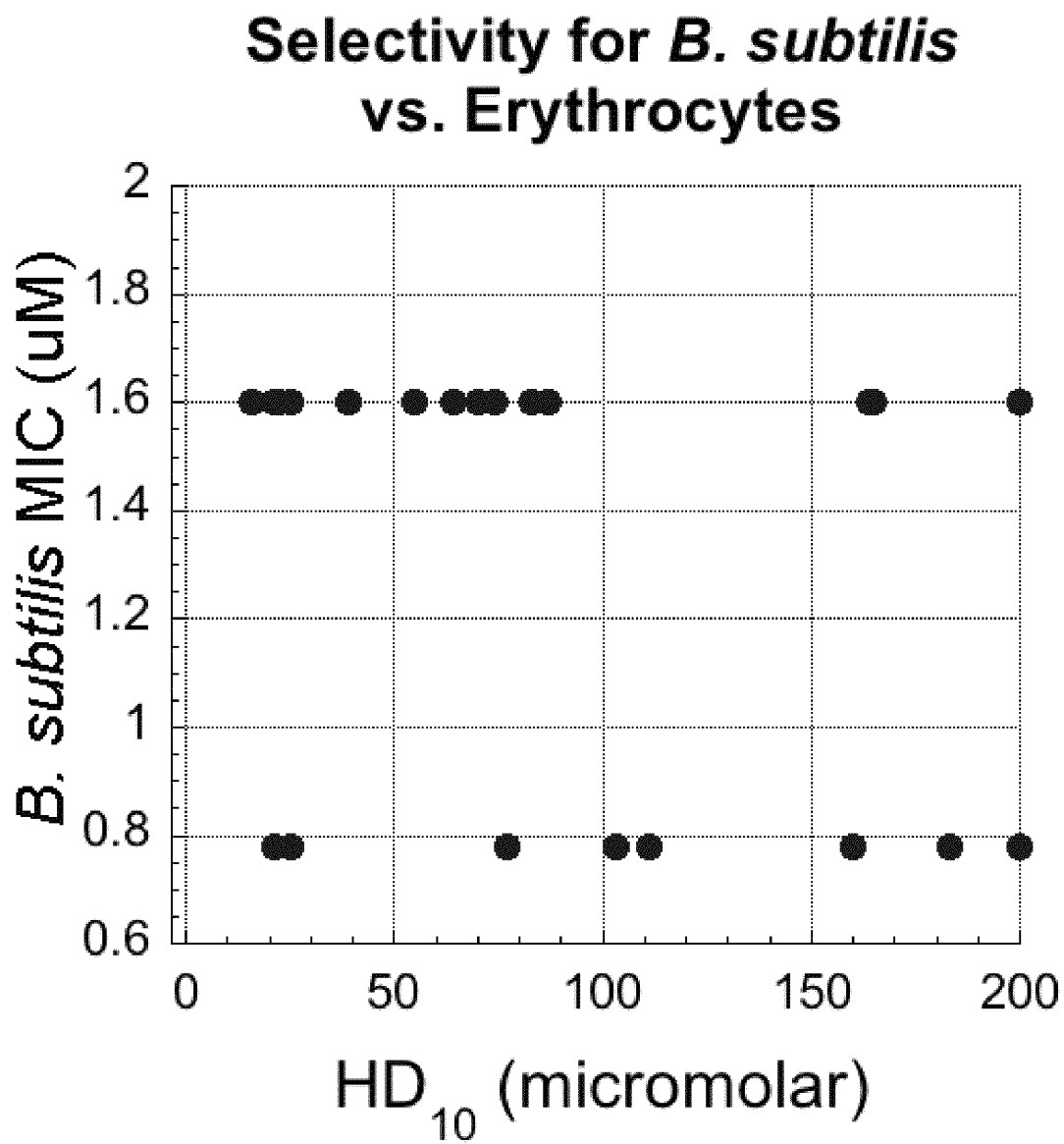

As a continuation of the study described above, various other ampetoids were created with the goal of more fully exploring how and to what extent specific structural characteristics influence selectivity. (See Tables 5-7, FIGS. 9-17 and Examples 10-15.) Additional ampetoids were derived from the previously reported dodecamer, peptoid 1, which is composed of ⅓ lysine-like charged monomers (Nlys) and ⅔ phenylalanine-like hydrophobic monomers (Nspe) arranged in a repeating sequence H-(Nlys-Nspe-Nspe)$_4$-NH (FIG. 9, Table 5). With reference to certain compounds previously discussed, additional molecules were designed to explore the importance of (1) primary sequence, (2) sequence register, (3) net charge, and (4) charge-to-length ratio (CTLR) on antimicrobial activities and cell selectivities. The effects of different hydrophobic moieties were evaluated by systematically replacing one or more Nspe monomers with other hydrophobic moieties: (1) L-proline monomers (2) achiral hydrophobic monomers, (3) opposite chirality hydrophobic monomers (Nrpe), and (4) aliphatic hydrophobic monomers. Again, as above, Pexiganan, a widely studied and clinically-relevant AMP analog of magainin-2, was included in this study as a basis of comparison to AMPs.

Schematic structures showing the three-fold periodic architecture of peptoid 1 (the basis sequence) and ampetoid variants, including those discussed above, are shown in FIG. 9, to clarify the design strategy and relationships among ampetoid variants discussed herein. The three molecular ampetoid faces discussed throughout this work are depicted as aligned monomers on the left, back, and right sides, as shown. The full sequence of each molecule is displayed in Table 5, along with other molecular properties including molecular weight, net charge, CTLR, and reversed-phase HPLC (RP-HPLC) solvent composition upon elution, as a measure of molecular hydrophobicity. In general, as shown above, the naming convention for ampetoids includes the basis compound (1, in most cases) followed by a description of how the sequence was modified compared to the basis compound. For example, compound 1B-Nlys$_{4,10}$ describes a variant based on the sequence of 1B in which Nlys monomers were substituted at positions 4 and 10.

The activities of all compounds against bacterial strains and mammalian cells are summarized in Table 6. The potencies of all compounds were determined against representative Gram-negative (*E. coli* ATCC 35218) and Gram-positive (*B. subtilis* ATCC 6633) biosafety level 1 (BSL1) organisms. In addition to hemolytic activity, the conventional measure of toxicity to mammalian cells, the effect of each ampetoid on NIH 3T3 mouse fibroblast cells was determined using the MTS tetrazolium salt-based colorimetric assay. While hemolysis measures the degree to which erythrocytes are lysed, the MTS assay indirectly quantifies the extent to which cellular metabolic activity is inhibited.

Because the range of hemolytic activities displayed by these molecules is significantly greater than that of inhibitory activities, hemolysis assays provide a more sensitive gauge of activity against mammalian cells. Therefore, the selectivity of each ampetoid for various bacterial strains compared to erythrocytes is reported as the selectivity ratio (SR), which is defined as the quotient of the 10% hemolytic dose and the minimum inhibitory concentration (MIC) for each bacterial strain.

The ampetoids in this library exhibited antibacterial potencies against Gram-negative *E. coli* that ranged from 3.1 µM to >100 µM. Likewise, hemolytic activity ranged from HD$_{10}$=16 µM to HD$_{10}$>200 µM and metabolic inhibitory activity from ID$_{50}$=4.9 µM to ID$_{50}$>100 µM. The breadth of activities and selectivities evidenced by these compounds suggests that this library was well designed to effect a range of responses for elucidating structure-activity relationships. Compared to 1 (SR$_{E.\ coli}$=3.3), 17 of the 26 ampetoid variants demonstrate improved selectivity for *E. coli* (SR$_{E.\ coli}$=6.8-26). Four ampetoids (1-Npm$_{2,5,8,11}$, 1$_{11mer}$, 1$_{ach}$-Nspe$_2$, 1$_{ach}$-Nspe$_{12}$) exhibited equivalent activity (6.3 µM) and superior selectivity (SR$_{E.\ coli}$=14-26) compared to pexiganan (SR$_{E.\ coli}$=11). In comparison to their activities against *E. coli*, all oligomers were more potent against *B. subtilis*, with MICs ranging from 0.78 to 1.6 µM. Corresponding selectivity ratios were as high as >256.

TABLE 5

Sequence and molecular properties of ampetoids and comparator peptide pexiganan. See FIG. 2.1 for the structures of the peptoid monomers indicated in each sequence. HPLC elution is reported as the average percentage of acetonitrile in the solvent mixture upon compound elution for three compound elution for three injections. A linear acetonitrile/water (0.1% trifluoroacetic acid) gradient of 5%-95% acetonitrile over 45 minutes was run on a C18 column. § CTLR strands of stands for charge-to-length ratio, which is defined as the ratio of the total number monomers to the total number of monomers in each sequence.

| | Compound | MW | Sequence | HPLC elution (% ACN)* | Net Charge | CTLR§ |
|---|---|---|---|---|---|---|
| Comparators | 1 | 1819 | H-(Nlys-Nspe-Nspe)$_4$-NH$_2$ | 65.1 | +4 | 0.33 |
| | Pexiganan | 2477 | GIGKFLKKAKKFGKAFVKILKK (SEQ ID NO: 1)-NH$_2$ | 50.2 | +9 | 0.41 |
| Register & | 1B | 1819 | H-(Nspe-Nlys-Nspe)$_4$-NH$_2$ | 63.4 | +4 | 0.33 |
| sequence | 1C | 1819 | H-(Nspe-Nspe-Nlys)$_4$-NH$_2$ | 64.8 | +4 | 0.33 |
| variants | 1scr | 1819 | H-(Nspe)$_2$-(Nlys-Nspe)$_3$-(Nspe)$_3$-Nlys-NH$_2$ | 61.1 | +4 | 0.33 |

TABLE 5-continued

Sequence and molecular properties of ampetoids and comparator peptide pexiganan. See FIG. 2.1 for the structures of the peptoid monomers indicated in each sequence. HPLC elution is reported as the average percentage of acetonitrile in the solvent mixture upon compound elution for three compound elution for three injections. A linear acetonitrile/water (0.1% trifluoroacetic acid) gradient of 5%-95% acetonitrile over 45 minutes was run on a C18 column. § CTLR strands of stands for charge-to-length ratio, which is defined as the ratio of the total number monomers to the total number of monomers in each sequence.

|  | Compound | MW | Sequence | HPLC elution (% ACN)* | Net Charge | CTLR§ |
|---|---|---|---|---|---|---|
| Increased charge variants | 1-$N$lys$_{5,11}$ | 1753 | H-($N$lys-$N$spe-$N$spe-$N$lys-$N$lys-$N$spe)$_2$-NH$_2$ | 51.2 | +6 | 0.50 |
|  | 1B-$N$lys$_{4,10}$ | 1753 | H-($N$spe-$N$lys-$N$spe-$N$lys-$N$lys-$N$spe)$_2$-NH$_2$ | 52.7 | +6 | 0.50 |
|  | 1B-$N$lys$_{4,6,10}$ | 1720 | H-($N$spe-$N$lys)$_2$-$N$lys$_2$-($N$spe-$N$lys)$_2$-$N$lys-$N$spe-NH$_2$ | 45.4 | +7 | 0.58 |
|  | 1B$_{15mer}$-$N$lys$_{4,10}$ | 2204 | H-($N$spe-$N$lys-$N$spe-$N$lys-$N$lys-$N$spe)$_2$-$N$spe-$N$lys-$N$spe-NH$_2$ | 55.5 | +7 | 0.47 |
|  | 1B$_{15mer}$-$N$lys$_{4,6,10}$ | 2171 | H-($N$spe-$N$lys)$_2$-$N$lys$_2$-($N$spe-$N$lys)$_2$-$N$lys-$N$spe$_2$-$N$lys-$N$spe-NH$_2$ | 50.8 | +8 | 0.53 |
| Length variants | 1$_{10mer}$ | 1497 | H-($N$lys-$N$spe-$N$spe)$_3$-$N$lys-NH$_2$ | 60.9 | +4 | 0.40 |
|  | 1$_{11mer}$ | 1658 | H-($N$lys-$N$spe-$N$spe)$_3$-$N$lys-$N$spe-NH$_2$ | 63.5 | +4 | 0.36 |
|  | 1$_{13mer}$ | 1948 | H-($N$lys-$N$spe-$N$spe)$_4$-$N$lys-NH$_2$ | 62.8 | +5 | 0.38 |
| Proline containing variants | 1-Pro$_3$ | 1755 | H-$N$lys-$N$spe-L-Pro-($N$lys-$N$spe-$N$spe)$_3$-NH$_2$ | 63.0 | +4 | 0.33 |
|  | 1-Pro$_6$ | 1755 | H-$N$lys-$N$spe$_2$-$N$lys-$N$spe-L-Pro-($N$lys-$N$spe$_2$)$_2$-NH$_2$ | 62.4 | +4 | 0.33 |
|  | 1-Pro$_9$ | 1755 | H-($N$lys-$N$spe$_2$)$_2$-$N$lys-$N$spe-L-Pro-($N$lys-$N$spe$_2$)-NH$_2$ | 62.6 | +4 | 0.33 |
|  | 1-Pro$_{3,9}$ | 1691 | H-($N$lys-$N$spe-L-Pro-$N$lys-$N$spe-$N$spe)$_2$-NH$_2$ | 58.1 | +4 | 0.33 |
| Chirality variants | 1-$N$rpe$_{3,6,9,12}$ | 1819 | H-($N$lys-$N$spe-$N$rpe)$_4$-NH$_2$ | 63.5 | +4 | 0.33 |
|  | 1-$N$rpe$_{2,5,8,11}$ | 1819 | H-($N$lys-$N$rpe-$N$spe)$_4$-NH$_2$ | 66.4 | +4 | 0.33 |
|  | 1-$N$rpe$_{2,3,5,6}$ | 1819 | H-($N$lys-$N$rpe-$N$rpe)$_2$-($N$lys-$N$spe-$N$spe)$_2$-NH$_2$ | 65.0 | +4 | 0.33 |
| Achiral variants | 1$_{ach}$ | 1701 | H-($N$lys-$N$pm-$N$pm)$_4$-NH$_2$ | 59.8 | +4 | 0.33 |
|  | 1$_{ach}$-$N$spe$_2$ | 1721 | H-($N$lys-$N$spe-$N$pm)-($N$lys-$N$pm-$N$pm)$_3$-NH$_2$ | 60.8 | +4 | 0.33 |
|  | 1$_{ach}$-$N$spe$_{12}$ | 1721 | H-($N$lys-$N$pm-$N$pm)$_3$-($N$lys-$N$pm-$N$spe)-NH$_2$ | 62.0 | +4 | 0.33 |
|  | 1-$N$pm$_{2,3,8,9}$ | 1763 | H-($N$lys-$N$pm-$N$pm-$N$lys-$N$spe-$N$spe)$_2$-NH$_2$ | 63.3 | +4 | 0.33 |
|  | 1-$N$pm$_{2,5,8,11}$ | 1763 | H-($N$lys-$N$pm-$N$spe)$_4$-NH$_2$ | 63.6 | +4 | 0.33 |
| Aliphatic variants | 1-$N$sdp$_{all}$ | 1547 | H-($N$lys-$N$sdp-$N$sdp)$_4$-NH$_2$ | 63.2 | +4 | 0.33 |
|  | 1-$N$sdp$_{2,3,8,9}$ | 1683 | H-($N$lys-$N$sdp-$N$sdp-$N$lys-$N$spe-$N$spe)$_2$-NH$_2$ | 64.7 | +4 | 0.33 |
|  | 1-$N$sdp$_{2,5,8,11}$ | 1683 | H-($N$lys-$N$sdp-$N$spe)$_4$-NH$_2$ | 63.8 | +4 | 0.33 |

TABLE 6

Activity of ampetoids and pexiganan against bacteria and mammalian cells. Presented are the minimum inhibitory concentrations (MICs) against *E. coli* (ATCC 35218) and *B. subtilis* (ATCC 6633), 10% and 50% hemolytic doses (HD), and 50% inhibitory doses (ID) against NIH 3T3 mouse fibroblast cells.

|  |  | Antimicrobial Activity | | Mammalian Cell Activity | | | |
|---|---|---|---|---|---|---|---|
|  |  | *E. coli* MIC | *B. subtilis* MIC | HD$_{10}$/ HD$_{50}$ | ID$_{50}$ | Selectivity Ratios* | |
|  | Compound | (μM) | (μM) | (μM) | (μM) | SR*E. coli* | SR*B. subtilis* |
| Comparative Molecules | 1 | 6.3 | 1.6 | 21/100 | 5.1 | 3.3 | 13 |
|  | Pexiganan | 6.3 | 1.6 | 70/>200 | 9 | 11 | 44 |
| Register & sequence variants | 1B | 6.3 | 1.6 | 55/>100 | 4.9 | 8.7 | 34 |
|  | 1C | 6.3 | 1.6 | 25/>100 | 5.6 | 4.0 | 16 |
|  | 1scr | 6.3 | 1.6 | 64/>200 | 8.5 | 10 | 40 |
| Increased net charge variants | 1-$N$lys$_{5,11}$ | 50 | 1.6 | >100/>100 | 85 | >2 | >63 |
|  | 1B-$N$lys$_{4,10}$ | 50 | 0.78 | >200/>200 | 83 | >4 | >256 |
|  | 1B-$N$lys$_{4,6,10}$ | >100 | 1.6 | >200/>200 | >100 | Inactive | >125 |
|  | 1B$_{15mer}$-$N$lys$_{4,10}$ | 50 | 0.78 | >200/>200 | 16 | >4 | >256 |
|  | 1B$_{15mer}$-$N$lys$_{4,6,10}$ | >100 | 0.78 | >200/>200 | 40 | Inactive | 256 |
| Length variants | 1$_{10mer}$ | 12.5 | 0.78 | >200/>200 | 54 | >16 | >256 |
|  | 1$_{11mer}$ | 6.3 | 0.78 | 103/>200 | 11 | 16 | 132 |
|  | 1$_{13mer}$ | 3.1 | 0.78 | 21/>100 | 5.6 | 6.8 | 27 |

TABLE 6-continued

Activity of ampetoids and pexiganan against bacteria and mammalian cells.
Presented are the minimum inhibitory concentrations (MICs) against *E. coli*
(ATCC 35218) and *B. subtilis* (ATCC 6633), 10% and 50% hemolytic doses
(HD), and 50% inhibitory doses (ID) against NIH 3T3 mouse fibroblast cells.

| | | Antimicrobial Activity | | Mammalian Cell Activity | | Selectivity Ratios* | |
|---|---|---|---|---|---|---|---|
| | | *E. coli* MIC | *B. subtilis* MIC | $HD_{10}/HD_{50}$ | $ID_{50}$ | | |
| | Compound | (µM) | (µM) | (µM) | (µM) | $SR_{E.\,coli}$ | $SR_{B.\,subtilis}$ |
| Proline containing variants | $1\text{-Pro}_3$ | 12.5 | 1.6 | 74/>200 | 12 | 5.9 | 46 |
| | $1\text{-Pro}_6$ | 12.5 | 1.6 | 83/>200 | 18 | 6.6 | 52 |
| | $1\text{-Pro}_9$ | 12.5 | 1.6 | 165/>200 | 24 | 13 | 103 |
| | $1\text{-Pro}_{3,9}$ | 50 | 1.6 | >200/>200 | 71 | 4.0 | 125 |
| Chirality variants | $1\text{-}N\text{rpe}_{3,6,9,12}$ | 6.3 | 1.6 | 16/67 | 3.8 | 2.5 | 10 |
| | $1\text{-}N\text{rpe}_{2,5,8,11}$ | 6.3 | 1.6 | 22/95 | 5.2 | 3.5 | 14 |
| | $1\text{-}N\text{rpe}_{2,3,5,6}$ | 6.3 | 0.78 | 25/96 | 4.8 | 4.0 | 32 |
| Achiral variants | $1_{ach}$ | 12.5 | 0.78 | 183/>200 | 16 | 15 | 235 |
| | $1_{ach}\text{-}N\text{Spe}_2$ | 6.3 | 0.78 | 160/>200 | 11 | 25 | 205 |
| | $1_{ach}\text{-}N\text{spe}_{12}$ | 6.3 | 1.6 | 164/>200 | 15 | 26 | 103 |
| | $1\text{-}N\text{pm}_{2,3,8,9}$ | 6.3 | 1.6 | 39/>200 | 15 | 6.2 | 24 |
| | $1\text{-}N\text{pm}_{2,5,8,11}$ | 6.3 | 1.6 | 87/>200 | 6.8 | 14 | 54 |
| Aliphatic variants | $1\text{-}N\text{sdp}_{all}$ | 25 | 0.78 | >200/>200 | 64 | >8 | 256 |
| | $1\text{-}N\text{sdp}_{2,3,8,9}$ | 12.5 | 0.78 | 77/>200 | 19 | 6.2 | 99 |
| | $1\text{-}N\text{sdp}_{2,5,8,11}$ | 12.5 | 0.78 | 111/>200 | 20 | 9.7 | 142 |

*Selectivity ratio (SR) is defined as the ratio of the 10% hemolytic dose to the MIC for the bacterial strain of interest.

The secondary structure of ampetoids was evaluated using circular dichroism (CD) spectroscopy in 10 mM Tris buffer (pH 7.4) and the same buffer containing small unilamellar vesicles (SUVs) comprised of either POPC/cholesterol (2:1 mole ratio) or POPE/POPG (7:3 mole ratio). Whereas the POPC/cholesterol mixture is a zwitterionic binary model lipid preparation that mimics the membrane of erythrocytes, the negatively charged POPE/POPG mixture mimics the composition of the *E. coli* outer membrane. A peptoid composed of aromatic right handed poly-proline-type-I-like helix exhibits spectral features including a maximum at 192 nm and two local minima at ~202 nm and ~220 nm, respectively.

Peptoid 1, with a periodic trimer repeat sequence of Nlys-Nspe-Nspe, is composed of four facially-aligned Nlys monomers (positions 1, 4, 7, and 10) along the left molecular face and has a charged N-terminal monomer, as shown in FIG. 9. Two isomeric variants were made in which the sequence register was modified, a change that most overtly affects the relative position of monomers with respect to the terminal positions. Peptoid 1B has a trimer repeat of Nspe-Nlys-Nspe, exhibits charged monomers along the back face (positions 2, 5, 8, and 11) and has hydrophobic moieties at both termini. Ampetoid 1C exhibits a sequence register of Nspe-Nspe-Nlys, has charged monomers along the right face (positions 3, 6, 9, and 12), and has a charged monomer at the C-terminal position (see FIG. 9). The last variant in this family is a "scrambled" isomer, $1_{scr}$, which was made with a non-periodic sequence in which the four charged monomers are distributed across all three molecular faces (FIG. 9).

The antimicrobial potencies against *E. coli* (MIC=6.3 µM) and *B. subtilis* (MIC=1.6 µM) of all three variants were the same as for 1, and their toxicities to NIH 3T3 cells were also similar, with $ID_{50}$ values ranging from 4.9-5.6 µM. The hemolytic activity, however, was reduced for $1_{scr}$ ($HD_{10}$=64 µM) and 1B ($HD_{10}$=55 µM) compared to 1 ($HD_{10}$=21 µM) and 1C ($HD_{10}$=25 µM). As a result, the selectivities for $1_{scr}$ ($SR_{E.\,coli}$=10) and 1B ($SR_{E.\,coli}$=8.7) were more favorable in comparison to 1 ($SR_{E.\,coli}$=3.3) and 1C ($SR_{E.\,coli}$=4.0).

CD spectroscopy showed that all these variants exhibited helicity in 10 mM Tris buffer similar to that of 1, with $1_{scr}$ being slightly more helical and 1C, slightly less (FIG. 10A). In both POPC/cholesterol and POPE/POPG lipids, however, 1B exhibited significantly increased helical intensity at 220 nm compared to the other variants (FIGS. 10B, C). By nature of its scrambled sequence design, the extent of helicity for $1_{scr}$ is decoupled from its degree of amphipathicity; the distribution of charges on all three molecular faces reduces its amphipathicity regardless of a three-fold periodic helical architecture. It is possible that the reduced intramolecular electrostatic repulsion of side chain moieties along a given molecular face in $1_{scr}$ readily accommodates a more helical secondary structure, despite its overall reduced amphipathicity. Based on previous studies, reduction in amphipathicity can improve selectivity without compromising antimicrobial activity. Indeed, $1_{scr}$ exhibits improved selectivity ($SR_{E.\,coli}$=10) compared to 1 ($SR_{E.\,coli}$=3.3) with no reduction in antimicrobial activity ($MIC_{E.\,coli}$=6.3 µM for both molecules).

A second family of ampetoids was designed to evaluate the effect of increased charge density on potency and selectivity (FIG. 9). Structure-activity relationships derived from ampetoid variants with decreased net charge were found to significantly reduce their selectivity for bacteria, likely due to the less favorable electrostatic interaction with negatively charged bacterial membranes. The variants in this family of ampetoids were designed to explore the effect of increasing net charge and charge-to-length-ratio (CTLR) on cell selectivity. Ampetoid 1, and most other variants in this library, have a net charge of +4 and CTLR of 0.33. These compounds exhibit net charges ranging from +6 to +8, and CTLRs ranging from 0.47-0.58. Additionally, the hydrophobicities of these compounds (ranging from 45.4% to 55.5% acetonitrile upon HPLC elution) were all significantly reduced compared to 1 (65.1%) (Table 9). 1-Nlys$_{5,11}$ has a total of six positive charges with two additional Nlys monomers (compared to 1) substituted at positions 5 and 11, which are aligned along a back face of the helix (FIG. 9). 1B-Nlys$_{4,10}$ is an isomeric variant of 1-Nlys$_{5,11}$ with the sequence register of 1B, and 1B-Nlys$_{4,6,10}$ similarly has a net charge of +7 with cationic charge on all three molecular faces. Longer 15mer variants, 1B$_{15mer}$-Nlys$_{4,10}$ and 1B$_{15mer}$-Nlys$_{4,6,10}$, were also made with an additional (Nspe-Nlys-Nspe) turn on the C-terminus, giving them net charges of +7 and +8, respectively (FIG. 9).

All variants in this family were significantly less active against *E. coli* (MIC=50->100 µM) and were non-hemolytic (HD$_{10}$>100 µM), a result largely effected by the reduced hydrophobicity of these variants compared to 1. Because this family of variants does not exhibit a broad range of selectivities (SR$_{E.\ coli}$>2 to >4), elucidating a meaningful relationship between physicochemical properties and selectivity is difficult. A general trend observed, however, is that variants with a CTLR of less than ~0.50, hydrophobicity greater than ~50% acetonitrile, and one completely hydrophobic face (1-Nlys$_{5,11}$, 1B-Nlys$_{4,10}$, and 1B$_{15mer}$-Nlys$_{4,10}$) exhibited weak activity (MIC$_{E.\ coli}$=50 µM). Variants with CTLRs greater than ~0.50, hydrophobicity less than ~50% acetonitrile, and had charges distributed on all three molecular faces (1B-Nlys$_{4,6,10}$ and 1B$_{15mer}$-Nlys$_{4,6,10}$) were completely inactive (MIC$_{E.\ coli}$>100 µM). These results are commensurate with structure activity relationships previously established for both AMPs, and ampetoids: (1) antimicrobial oligomers must be sufficiently hydrophobic to be potent against Gram-negative bacteria, and (2) highly charged and poorly amphipathic structures are generally selective.

It is most notable that the reduction in activity against *E. coli* exhibited by this family of molecules did not carry over to their activities against *B. subtilis*. Despite the marked change in physicochemical properties (NC as high as +8, hydrophobicity as low as 45.4% acetonitrile, and CTLR as high as 0.58) exhibited by this family of molecules compared to 1 (NC=+4, hydrophobicity=65.1%, and CTLR=0.33), the MICs of these variants against *B. subtilis* were very similar to that of 1, ranging from 0.78-1.6 µM. The resultant selectivity ratios of molecules in this library for *B. subtilis* were among the highest of all compounds tested (SR$_{B.\ subtilis}$>256).

The CD spectra in FIG. 11 show that, with the exception of 1B-Nlys$_{4,6,10}$, all compounds exhibited helicity similar to that of 1 in 10 mM Tris buffer. In POPC/cholesterol lipids, however, helicity was inversely related to CTLR, and concomitantly, achiral monomer content. The effect of increased achiral monomer content on peptoid CD spectra is demonstrated plainly in the hydrophobic environment of lipid vesicles; as shown in FIG. 11B, increased achiral monomer content reduced overall CD signal intensity, particularly at 220 nm.

Variants of the dodecameric peptoid 1 that ranged in length from 10-13 monomers were explored as shown in FIG. 9 and Table 5. Previous studies that explored ampetoid length variants with a constant CTLR (1$_{6mer}$, 1$_{9mer}$, and 1$_{15mer}$) showed that increased length beyond 12 monomers (ampetoid 1) only increased hemolytic activity without improving antimicrobial potency. The variants in this study, 1$_{10mer}$, 1$_{11mer}$, 1, and 1$_{13mer}$ exhibit small differences in sequence length, but most notably effect a range of CTLRs (0.33-0.40). This range of CTLR is significantly lower compared to the range exhibited by charge density variants (0.47-0.58). The CD spectra shown in FIG. 12 suggest that in both aqueous buffer and lipid environments, all variants are similarly helical, and therefore exhibit similar amphipathicities.

Considering first only those variants with a net charge of +4 (1$_{10mer}$, 1$_{11mer}$, 1), both hydrophobicity, and CTLR scale monotonically with length. Ampetoid 1 (12mer) is the most hydrophobic (65.1% acetonitrile) and exhibits the lowest CTLR (0.33), while 1$_{10mer}$ is the least hydrophobic (60.9% acetonitrile) and is characterized by the highest CTLR (0.40). The data in Table 5 show that cell selectivity is directly related to CTLR and inversely related to hydrophobicity. The slight reduction in activity of 1$_{10mer}$ against *E. coli* (12.5 µM), (a result of its lowered hydrophobicity), was accompanied by a much larger improvement in its hemolytic activity (HD$_{10}$>200 µM); 1$_{10mer}$ is therefore the most selective of this group (SR$_{E.\ coli}$>16). 1$_{11mer}$ retained antimicrobial activity equivalent to that of 1 (MIC$_{E.\ coli}$ 6.3 µM), but was less selective than 1$_{10mer}$ (SR$_{E.\ coli}$=16). Ampetoid 1 was found to be the least selective (SR$_{E.\ coli}$=3.3). The same trend was observed for selectivity against *B. subtilis* (Table 6).

It is notable that based on the above correlation, 1$_{13mer}$ (CTLR of 0.38) would be expected to have an improved selectivity compared to 1$_{11mer}$ (CTLR=0.36), however this is not the case. On the contrary, ampetoid 1$_{11mer}$ (SR$_{E.\ coli}$=16) is more selective than 1$_{13mer}$ (SR$_{E.\ coli}$=6.8). This may be attributable to the fact that while 1$_{10mer}$, 1$_{11mer}$, and 1 all have a net charge of +4, that of 1$_{13mer}$ is increased to +5. As discussed previously, net charge can affect cell selectivity, particularly against Gram-negative strains. 1$_{11mer}$, with a CTLR of 0.36 and net charge of +4 represents the optimum balance of potent antimicrobial activity and cell selectivity from this group of molecules. However, the selectivity ratios of 1$_{10mer}$ (SR$_{E.\ coli}$>16), 1$_{11mer}$ (SR$_{E.\ coli}$=16), and 1$_{13mer}$ (SR$_{E.\ coli}$=6.8) are all superior to that of 1 (SR$_{E.\ coli}$=3.3).

While proline monomers in naturally-occurring AMPs are known to destabilize α-helical secondary structure and induce the formation of helix-bend-helix motifs, here, proline is well accommodated in the polyproline type-1-like peptoid helical architecture. Because of proline's reduced hydrophobicity compared to Nspe, substituting L-proline for a centrally-located hydrophobic residue in ampetoid 1's sequence (variant called 1-Pro$_6$) was found to lower molecular hydrophobicity and improve selectivity. A family of molecules was designed to evaluate how the relative position and number of proline monomers affects potency and selectivity, while maintaining constant CTLR and helicity. Similar to 1-Pro$_6$, 1-Pro$_3$ and 1-Pro$_9$ have a single proline monomer substituted into the third and ninth positions of the ampetoid 1 sequence, respectively. A fourth variant, 1-Pro$_{3,9}$ incorporates two substituted proline monomers (FIG. 9 and Table 5). The relative hydrophobicities of 1-Pro$_3$, 1-Pro$_6$, and 1-Pro$_9$ are all similar (62.4%-63%), and reduced compared to 1 (65.1%); 1-Pro$_{3,9}$ was found to be even less hydrophobic (58.1%). CD spectroscopy in Tris buffer and both zwitterionic and anionic lipids show that proline-containing ampetoids exhibit a similar degree of helicity as does 1 (FIG. 13).

The activity of these variants against *E. coli* scales with hydrophobicity; 1-Pro$_3$, 1-Pro$_6$, and 1-Pro$_9$ exhibited uniformly reduced potencies against *E. coli* (12.5 µM) compared to peptoid 1 (6.3 µM). The potency of 1-Pro$_{3,9}$ was lessened further against *E. coli* (50 µM). Because these variants also exhibited reduced activity against mammalian cells, selectivity was improved for all the mono-substituted variants (SR$_{E.\ coli}$=5.9-13) compared to 1 (SR$_{E.\ coli}$=3.3).

An intriguing observation regarding the mono-substituted proline-containing variants is that the relative position of the proline monomer in the sequence affected cell selectivity. 1-Pro$_3$, 1-Pro$_6$, 1-Pro$_9$ comprise a family of molecules in which CTLR, net charge, and hydrophobicity are held constant. Moreover, the degree of amphipathicity among these variants is similar, based on the similarity of their CD spectra in both aqueous buffer and lipid environments (FIG. 13). Notably, however, shifting the proline from the N- to the C-terminal region resulted in a progressive increase in selectivity against both erythrocytes and NIH 3T3 cells (Table 6); whereas 1-Pro$_3$ had an HD$_{10}$=74 µM and ID$_{50}$=12 µM, those of 1-Pro$_9$ were 165 µM and 24 µM, respectively. The resultant selectivities monotonically increased from 1-Pro$_3$ (SR$_{E.\ coli}$= 5.9), to 1-Pro$_6$ (SR$_{E.\ coli}$=6.6) to 1-Pro$_9$ (SR$_{E.\ coli}$=13). A similar trend was observed for selectivity ratios against *B. subtilis*. This suggests that ampetoids may have a preferred orientation upon interacting with mammalian cells. If, for example ampetoids interact with mammalian cells preferentially in the C-terminal region, reducing hydrophobicity specifically in that portion of the molecule could impair its activity against mammalian cells and increase selectivity.

Another strategy for improving selectivity relates to a family of ampetoids with less hydrophobic, achiral Npm side chains in place of selected Nspe monomers in ampetoid 1 (FIG. 9 and Table 5). Because molecular chirality of peptoids is derived from the chirality of the side chains rather than that of the backbone, a change in the number of chiral monomers is expected to affect the stability of the secondary structure. This family of molecules, therefore, was designed to effect a range of decreased hydrophobicities and helicities compared to 1, independent of any change in CTLR and net charge constant. 1$_{achiral}$ has all eight Nspe monomers replaced with Npm. Two variants, 1$_{ach}$-Nspe$_2$ and 1$_{ach}$-Nspe$_{12}$ each have only one chiral Nspe monomer at the second and twelfth positions, respectively. Two other ampetoids each contain four achiral Npm's, either aligned along the back molecular face (1-Npm$_{2,5,8,11}$), or distributed across both hydrophobic molecular faces (1-Npm$_{2,3,8,9}$) (FIG. 9).

The hydrophobicities of these compounds ranged from 59.8% for 1$_{achiral}$ to 65.1% for peptoid 1 and generally increased with Nspe content. Moreover, as shown in FIG. 14, the intensity of the helical signal, which is correlated with amphipathicity, decreased with Nspe content. The CD spectrum of 1$_{achiral}$ is flat, which suggests a lack of stable secondary structure and reduced molecular amphipathicity, while that of 1 exhibits the most intense spectral extrema, and correspondingly, the most amphipathic structure. Interestingly, 1$_{ach}$-Nspe$_{12}$ showed slightly more intense CD spectra than isomerically related 1$_{ach}$-Nspe$_2$, an observation that further supports a previous finding that the C-terminal position plays a particularly important role in stabilizing peptoid helical structure[57].

All variants with achiral side chains exhibit activities similar to peptoid 1 against *E. coli* (MIC=6.3-12.5 µM) and *B. subtilis* (MIC=0.78-1.6 µM), yet have substantially higher selectivities for bacteria over mammalian cells (SR$_{E.\ coli}$=6.2-26; SR$_{B.\ subtilis}$=24–235) (Table 6). In general, selectivity increased with Npm content, a monomer substitution for Nspe that simultaneously decreases amphipathicity and hydrophobicity.

This family of variants provides further insight into how hydrophobicity and helicity impact potency and selectivity. Previous studies have shown that variants designed to be less hydrophobic, (via incorporation of more polar histidine-like side chains (e.g. 1-Nhis$_{6,12}$) or less hydrophobic L-proline monomers (e.g. 1-Pro$_6$) improved selectivity, but only at the expense of reduced antimicrobial activity. Indeed, this observation also held true for the proline-containing variants reported herein. The activity and selectivity profiles of four molecules in this family, however, demonstrate clearly that hydrophobicity can be reduced to improve selectivity without compromising antimicrobial activity. Variants 1$_{ach}$-Nspe$_2$, 1$_{ach}$-Nspe$_{12}$, 1-Npm$_{2,5,8,11}$, and 1-Npm$_{2,3,8,9}$) demonstrate antimicrobial activity equivalent to that of 1 (MIC$_{E.\ coli}$=6.3 µM), yet significantly improved selectivities (SR$_{E.\ coli}$=6.2-26) compared to 1 (SR$_{E.\ coli}$=3.3). The most overt difference between using achiral Npm compared to Nhis or L-Pro monomers to lower hydrophobicity is their effect on helicity. While both 1-Nhis$_{6,12}$ and 1-Pro$_6$ exhibited helicity equivalent to that of 1, the substitution of Npm monomers resulted in a progressive decrease in helical stability, as shown in FIG. 14. This suggests that the reducing amphipathicity (correlated with helicity) concomitantly with hydrophobicity provides a means of improving selectivity without compromising antimicrobial activity.

Comparison of the isomeric pairs within this group suggest that the relative position of achiral monomers does not have a significant effect on selectivity. For example, comparison of 1$_{ach}$-Nspe$_2$(SR$_{E.\ coli}$=25, ID$_{50}$=11 µM) and 1$_{ach}$-Nspe$_{12}$ (SR$_{E.\ coli}$=26, ID$_{50}$=15 µM) suggests that selectivity against both erythrocytes and NIH 3T3 cells was unaffected by the position of the one chiral Nspe monomer in the sequence. Comparison of isomeric variants containing equal numbers of Npm and Nspe monomers in different positions (1-Npm$_{2,5,8,11}$ and 1-Npm$_{2,3,8,9}$) suggest that while 1-Npm$_{2,5,8,11}$ (SR$_{E.\ coli}$=14) was more selective against erythrocytes than 1-Npm$_{2,3,8,9}$ (SR$_{E.\ coli}$=6.2), the opposite trend was evident in selectivity against NIH 3T3 cells (ID$_{50}$=6.8 µM and 15 µM, respectively). Taken together, these results suggest that there is no clear relationship between the degree of selectivity and relative position of achiral monomers within the ampetoid sequence.

1$_{enantiomer}$, a variant of peptoid 1 in which all Nspe side chains were replaced with enantiomeric Nrpe monomers, has previously been shown to exhibit left-handed helicity, but antibacterial activities and cell selectivities congruent to those of peptoid 1. Because peptoid secondary structure is dictated by the chirality of its side chains, it is unclear what the resultant secondary structure (and associated activity/selectivity profiles) would be in a peptoid that included both enantiomeric side chains. Moreover, diasteriomeric peptides that contain both D- and L-amino acids were found to exhibit potent, broad-spectrum antimicrobial activity and improved selectivity. Here, variants of 1 can contain equal numbers of Nspe and Nrpe side chains in different arrangements as shown in FIG. 9 and Table 5. 1-Nrpe$_{3,6,9,12}$ and 1-Nrpe$_{2,5,8,11}$ are enantiomers that have four facially-aligned Nspe monomers replaced with enantiomeric Nrpe monomers. 1-Nrpe$_{2,3,5,6}$ has terminally segregated enantiomeric monomers with Nrpe substitutions at positions 2, 3, 5, and 6 in the N-terminal portion of the molecule (FIG. 9).

The antibacterial potencies and cell selectivity profiles of these variants are very similar to that of peptoid 1, despite their disparate secondary structures. FIG. 15 shows that in aqueous buffer as well as both lipid environments, the enantiomeric molecules, 1-Nrpe$_{3,6,9,12}$ and 1-Nrpe$_{2,5,8,11}$, yield mirror image CD spectra. FIG. 15A shows that in buffer, 1-Nrpe$_{3,6,9,12}$ and 1-Nrpe$_{2,5,8,11}$ appear to adopt helical secondary structures, with the overall handedness commensurate with that of the C-terminal monomer. 1-Nrpe$_{2,3,5,6}$, also appears to adopt an overall right-handed spectra, but does not appear to be strongly helical. In both zwitterionic and anionic lipids, however, the CD of the facially-aligned 1-Nrpe$_{3,6,9,12}$ and 1-Nrpe$_{2,5,8,11}$ were markedly altered, suggesting a strong interaction with lipids and a significant change in secondary structure (FIGS. 15B and 15C).

The CD spectal intensity for all Nrpe containing peptoids are significantly reduced compared to that of 1, an observation previously correlated with decreased amphipathicity. However, because the CD spectra corresponding to variants in cell membrane-mimetic lipid environments are not typical of a peptoid helical secondary structure, it is not clear how amphipathicity is affected in these molecules.

The effect of side chain chemistry on cell selectivity, was evaluated with a family of ampetoids that have bulky, hydrophobic, aliphatic Nsdp side chains in place of some or all of the aromatic Nspe monomers in ampetoid 1 (FIG. 9 and Table 5). The previously reported ampetoids containing aliphatic isoleucine-like Nssb side chains were selective, but exhibited reduced activity, particularly against Gram-negative bacterial strains. Incorporating the larger and bulkier aliphatic side chains, 1-methylbutyl glycine (Nsmb), led to increased antibacterial potency, but also reduced selectivity. The dipropyl glycine (Nsdp) (FIG. 9) monomer used in this family of molecules is an isomer of Nsmb and was selected to evaluate if an aliphatic monomer with branched geometry could improve potency while maintaining favorable selectivity. All variants in this group had a CTLR (0.33) and net charge (+4) equivalent to that of 1.

1-Nsdp$_{all}$ has Nsdp substituted at all eight hydrophobic monomers in the peptoid 1 sequence. 1-Nsdp$_{2,5,8,11}$ and 1-Nsdp$_{2,3,8,9}$ are isomers in which half of peptoid 1's Nspe monomers were replaced with aliphatic Nsdp's. As shown in FIG. 9, 1-Nsdp$_{2,5,8,11}$ exhibits four Nsdp monomers aligned along the back molecular face, while the four Nsdp's included in 1-Nsdp$_{2,3,8,9}$ are distributed across both hydrophobic faces. Whereas 1-Nsdp$_{2,5,8,11}$ contains segregated aromatic and aliphatic faces, 1-Nsdp$_{2,3,8,9}$ has a mixture of aromatic and aliphatic monomers in both hydrophobic faces.

The CD spectra of right-handed helical peptoids with chiral, aliphatic side chains have been shown to be distinctly different from those with aromatic side chains in that the most pronounced spectral feature is a maximum at 210 nm. Indeed, the spectrum of 1-Nsdp$_{all}$ exhibits this feature in both aqueous and lipid environments (FIG. 16). 1-Nsdp$_{2,5,8,11}$ and 1-Nsdp$_{2,3,8,9}$ both have spectral characteristics that appear to be a combination of both the aliphatic and aromatic peptoid helical signals. While the resultant "combined" CD spectra appear to be less intensely helical compared to that of 1, it is unclear how the inclusion of aliphatic and aromatic monomers affected molecular amphipathicity; both 1-Nsdp$_{all}$ and 1 exhibit disparate, yet helical CD spectra.

The increase in selectivity of 1-Nsdp$_{all}$ (SR$_{E.\ coli}$>8) was realized at the cost of significantly reduced activity against $E.\ coli$ of (25 µM) in comparison to 1 (SR$_{E.\ coli}$=3.3; MIC$_{E.\ coli}$=6.3 µM). 1-Nsdp$_{all}$ was highly potent against $B.\ subtilis$ (0.78 µM), resulting in a selectivity ratio of 256 (Table 6).

The sequences containing equal numbers of aromatic and aliphatic monomers, 1-Nspd$_{2,5,8,11}$ and 1-Nsdp$_{2,3,8,9}$, exhibited slightly reduced antimicrobial activity (MIC$_{E.\ coli}$=12.5 µM) and improved selectivity (SR$_{E.\ coli}$=9.7 and 6.2, respectively) compared to 1 (MIC$_{E.\ coli}$=6.25 SR$_{E.\ coli}$=3.3). While the slightly reduced hydrophobicity could be in part responsible for the improved selectivity, comparison with other variants suggests that the aliphatic side chain chemistry also plays an important role in its activity profile. Unlike what has been observed in some sequences that contain all aromatic hydrophobic monomers, the incorporation of aliphatic side chains appears to improve selectivity, but only at the expense of antimicrobial activity. For example variants 1-Npm$_{2,3,8,9}$ (63.3% acetonitrile), 1-Npm$_{2,5,8,11}$ (63.6% acetonitrile) and 1$_{11mer}$ (63.5% acetonitrile) all exhibit hydrophobicities comparable to that of 1-Nsdp$_{2,5,8,11}$ (63.8% acetonitrile). The balance of the antimicrobial activity and selectivity profiles of 1-Nsdp$_{2,5,8,11}$, however, is less optimal than for sequences containing only these aromatic side chains; compared with these three molecules (MIC$_{E.\ coli}$=6.3 µM, SR$_{E.\ coli}$=6.2-16) the antimicrobial activity of 1-Nsdp$_{2,5,8,11}$ is reduced (MIC$_{E.\ coli}$=12.5 µM) and selectivity (SR$_{E.\ coli}$=9.7) comparable. The overall hydrophobicities of these three molecules (63.2%-64.7%) were slightly reduced compared to 1 (65.1%). The reduced hydrophobicity of 1-Nsdp$_{all}$ (63.2%) could in part be responsible for its reduced activity, however the lack of aromatic side chains may also play a role. Variants containing both aliphatic and aromatic side chains appear to provide a balance of low antimicrobial activity (MIC$_{E.\ coli}$=12.5 µM) and improved selectivity compared to 1 (SR$_{E.\ coli}$=6.2-12): 1-Nsdp$_{2,3,8,9}$ (SR$_{E.\ coli}$=6.2-12), and 1-Nsdp$_{2,5,8,11}$ (SR$_{E.\ coli}$>9.7).

The antimicrobial activity of selected ampetoids and comparator peptide pexiganan was tested against 16 clinically-relevant BSL2 bacterial strains. The panel of bacterial strains included seven Gram-negative species (*Proteus vulgaris, Pseudomonas aeruginosa, Proteus mirabilis, Klebsiella pneumonia, Enterobacter aerogenes, Escherichia coli*, and *Serratia marcescens*) and nine strains from three Gram-positive species (*Staphylococcus aureus, Enterococcus faecalis,* and *Enterococcus faecium*). Ampetoids 1, 1-Pro$_6$, 1-Pro$_9$, 1$_{achiral}$, 1-Npm$_{2,5,8,11}$, and 1-Nsdp$_{2,5,8,11}$ were tested against these organisms. The MICs (expressed in µg/mL) are shown in Table 7A and corresponding selectivity ratios (quotient of 10% hemolytic dose and MIC) are presented in Table 7B.

The activities of the six peptoids tested were all similar to that those of pexiganan against *P. vulgaris* (MIC=32-64 µg/mL), *K. pneumoniae* (MIC=8-16 µg/mL), and *E. coli* (4-16 µg/mL). Against *P. mirabilis* and *S. marcescens*, pexiganan and all peptoids tested were inactive (MIC≧128). The activities of ampetoids tested against BSL2 Gram-positive strains, however, compared very favorably to those of pexiganan. The MIC of pexiganan against the six strains of *S. aureus* tested ranged from 8-64 µg/mL, whereas those of all the peptoids tested ranged from 4-16 µg/mL. Interestingly, 1 was uniquely active against both strains of *E. faecalis* (MIC=4-8 µg/mL), compared to other ampetoids (MIC=8-64 µg/mL) and pexiganan (MIC=32-128 µg/mL). All compounds were equally potent against *E. faecium* (MIC=4 µg/mL).

TABLES 7A--B

Broad spectrum activity and selectivity of selected ampetoids and pexiganan.
(A) MICs (in μg/mL) of selected ampetoids against BSL2 microbial strains. (B) Selectivity ratios are defined as the 10% hemolytic dose divided by the MIC for the organism of interest. The hemolytic dose (μg/mL) of each compound (Table 2-2) was multiplied by its molecular weight (Table 2-1) to calculate the selectivity ratio.

A

| Bacterial organism | Minimum inhibitory concentration (MIC) (μg/mL) | | | | | | |
|---|---|---|---|---|---|---|---|
| | Pex. | 1 | 1-$Pro_6$ | 1-$Pro_9$ | $1_{achiral}$ | 1-$Npm_{2,5,8,11}$ | 1-$Nsdp_{2,5,8,11}$ |
| *P. vulgaris* ATCC 49132 | 32 | 32 | 32 | 64 | 32 | 64 | 32 |
| *P. aeruginosa* ATCC 27853* | 4 | 8 | 32 | 32 | 16 | 64 | 16 |
| *P. mirabilis* ATCC 35659 | >128 | >128 | >128 | >128 | >128 | >128 | >128 |
| *K. pneumoniae* ATCC 33495 | 8 | 16 | 16 | 16 | 8 | 16 | 8 |
| *E. aerogenes* ATCC 35029 | 32 | 16 | 128 | 64 | 128 | 64 | 32 |
| *E. coli* ATCC 25922* | 8 | 4 | 16 | 8 | 16 | 8 | 8 |
| *S. marcescens* ATCC 13880 | >128 | 128 | >128 | >128 | >128 | >128 | >128 |
| *S. aureus* | | | | | | | |
| ATCC 29213* | 32 | 4 | 8 | 16 | 8 | 8 | 8 |
| VAN1[§†] | 16 | 4 | 8 | 8 | 8 | 8 | 8 |
| VAN2[§†] | 8 | 4 | 8 | 8 | 8 | 8 | 8 |
| NRS100 (COL)[§] | 16 | 4 | 8 | 8 | 8 | 8 | 8 |
| NRS119[‡] | 64 | 4 | 16 | 16 | 16 | 16 | 16 |
| NRS120[‡] | 64 | 8 | 16 | 16 | 16 | 16 | 16 |
| *E. faecalis* | | | | | | | |
| ATCC 29212 | 32 | 4 | 8 | 8 | 16 | 8 | 8 |
| 99 | 128 | 8 | 64 | 64 | 64 | 64 | 64 |
| *E. faecium* 106* | 4 | 4 | 4 | 4 | 4 | 4 | 4 |

B

| Bacterial organism | Selectivity ratio (SR) | | | | | | |
|---|---|---|---|---|---|---|---|
| | Pex. | 1 | 1-$Pro_6$ | 1-$Pro_9$ | $1_{achiral}$ | 1-$Npm_{2,5,8,11}$ | 1-$Nsdp_{2,5,8,11}$ |
| *P. vulgaris* ATCC 49132 | 5.7 | 1.2 | 4.6 | 5.4 | 9.8 | 2.4 | 5.8 |
| *P. aeruginosa* ATCC 27853* | 46 | 4.8 | 4.6 | 9.0 | 19 | 2.4 | 12 |
| *P. mirabilis* ATCC 35659 | <1.4 | <0.3 | <1.1 | <2.3 | <2.4 | <1.2 | <1.5 |
| *K. pneumoniae* ATCC 33495 | 23 | 2.4 | 9.1 | 18 | 39 | 9.6 | 23 |
| *E. aerogenes* ATCC 35029 | 5.7 | 2.4 | 1.1 | 5.4 | 2.4 | 2.4 | 5.8 |
| *E. coli* ATCC 25922* | 23 | 9.5 | 9.1 | 36 | 19 | 19 | 23 |
| *S. marcescens* ATCC 13880 | <1.4 | 0.3 | <1.1 | <2.3 | 2.4 | <1.2 | <1.5 |
| *S. aureus* | | | | | | | |
| ATCC 29213* | 5.7 | 9.5 | 18 | 18 | 39 | 19 | 23 |
| VAN1[§†] | 11 | 9.5 | 18 | 36 | 39 | 19 | 23 |
| VAN2[§†] | 23 | 9.5 | 18 | 36 | 39 | 19 | 23 |
| NRS100 (COL)[§] | 11 | 9.5 | 18 | 36 | 39 | 19 | 23 |
| NRS119[‡] | 2.8 | 9.5 | 9.1 | 18 | 19 | 9.6 | 12 |
| NRS120[‡] | 2.8 | 4.8 | 9.1 | 18 | 19 | 9.6 | 23 |
| *E. faecalis* | | | | | | | |
| ATCC 29212 | 5.7 | 9.5 | 18 | 36 | 19 | 19 | 23 |
| 99 | 1.4 | 4.8 | 2.3 | 5.4 | 4.9 | 2.4 | 2.9 |
| *E. faecium* 106* | 46 | 9.5 | 36 | 72 | 79 | 38 | 46 |

Notes:
*indicates NCCLS recommended standard strain;
[§]indicates methicillian-resistant *S. aureus* (MRSA) strain;
[†]indicates vancomycin-resistant strain;
[‡]indicates linezolid-resistant strain.

The selectivity ratios presented in Table 7B show that against most Gram-negative bacterial species, at least one ampetoid had greater selectivity compared to pexiganan; the most favorable selectivity ratio against each Gram-negative species is shown in boldface type in Table 7B. $1_{achiral}$, 1-Pro$_9$, and 1-Nsdp$_{2,5,8,11}$ were the most selective against selected MDR bacterial strains. Against Gram-positive strains, ampetoids more consistently demonstrated improved selectivity compared to pexiganan or ampetoid 1. Against all *S. aureus* strains, for example, the selectivity ratios of pexiganan ranged from 2.8-23, ampetoid 1 ranged from 4.8-9.5, and those of the panel of more selective ampetoids ranged from 9.1-39.

As shown above, ampetoids are a new class of AMP mimics that have been shown to exhibit potent, broad-spectrum antimicrobial activity and appear to use mechanisms of action similar to their natural counterparts. An understanding of factors that influence cell selectivity can be used in the context of corresponding pharmaceutical agents. Accordingly, a library of ampetoids was designed to explore how and to what extent various physicochemical properties and structural motifs influenced their cell selectivity.

To broaden understanding of how ampetoids may be affecting different types of mammalian cells, the hemolytic dose as well as the metabolic inhibitory dose was determined against NIH 3T3 mouse fibroblast cells. While the hemolytic and inhibitory activities exhibited similar trends for many ampetoids, the hemolytic dose was consistently higher than the inhibitory dose for the same compound. This is a trend that has also been reported for pexiganan as well as other AMP mimics. It is possible that the disparity between the hemolytic and inhibitory doses is due in part to differences in membrane composition between the two cell types. The cholesterol content of erythrocyte membranes, for example is approximately 230 µg/mg protein, whereas NIH 3T3 cholesterol content has been reported as only 30.5 µg/mg protein. The increased cholesterol content of erythrocytes may affect the rigidity of the membrane and offer increased resistance to membrane-active antimicrobial agents compared to NIH 3T3 cells.

Another disparity between hemolysis and MTS assays is that they differ in terms of the measure used to quantify cytotoxicity; while hemolysis measures the ampetoid dose needed to lyse erythrocytes, the MTS assay quantifies the dose needed to inhibit cellular metabolism, measured indirectly by the amount of NADH produced by the cell population. It is reasonable to expect, therefore that a dose needed to lyse a cell membrane would not necessarily be equivalent to the dose required to inhibit cellular metabolism. Whereas lysis implies membrane disruption activity, interference with cellular metabolism implies intracellular targets. While animal testing would be required to determine a true therapeutic index for these molecules, hemolysis and MTS assay results together suggest that the relative effect of many ampetoids against both cell types may be similar.

This library of ampetoids was designed to include members that exhibit a variety of structural motifs and possess physicochemical properties that span a wide range of values. Different ampetoids demonstrated promising activities against the various Gram-negative strains, but were most potent against K pneumonia (ATCC 33495) and *E. coli* (ATCC 25922). It is particularly notable that all 26 ampetoid variants were consistently very potent against the Gram-positive screening organism, *B. subtilis*. The broad-spectrum testing results of selected ampetoids against MDR strains of *S. aureus, E. faecalis*, and *E. faecium* show that ampetoids are also potent against MRSA (4-8 µM) as well as vancomycin- and linezolid-resistant organisms (4-8 µM and 4-16 µM, respectively). The corresponding selectivity ratios of $1_{achiral}$ (19-39) and 1-Pro$_9$ (18-36) against MDR *S. aureus* strains are particularly favorable compared to those of pexiganan (2.8-23) or ampetoid 1 (4.8-9.5). The burden of MDR Gram-positive infections on the healthcare system is significant and only increasing; these results suggest that ampetoids can be a viable alternative to conventional therapies to address this unmet clinical need.

Structure-activity studies have shown that the antibacterial activity and selectivity profiles of ampetoids are governed by the physicochemical properties that, in a similar manner, dictate the activity and selectivity of AMPs. The structure-activity relationships gleaned from these studies not only provide further evidence to re-affirm these findings in ampetoids, but also provide additional insight into principles that influence how more subtle changes related to the number, sequence position, arrangement and chemical structure of specific structural moieties influence activity and selectivity.

Potent, but non-selective AMPs and ampetoids tend to be hydrophobic and adopt well-defined amphipathic structures, while more selective AMPs and ampetoids are typically highly cationic, exhibit only moderate hydrophobicity, and are often less amphipathic. As discussed previously, the activity and selectivity results of this study, which included several new ampetoid sequences, re-affirm these general relationships in several ways: (1) Comparison of the less amphipathic, more selective $1_{scr}$ to 1; (2) Comparison of the highly charged, less amphipathic variants (1-Nlys$_{5,11}$, 1B-Nlys$_{4,10}$, and 1B$_{15mer}$-Nlys$_{4,10}$, 1B-Nlys$_{4,6,10}$ and 1B$_{15mer}$-Nlys$_{4,6,10}$) compared to 1, (3) Comparison of less hydrophobic proline-containing variants (1-Pro$_3$, 1-Pro$_6$, 1-Pro$_9$, 1-Pro$_{3,9}$) to 1 (4) Comparison among achiral variants ($1_{achiral}$, $1_{ach}$-Nspe$_2$, $1_{ach}$-Nspe$_{12}$, 1-Npm$_{2,3,8,9}$, 1-Npm$_{2,5,8,11}$), which exhibit a range of hydrophobicities and amphipathicities that scale with selectivity. Taking a closer look at more specific structural characteristics of the ampetoids included in this study, the influence of subtle molecular changes on activity and selectivity can be elucidated.

Comparison among the mono-substituted proline monomers suggests that the position of monomers along the length of the molecule and can impact selectivity. The mono-substituted proline monomers exhibited progressively increased selectivity as the less hydrophobic proline monomer was moved from the N-terminal toward the C-terminal region.

Trends observed in the selectivity profiles of sequence register variants (1, 1B and 1C) as well as length variants, $1_{13mer}$, suggest that monomer position with respect to the termini also influences selectivity. All variants are similarly potent against *E. coli*: the MIC$_{E.\ coli}$ of 1, 1B, and 1C was 6.3 µM, while that of $1_{13mer}$ was improved by one dilution (3.1 µM). While 1 and 1C each have one charged Nlys monomer at the N and C-termini, respectively, 1B has hydrophobic Nspe monomers at both termini. Conversely, $1_{13mer}$ has charged Nlys monomers at both terminal positions. Consider these molecules in two groups: (1) those with both termini charged or hydrophobic (1B and $1_{13mer}$), and (2) those with one charged and one hydrophobic terminus (1 and 1C). Interestingly, the hydrophobicity of those with dissimilar termini, 1 (65.1% acetonitrile) and 1C (64.8% acetonitrile) is greater than that of variants with like monomers at terminal positions, 1B (63.4% acetonitrile) and $1_{13mer}$ (62.8% acetonitrile). Correspondingly, the selectivity of the less hydrophobic variants 1B and $1_{13mer}$ (SR$_{E.\ coli}$=6.8-8.7, SR$_{B.\ subtilis}$=27-34) is improved compared to that of 1 and 1C(SR$_{E.\ coli}$=3.3-4.0, SR$_{B.\ subtilis}$=13-16). This suggests that having similarly charged termini (either both hydrophobic or both positively charged) reduces molecular hydrophobicity and results in an improvement in selectivity. This could be related to a similar phenomenon reported for antimicrobial peptide analogs of magainins, which found that the relative position of hydrophobic monomers in the sequence can impact resultant hydrophobicity and cell selectivity. These results indicate that a strategy for improving selectivity, while maintaining antimicrobial activity, is to design the sequence with similarly charged or similarly hydrophobic terminal monomers.

As discussed previously, the achiral family of variants provide evidence that suggests the incorporation of achiral Npm hydrophobic monomers in place of chiral Nspe monomers is another means of improving selectivity without compromising antimicrobial activity. Variants in which as many as seven of the eight Nspe's in ampetoid 1's structure exhibited equivalent activity and significantly improved selectivity. It appears that the decrease amphipathicity that occurs concomitantly with increased Npm content results in a favorable selectivity profile. It is possible that the less rigid structure of ampetoids with increased achiral monomer content is less able to penetrate the rigid cell membranes of mammalian cells.

A third way in which this library of compounds was designed to affect selectivity is through increased CTLR. The increased charge density variants, with CTLRs in the range of 0.47-0.58 (compared to 0.33 for ampetoid 1), were at best mildly active against $E.\ coli$ (MIC=50 to >100 μM). Length variants, however, which were designed to effect a change in CTLR over a lower range (0.33-0.40). Of these variants, $1_{11mer}$ was found to exhibit the most optimum balance of CTLR (0.36) and sufficient hydrophobicity to permeabilize bacterial membranes (63.5%) at a low minimum inhibitory concentrations ($MIC_{E.\ coli}$=6.3 μM).

Two other means of reducing hydrophobicity, substituting in L-proline content or aliphantic Nsdp monomers, are less favorable because they improve selectivity at the expense of antimicrobial activity against Gram-negative bacteria. The addition of one proline monomer (1-Pro$_3$, 1-Pro$_6$, and 1-Pro$_9$, $MIC_{E.\ coli}$=12.5 μM) and two proline monomers (1-Pro$_{3,9}$, $MIC_{E.\ coli}$=50 μM) progressively decreased activity compared to that of ampetoid 1 ($MIC_{E.\ coli}$=6.3 μM). Molecules with four (1-Nsdp$_{2,3,8,9}$ and 1-Nsdp$_{2,5,8,11}$, $MIC_{E.\ coli}$=12.5 μM) and eight (1-Nsdp$_{all}$, $MIC_{E.\ coli}$=25 μM) aliphatic monomers exhibited a similar trend in reduced antimicrobial activity.

Another observation is evident from the characterization of $1_{achiral}$, 1-Nrpe$_{3,6,9,12}$, and 1-Nrpe$_{2,5,8,11}$, which suggests that ampetoids can exhibit potent antimicrobial activity without necessarily adopting a stable helical secondary structure. As the name suggests, $1_{achiral}$ is devoid of any chiral monomers and is thus not optically active; the resultant CD spectra in aqueous buffer and lipid environments is flat (FIG. 13). While it is conceivable that $1_{achiral}$ could transiently adopt a helical structure of either handedness, there does not appear to be external or intrinsic force to stabilize its structure. 1-Nrpe$_{3,6,9,12}$, and 1-Nrpe$_{2,5,8,11}$, on the other hand, are enantiomeric molecules that contain equal numbers of Nspe and Nrpe hydrophobic aromatic side chains. Interestingly, the overall chirality of these monomers appears to be dictated by the chirality of the monomer in the 12$^{th}$ position, a finding commensurate with the observation that $1_{ach}$-NSpe$_{12}$ exhibits a larger degree of right-handed chirality than does $1_{ach}$-Nspe$_2$. This provides further evidence that the C-terminal monomer heavily influences structural stability. In buffer, both of these variants produce CD spectra that resemble that of a peptoid polyproline-type-1-like structure with the extrema normally at 202 nm blue-shifted to approximately 195 nm (FIG. 15). In neutral POPC/cholesterol lipids, however, the extrema at 220 nm is greatly diminished, and in POPE/POPG SUVs, this feature is completely eliminated. This marked change in CD spectra suggests that 1-Nrpe$_{3,6,9,12}$, and 1-Nrpe$_{2,5,8,11}$ interact strongly with both of these lipid mixtures such that their overall structure is significantly altered. Taken together, it is interesting that $1_{achiral}$, which appears to lack a stable secondary structure, as well as 1-Nrpe$_{3,6,9,12}$, and 1-Nrpe$_{2,5,8,11}$, which have a CD spectra in lipids that are distinct from that of a canonical peptoid polyproline-type-1-like, are all equally potent as ampetoid 1 against $E.\ coli$ (MIC=6.3 μM). A stable helical secondary structure does not appear to be necessary for ampetoid antimicrobial activity. This finding that a stable helical secondary structure does not appear to be necessary for ampetoid antimicrobial activity goes beyond previous findings, which suggested that helicity is important only as a means of organizing an amphipathic structure.

A pair of molecules was designed to evaluate if the facial segregation aliphatic and aromatic hydrophobic monomers impacts selectivity. While 1-Nsdp$_{2,5,8,11}$ has four substituted aliphatic monomers aligned along molecular faces, 1-Nsdp$_{2,3,8,9}$ has a mixture of aliphatic and aromatic hydrophobic monomers on both faces (FIG. 9). The facially-aligned isomer 1-Nsdp$_{2,5,8,11}$ (SR$_{E.\ coli}$=9.7; SR$_{B.\ subtilis}$=142) was more selective than its facially-distributed counterparts (1-Nsdp$_{2,3,8,9}$-SR$_{E.\ coli}$=6.2, SR$_{B.\ subtilis}$=99). While these isomers exhibit similar net charges (both+4), CTLRs (both 0.33), and hydrophobicities (63.8%-64.7% acetonitrile), a notable difference between them is that while the arrangement of hydrophobic monomers on 1-Nsdp$_{2,5,8,11}$, preserved one wholly aromatic face, that of 1-Nsdp$_{2,3,8,9}$ exhibits no completely aromatic face. It has been shown previously that the inclusion of at least one aromatic face increases helical stability[57]; the more intense helicity of 1-Nsdp$_{2,5,8,11}$ compared to 1-Nsdp$_{2,3,8,9}$ in both zwitterionic and anionic lipid mixtures supports this observation (FIG. 16). This suggests that preservation of at least one ampetoid aromatic face may increase its selectivity independent of changes in other physiocochemical parameters.

The most promising therapeutic agents exhibit are highly potent against bacteria and are nontoxic to mammalian cells. This relationship is depicted graphically in FIG. 17, in which the hemolytic dose is plotted versus the $E.\ coli$ (FIG. 17A) and $B.\ subtilis$ (FIG. 17B) minimum inhibitory concentrations for selected peptoids. Peptoid 1 and pexiganan are depicted by red markers for reference. Those peptoids located in the lower right coordinate space have the most promising therapeutic potential. Many compounds reported herein exhibit more favorable activity profiles than peptoid 1 and pexiganan. It is most notable that the increased charge density variants, which were completely non-hemolytic, demonstrated a marked improvement in activity profile against Gram-positive $B.\ subtilis$.

As shown, ampetoids are a promising class of AMP mimics that exhibit potent, broad-spectrum activity, particularly against many multi-drug resistant Gram-positive organisms. Of the 26 sequences presented here, 17 demonstrate improved selectivity for $E.\ coli$ compared to the basis sequence, 1. The structure-activity relationships derived from this library of compounds reaffirm and extend the analogy between the mechanism of action of AMPs and ampetoids. Selective ampetoids tended to be only moderately hydrophobic and amphipathic, while non-selective ampetoids were highly hydrophobic and exhibit more highly amphipathic structures. The relationships among ampetoid variants in this library also point to the effects of how more subtle changes in sequence, side chain chemistry, and monomer position effect selectivity. Three strategies to improve ampetoid selectivity without compromising selectivity include (1) Positioning of similarly cationic or hydrophobic monomers at the sequence terminal positions, (2) Inclusion of hydrophobic achiral Npm monomers in place of Nspe monomers (3) Optimizing the CTLR while retaining sufficient hydrophobicity to permeabilize bacterial cell membranes. Two approaches, specifically designed to reduce hydrophobicity effected the desired outcome of improving selectivity, but only at the cost of reduced antimicrobial activity. This less optimal activity profile resulted from (1) Substitution of less hydrophobic L-proline monomers as well as (2) Substitution of aliphatic Nsdp monomers. Interestingly, while the relative position along the helix of some monomers played a role in selectivity (e.g. monoproline substituted variants), this was not always the case (e.g. achiral variants). The preservation of at least one aromatic face may also play a role in increasing selectivity. Lastly, thus study provides evidence that antimicrobial activity can be maintained in ampetoids which lack a stable secondary structure ($1_{achiral}$) or appear to adopt a secondary structure different from that of the canonical peptoid helix (1-Nrpe$_{2,5,8,11}$ and 1-Nrpe$_{3,6,9,12}$). Because peptoids are sequence-specific biopolymers that can be made from a diversity of primary amines, it is conceivable that ampetoid potency and selectivity could be finely tuned to fight specific, clinically-relevant organisms. The design heuristics established herein may aid in the design of potent, yet selective, future generations of ampetoids.

EXAMPLES OF THE INVENTION

The following non-limiting examples and data illustrate various aspects and features relating to the compounds and/or methods of the present invention, including the preparation of various helical peptoid compounds, as are available through the synthetic methodology described herein. In comparison with the prior art, the present peptoid compounds provide results and data which are surprising, unexpected and contrary to the prior art. While the utility of this invention is illustrated through the use of several compounds, it will be understood by those skilled in the art that comparable results are obtainable with various other compounds, peptoid lengths, residue sequences and/or N-pendant side chains, as are commensurate with the scope of this invention.

Example 1

Synthesis and Purification

Peptoids were synthesized either using an ABI 433A peptide synthesizer or a parallel synthesis robot on Rink amide resin according to the submonomer method. (See, e.g., Zuckermann, R. N., Kerr, J. M., Kent, S. B. H., & Moos, W. H. (1992) *J. Am. Chem. Soc.*, 114, 10646-10647.) Briefly, the amide on the nascent chain is bromoacetylated, followed by $S_N2$ displacement of bromide by a primary amine to form the side chain. Peptides were synthesized using standard Fmoc chemistry. Following synthesis, peptoids and peptides were cleaved and deprotected in trifluoroacetic acid (TFA):triisopropylsilane:water (95:2.5:2.5 by vol.) for 10 min. Compounds were purified to >97% homogeneity by RP-HPLC on a C18 column with a linear acetonitrile/water (0.1% TFA) gradient. Mass spectrometry was used to confirm the molecular weight of the purified product.

Figure 8:
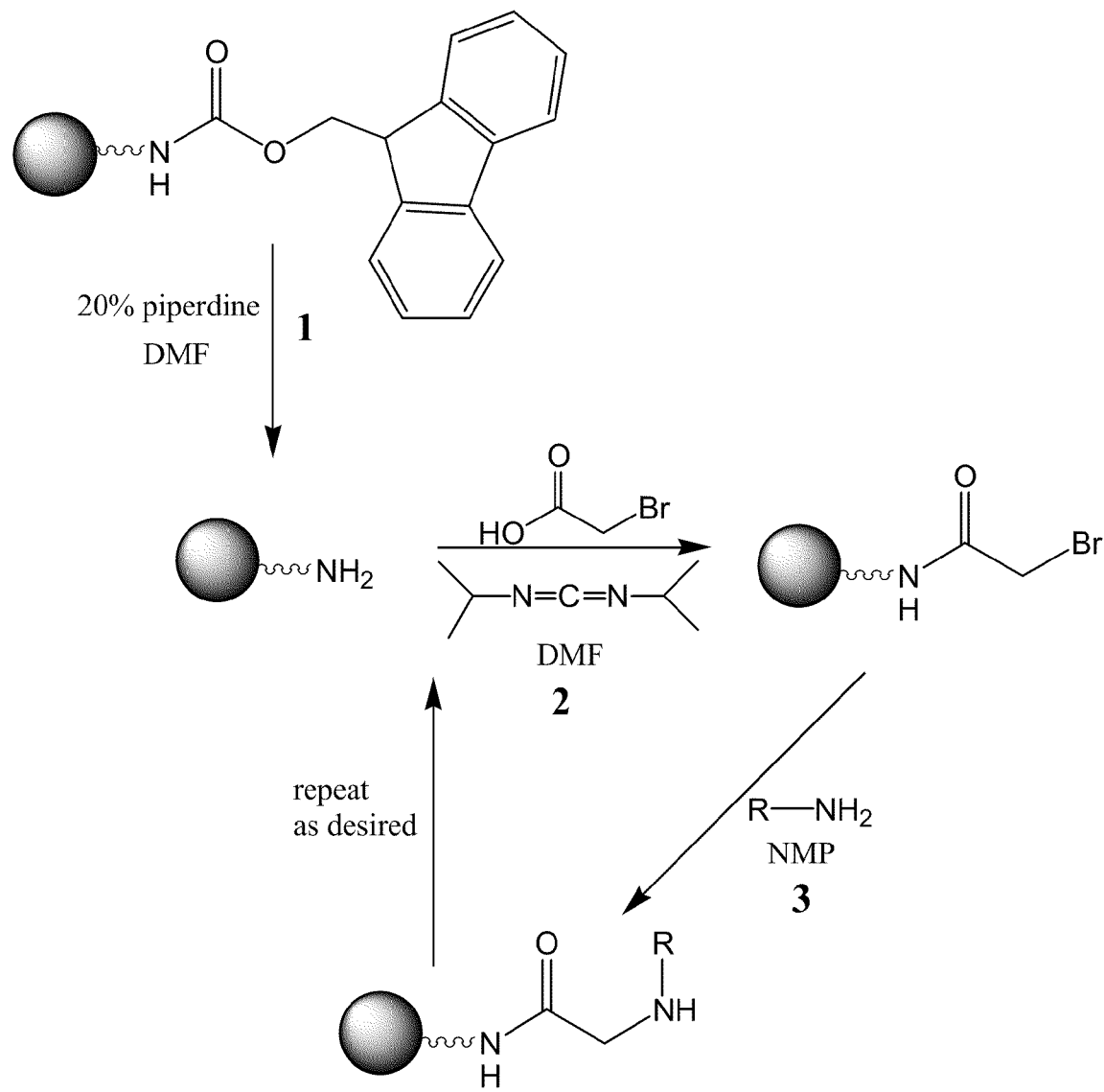
FIG. 8. A schematic illustration of the sub-monomer synthetic protocol for polypeptoids. Steps 2 and 3 are simply repeated for the addition of each monomer unit. Once the full polypeptoid has been synthesized, it is cleaved off the resin with trifluoroacetic acid and purified by reversed-phase HPLC.

The submonomer method is illustrated graphically in FIG. 8. Each monomer of the growing peptoid polymer is assembled in two steps, using two readily available submonomeric units. Rink amide resin is bromoacetylated, using diisopropylcarbodiimide-activated bromoacetic acid. Next, the bromoacetylated resin undergoes $S_N2$ displacement of bromide by a primary amine, which introduces the desired side chain. Hundreds of potential amine submonomers and corresponding side chains are commercially or synthetically available. As a result, (1) the synthesis of peptoids by the submonomer protocol provides facile access to sequences of greater chemical diversity than readily obtained via the monomer approach; and (2) more directly applicable to this invention, the biomimetic peptoids are limited only by sequence order, length and/or N-pendant side chain structure sufficient to provide desired antibacterial activity.

More specifically, Rink Amide resin (4-(2',4'-Dimethoxyphenyl-(9-fluorenylmethyloxycarbonyl)-aminomethyl)-phenoxy resin, 0.25 mmol; Novabiochem) can be initially swelled for 30 min in $CH_2Cl_2$. Following the resin swelling, the 9-fluorenylmethyloxycarbonyl (Fmoc) protecting group is removed by treatment with 20% piperidine solution in 1-methyl-2-pyrrolidone (NMP). The resin-bound deprotected amine is then bromoacetylated by reaction with 4.2 ml of 1.2 M bromoacetic acid (50 mmol) in N,N-dimethylformamide (DMF) and 1.0 ml (11 mmol) neat N,N'-diisopropylcarbodiimide (DIC) for 60 minutes at room temperature with constant mixing. Next, the resin is rinsed with DMF (3×10 ml), followed by NMP rinses (3×10 ml). 6 ml of a 1 M solution (6 mmol) of a primary amine "submonomer" (see below) in either NMP or $CH_2Cl_2$ reacted with the resin-bound bromoacetyl moiety, displacing bromide. A protected submonomer (N-tert-butoxycarbonyl-1,4-butanediamine) is synthesized in order to create the N-(4-aminobutyl)glycine residue (Nlys). The resin is then rinsed again with NMP (3×10 ml) followed by DMF (3×10 ml). The product of these two reactions generates a peptoid "residue", the identity of which depended upon the submonomer amine employed. Peptoids are elongated by this submonomer method until the desired chain-length was attained.

Following synthesis, peptoid oligomers can be cleaved from the resin, simultaneously removing the tert-butoxycarbonyl (Boc) protecting group from Nlys residues, by treatment with 10 ml 2,2,2-trifluoroacetic acid (TFA)/triisopropylsilane/$H_2O$ (95:2.5:2.5 by volume) for 30 min. The cleavage mixture is then diluted with 25 ml 50% aqueous acetonitrile, frozen, and lyophilized. Dilution and lyophilization is repeated twice more in order to remove excess TFA. Subsequent to cleavage, peptoids are each purified to >97% homogeneity by preparative scale reversed-phase HPLC using a Waters Prep LC 4000 system, with Waters 2487 dual-wavelength UV detection, and gradient elution (solvent A, 0.1 vol % trifluoroacetic acid (TFA) in water; solvent B, 0.1 vol % TFA in acetonitrile) through a Vydac (Hysperia, Calif.) 214TP101550 C4 peptide/protein column (10-15 µm, 300 Å, 5×25 cm). Following prep HPLC, peptoid purities and crude yields were determined from analytical scale HPLC, performed with a Waters 2695 Separations Module with a Waters 2487 dual-wavelength UV detector and gradient elution (solvent A, 0.1 vol % TFA in water; solvent B, 0.1 vol % TFA in acetonitrile) through a Vydac C4 214TP53 peptide/protein column (5 µm, 300 Å, 3.2×250 mm). The precise gradient employed for HPLC depended on the identity and hydrophobicity of the oligomer in question. The composition of the HPLC solvent at gradient elution is an indication of this hydrophobicity, and is provided in Table 1. All analytical HPLC was performed at 0.5 ml/min flow and 58° C. Preparative HPLC was performed at 50 ml/min flow and room temperature.

Such synthesis and characterization are also described in U.S. Pat. No. 6,887,845, the entirety of which is incorporated herein by reference. As illustrated therein and as would be understood by those skilled in the art made aware of this invention, the present N-substituted glycine residues and resulting peptoid compounds are limited only by synthetic or commercial availability of the corresponding amine reagents.

Example 2

SUV Preparation

Lipid mixtures, either POPE/POPG (7:3) or POPC/CH (1:1), were dissolved in chloroform, dried under $N_2$, and lyophilized overnight. The resulting lipid film was hydrated with 10 mM Tris-HCl (pH 7.4) at 40° C. for one hour. The resulting multilamellar vesicle suspension was vortexed, then sonicated at 40° C. until the solution clarified to make SUVs, which were used within 6 hours.

Example 3

CD Spectroscopy

CD measurements were performed on a Jasco 715 spectropolarimeter, using a quartz cylindrical cell (path length=0.02 cm), with 50 µM peptoid in 10 mM Tris-HCl (pH 7.4) and 5 mM lipids when SUVs were used. Scans were conducted at 100 nm/min between 185 and 280 nm with 0.2 nm data pitch, 1 nm bandwidth, 2 s response, 100 mdeg sensitivity, and 40 accumulations.

Example 4

Antibacterial Assays

MICs were determined according to CLSI M7-A6 protocols in a 96-well microtiter plate. In test wells, 50 µL bacterial inoculum ($5 \times 10^5$ CFU/ml) in Mueller-Hinton broth (MHB) was added to 50 µL peptoid solution in MHB (prepared by 1:2 serial dilutions). Positive controls contained 50 µL inoculum and 50 µL MHB without peptoid. The MIC was defined as the lowest concentration of peptoid that completely inhibited bacterial growth after incubation at 35° C. for 16 h. MIC values reported were reproducible between three independent experimental replicates, each consisting of two parallel trials. Broad-spectrum antimicrobial susceptibility testing was performed against BSL2 pathogens by Nova Biologicals, Inc. (Conroe, Tex.).

Example 5

Antifungal Assays

MICs were determined using the broth microdilution assay given by CLSI M27-A2 protocols. *Candida albicans* (SC5314) was grown on Sabouraud dextrose agar for 24 hours at 30° C. Cells were suspended in 0.145 M saline, and the cell concentration was adjusted to $3 \times 10^6$ cells/mL. After adjusting the cell concentration, the suspension was diluted 1:1000 with RPMI 1640 (with L-glutamine and without sodium bicarbonate, Invitrogen) buffered with 0.145 M 3-(N-morpholino) propanesulfonic acid (MOPS). Two-fold serial dilutions of peptoids, peptides, and amphotericin B (Calbiochem) were prepared in RPMI 1640 and mixed with an equal volume of the cell suspension in 96-well plates. The final testing concentrations for the peptoids and peptides were 0.20 to 100 µM, and concentrations for amphotericin B were 0.031 to 16 µM. Growth controls and sterility controls were also included. Plates were incubated for 48 hours at 35° C., and growth of *C. albicans* was inspected visually to determine the MICs. The MIC for each compound was defined as the lowest concentration with no visible fungal growth. Experiments were performed in duplicate on two separate days.

Example 6

Hemolysis Assays

Erythrocytes were isolated from freshly drawn, heparanized human blood and resuspended to 20 vol % in PBS (pH 7.4). In a 96-well microtiter plate, 100 µL erythrocyte suspension was added to 100 µL peptoid solution in PBS (prepared by 1:2 serial dilutions), or 100 µL PBS in the case of negative controls. 100% hemolysis wells contained 100 µL blood cell suspension with 100 µL 0.2 vol % Triton X-100. The plate was incubated for 1 h at 37° C., then each well was diluted with 150 µL PBS. The plate was then centrifuged at 1200 g for 15 min, 100 µL of the supernatant from each well transferred to a fresh microtiter plate, and $A_{350}$ measured. Percent hemolysis was determined as $(A-A_0)/(A_{total}-A_0) \times 100$, where A is the absorbance of the test well, $A_0$ the absorbance of the negative controls, and $A_{total}$ the absorbance of 100% hemolysis wells, all at 350 nm.

Example 7

MTS Assays

A549 carcinoma-derived lung epithelial cells (ATTC CCL-185) were cultured in Ham's F12K media (ATTC, Manassas, Va.). A peptoid solution plate (100 µL/well) was prepared by serial dilution of aqueous peptoid stocks in media. Peptoid solutions were transferred onto a 96-well plate of day-old cell monolayers containing 100 µL/well media with ~5000 cells/well. MTS reagent (Promega Corporation, Madison, Wis.) (40 µL/well) was added to each well and the plate was incubated at 37° C. for 3 h, after which absorbance at 490 nm was determined. Percent inhibition was determined as $[1-(A-A_{test\ blank})/(A_{control}-A_{blank})] \times 100$, where A is the absorbance of the test well and $A_{control}$ the average absorbance of wells with cells exposed to media and MTS (no peptoid). $A_{test\ blank}$ (media, MTS, and peptoid) and $A_{blank}$ (media and MTS) were background absorbances measured in the absence of cells. The average of six replicates are reported, and error bars show one standard deviation.

Example 8

Specular X-Ray Reflectivity

XR experiments were carried out at the 9-ID beamline at the Advanced Photon Source, Argonne National Laboratory (Argonne, Ill.). The custom-built Langmuir trough was mounted in a helium-filled, sealed canister and equipped with a moveable single barrier. The surface pressure was measured using a Wilhelmy plate. Constant-pressure insertion experiments were performed at room temperature on Dulbecco's PBS (D-PBS) subphase. DPPG (Avanti Polar Lipids, Alabaster, Ala.) was dissolved to a known concentration in 65/35

(v/v) chloroform/methanol, then spread at the air-buffer interface using a glass syringe; organic solvent was allowed to evaporate for 10 minutes. The monolayer was compressed to the surface pressure thought to occur in cell membranes, 30 mN/m, and XR was performed on the pure lipid layer. Then, peptoid 1 dissolved in D-PBS was injected into the subphase to a total concentration of 6.26 µM (well above the MICs), and allowed to insert for approximately 45 minutes, after which XR measurements were again collected. The X-ray reflectivity (XR) profile was determined by the Fourier transform of the gradient of the electron density perpendicular to the interface. XR measurements were carried out over a range of angles corresponding to $q_z$ values of ~0-0.6 Å$^{-1}$, where $q_z = (4\pi/\lambda)\sin(\alpha)$, $\lambda$ is the wavelength, and $\alpha$ is the angle.

Example 9

Murine Intraperitoneal Infection Model

Bacteria was prepared by inoculating 5 mL of MHB with a single colony of *Staphyloccus aureus* (ATCC #25923) from a freshly streaked plate and grown overnight at 37 C. The following morning, the bacteria was subcultured by diluting 1/3 in MHB and grown for approximately 1.5 hours. The bacteria were then diluted 10-fold in a 5% mucin in PBS solution and thoroughly mixed. A sample was reserved to later determine the amount of bacteria the mice received.

Mice were weighed, marked, and injected I.P. with 200 uL of *S. aureus* inoculum. Four hours post infection, mice were treated I.P. with 4 mg/kg peptoid (~100 ug per mouse). The infection is allowed to proceed overnight. Mice were euthanized by $CO_2$ asphyxiation after 24 hours, and the peritoneal cavity was exposed and lavaged with 5 mL PBS. The lavage was mixed and reserved on ice until plating. The lavages were diluted to $10^{-5}$ (in 1/10 increments) in PBS, and all dilutions were plated onto MH agar, in duplicate. 50 uL of lavage was spot plated, allowed to dry, and incubated overnight at 37° C. Colonies were counted the following day, and the CFU/ml of each sample was calculated. Plates that had too many colonies to count were assigned an arbitrary number of 1000 colonies.

Example 10

Compound Synthesis and Purification

Peptoids were synthesized using an ABI 433A peptide synthesizer (Applied Biosystems, Inc.) on Rink amide MBHA resin (Novabiochem, Inc.) using the submonomer approach[3]. Briefly, bromoacetic acid, activated by diisopropylcarbodiimide was used to form a bromocetylated intermediate on the terminal amide group. Bromide was then substituted with the desired primary amine through $S_N2$ displacement to build the peptoid chain. The amines used in peptoid synthesis include benzylamine, octadecylamine, (s)-(+)-2-amino-3-methylbutane, (s)-α-methylbenzylamine, (r)-α-methylbenzylamine (all purchased from Sigma-Aldrich), and N-tert-butoxycarbonyl-1,4 diaminobutane (Nlys) that was made using a published procedure[83]. Resin-bound peptoids were then exposed to a mixture of trifluoroacetic acid (TFA): triisopropylsilane:water (95:2.5:2.5, v:v:v) for ten minutes to cleave peptoids from the solid phase. Peptoids were purified by reversed-phase HPLC(RP-HPLC) (Waters Corporation) using a C18 column and a linear acetonitrile/water gradient. A final purity greater than 97% as measured by analytical RP-HPLC (Waters Corporation) was achieved, and the identity of each molecule was checked using electrospray ionization mass spectrometry. All reagents were purchased from Sigma Aldrich.

Example 11

Circular Dichroism Spectroscopy

A Jasco 715 spectropolarimeter was used to perform all CD measurements in a cylindrical quartz cell with a path length of 0.02 cm. Measurements were taken over the range of 190 nm to 280 nm at a scanning rate of 100 nm/min. Other parameters include data pitch of 0.2 nm, bandwidth of 1 nm, response time of 2 seconds, and sensitivity of 100 mdeg. Compound concentration was 60 µM in 10 mM Tris buffer (pH 7.4). For samples in the presence of SUVs, the lipid concentration was 5 mM. 40 accumulations were collected for each sample.

Example 12

Screening Antibacterial Assays

MICs were determined in 96-well microtiter plates in accordance with CLSI M7-A6 protocols. Peptoid solutions with 50 µL total volume were prepared using 2:1 serial dilutions. 50 µL of bacteria inoculum ($1 \times 10^6$ CFU/mL) prepared in cation-adjusted Mueller-Hinton broth (CAMHB) was added to test wells. Control wells contained 100 µL MHB (no growth) or 50 µL inoculums with 50 µL MHB with no peptoid. The MIC was taken as the lowest concentration of peptoid that completely inhibited bacterial growth after 16 hours of incubation at 35° C. Reported values were reproducible over three experiments, each containing two parallel trials.

Example 13

Broad-Spectrum Antibacterial Assays

MICs of compounds were determined by microdilution procedure in Mueller-Hinton broth (MHB) in accordance with CLSI M7-A6 protocols in a manner similar to that described for the screen antibacterial assays. Inoculated microtiter plates were incubated at 35° C. for 24 hours prior to the result being recorded. Four ATCC strains that were used as standards are recommended by CLSI: *Pseudomonas aeruginosa* ATCC 27853, *Escherichia coli* ATCC 25922, *Staphylococcus aureus* ATCC 29213 and *Enterococcus faecalis* ATCC 29212. Other strains from the ATCC collection include *Proteus vulgaris* ATCC 49132, *Proteus mirabilis* ATCC 35659, *Klebsiella pneumoniae* ATCC 33495, *Enterobacter aerogenes* ATCC 35029 and *Serratia marcescens* ATCC 13880. *S. aureus* NRS100 (COL) is a well characterized methicillian-resistant *S. aureus* (MRSA) strain. The strains *S. aureus* VAN1 and *S. aureus* VAN2, vancomycin resistant MRSA strains that were isolated in Michigan and Pennsylvania, were the first vancomycin-resistant strains clinically isolated. *S. aureus* NRS119 and *S. aureus* NRS120 are linezolid-resistant isolates from the Network on Antimicrobial Resistance in *S. aureus* (NARSA) collection. *E. faecalis* 99 and *E. faecium* 106 are vancomycin-resistant enterococcal strains.

Example 14

Hemolysis Assays

Erythrocytes were isolated from freshly drawn, heparanized human blood and resuspended in PBS (pH 7.4) to make a 20% volume suspension. Peptoid solutions were prepared by serial dilution (2:1) in a 96-well microtiter plate. For test wells, 100 µL of erythrocyte suspension was added to 100 µL of peptoid solution in PBS; PBS without peptoid was used as the negative control and 0.2 vol % Triton X-100 as the positive control that indicates 100% hemolysis. After 1 hour incubation at 37° C., each well was diluted with 150 µL PBS.

Plates were then centrifuged at 1,200×g for 15 minutes to pellet the cells. 30 μL of the supernatant from each well were transferred to the corresponding well of a second 96-well plate that contains 70 μL PBS. Using a plate reader, the absorbance at 350 nm was measured, and percent hemolysis was defined as $(A-A_0)/(A_{total}-A_0)\times100$, where A is the absorbance of the test well, $A_0$ the average absorbance of negative controls, and $A_{total}$ the average absorbance of 100% hemolysis wells.

Example 15

MTS Assays

NIH/3T3 cells (ATCC Corporation) cultured at 37° C. and 5% $CO_2$ in complete Dulbecco's modified eagle's media (CDMEM) supplemented with 1% sodium pyruvate, 1% penicillin-streptomycin, 1.5 g/L $NaHCO_3$, and 10% fetal bovine serum. Cells were seeded at a density of 5,000 cells per well for NIH/3T3 cells in 96-well plates (100 μl total volume). A peptoid solution plate (100 μL total volume per well) was prepared by serial dilution of aqueous peptoid stock solution in Hank's balanced salt solution (HBSS) media. The day-old cell monolayers were washed with HBSS and media was replaced with 100 μl HBSS. The contents of the peptoid solution plate were transferred onto corresponding wells of the cell monolayer plate, and 40 μL MTS reagent (Promega, Inc.) was added to each well. After incubating for 3 hours at 37° C., absorbance at 490 nm was determined. The percentage inhibition was determined as $[1-(A-A_{testblank})/(A_{control}-A_{blank})]\times100$, where A is the absorbance of the test well and $A_{control}$ the average absorbance of the wells with cells exposed to media and MTS (no peptoid). $A_{testblank}$ (media, MTS, and peptoid) and $A_{blank}$ (media and MTS) were measured as background absorbances in the absence of cells. The average of six replicates is reported.

We claim:

1. A poly-N-substituted glycine antibiotic compound of a formula

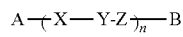

wherein A is a terminal N-alkyl substituted glycine residue, where said alkyl substituent is selected from about $C_4$ to about $C_{20}$ linear, branched and cyclic alkyl moieties; n is an integer selected from 1-3; B is selected from $NH_2$, one and two N-substituted glycine residues, said N-substituents independently selected from natural α-amino acid side chain moieties, isomers and carbon homologs thereof; X, Y and Z are independently selected from N-substituted glycine residues, said N-substituents independently selected from natural α-amino acid side chain moieties, isomers and carbon homologs thereof, and proline residues, at least one of said X, Y and Z residues is $N_{Lys}$ and at least one said N-substituent is chiral.

2. The compound of claim 1 wherein at least one of Y and Z are proline residues.

3. The compound of claim 2 wherein Y and Z are proline residues.

4. The compound of claim 1 wherein A is a terminal N-alkyl substituted glycine residue, said alkyl substituent selected from about $C_6$ to about $C_{18}$ linear alkyl moieties; B is $NH_2$; and n is selected from 1 and 2.

5. The compound of claim 1 wherein A is a terminal N-alkyl substituted glycine residue, said alkyl substituent selected from about $C_6$ to about $C_{18}$ linear alkyl moieties; B is an $N_{Lys}$ residue; and n is 1.

SEQUENCE LISTING

```
<160> NUMBER OF SEQ ID NOS: 2

<210> SEQ ID NO 1
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 1

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 2
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 2

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

6. A poly-N-alkyl substituted glycine antibiotic compound of a formula

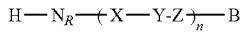

wherein B is selected from NH$_2$ and X'; X, Y, Z and X' are independently selected from N-substituted glycine residues, where said substituents are independently selected from natural α-amino acid side chain moieties, isomers and carbon homologs thereof, and proline residues, at least one of said X, Y, Z and X' residues is N$_{Lys}$ and at least one said N-substituent is chiral; n is an integer selected from 1 and 2; and R is an N-alkyl substituent of said N$_R$ glycine residue, said substituent selected from about C$_4$ to about C$_{20}$ linear, branched and cyclic alkyl moieties.

7. The compound of claim 6 wherein n is 2; and B is NH$_2$.

8. The compound of claim 6 wherein n is 1; and B is X'.

9. The compound of claim 8 wherein at least one of X and X' are N$_{Lys}$ residues.

10. The compound of claim 9 wherein said N-alkyl substituent is selected from about C$_6$ to about C$_{18}$ linear, branched and cyclic alkyl moieties.

11. The compound of claim 10 wherein X and X' are N$_{Lys}$ residues.

12. The compound of claim 11 of a formula

13. A poly-N-substituted glycine antibiotic compound comprising an N-terminal N-alkyl substituted glycine residue, where said alkyl substituent is selected from about C$_4$ to about C$_{20}$ linear, branched and cyclic alkyl moieties; a C-terminus selected from NH$_2$, one and two N-substituted glycine residues, said N-substituents independently selected from α-amino acid side chain moieties and carbon homologs thereof; and 2 to about 15 monomeric residues between said N- and C-termini, each said residue independently selected from proline residues and N-substituted glycine residues, said N-substituents independently selected from natural α-amino acid side chain moieties, isomers and carbon homologs thereof, at least one said monomeric residue is N$_{Lys}$ and at least one said N-substituent is chiral, said monomeric residues selected to provide said compound a non-periodic sequence of monomeric residues.

14. The compound of claim 13 wherein said N-terminus is an N-alkyl substituted glycine residue, said alkyl substituent selected from about C$_6$ to about C$_{18}$ linear alkyl moieties.

15. The compound of claim 14 wherein said monomeric residues comprise 2-5 (X-Y-Z) non-periodic trimers.

16. The compound of claim 15 wherein at least one X, Y and Z in each of said trimers is selected to interrupt 3-fold periodicity.

17. The compound of claim 15 wherein said monomeric residues comprise at least two non-consecutive repeat trimers, with at least one residue therebetween.

18. The compound of claim 17 wherein at least one X in at least one said trimer is an N$_{Lys}$ residue, and at least one of Y and Z in at least one said trimer is a proline residue.

* * * * *